(12) United States Patent
Larossa et al.

(10) Patent No.: US 6,607,885 B1
(45) Date of Patent: Aug. 19, 2003

(54) METHOD FOR HIGH-DENSITY MICROARRAY MEDICATED GENE EXPRESSION PROFILING

(75) Inventors: Robert A. Larossa, West Chester, PA (US); Yan Wei, West Caldwell, NJ (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 2 days.

(21) Appl. No.: 09/686,383

(22) Filed: Oct. 11, 2000

Related U.S. Application Data

(60) Provisional application No. 60/159,898, filed on Oct. 15, 1999.

(51) Int. Cl.⁷ .............................. C12Q 1/68; C12Q 1/70; C12P 19/34; C12N 1/20
(52) U.S. Cl. .............................. 435/6; 435/5; 435/91.1; 435/91.2; 435/252.31; 435/252.32; 435/252.33; 435/252.34; 435/252.5; 536/23.1; 536/24.3; 536/24.32; 536/24.33
(58) Field of Search .............................. 435/5, 6, 91.1, 435/91.2, 252.31, 252.33, 252.35, 252.34, 252.5; 536/23.1, 24.33, 24.3, 24.32; 422/50, 68.1

(56) References Cited

U.S. PATENT DOCUMENTS

| | | | |
|---|---|---|---|
| 5,770,151 A | 6/1998 | Roach et al. | 422/63 |
| 5,807,522 A | 9/1998 | Brown et al. | 422/50 |
| 5,837,832 A | 11/1998 | Chee et al. | 536/22.1 |
| 5,952,180 A | 9/1999 | Ju | 435/6 |
| 6,040,138 A | 3/2000 | Lockhart et al. | 435/6 |
| 6,045,996 A | 4/2000 | Cronin et al. | 435/6 |

FOREIGN PATENT DOCUMENTS

| | | | |
|---|---|---|---|
| WO | WO 92/10588 | 6/1992 | C12Q/1/68 |
| WO | WO 95/35505 | 12/1995 | G01N/33/543 |
| WO | WO 00/39339 A1 | 7/2000 | |

OTHER PUBLICATIONS

Wodicka Et Al., "Genome–Wide Expression Monitoring in Saccharomyces Cerevisiae" Nature Biotechnology, Nature Publishing US, vol. 15, Dec. 1997, pp. 1359–1367, XP002100297.
Richmond, C. Et Al., "Genome–Wide expression profiling in *Escherichia coli* K–12" Nucleic Acids Research, Oxford University Press, Surry, GB, vol. 27, No. 19, Oct. 1, 1999, pp. 3821–3835, XP002184216.
Lashkari, D. Et Al., "Yeast Microarrays for Genome Wide Parallel Genetic and Gene Expression Analysis", Proceeding of the National Academy of Sciences of USA, National Academy of Science, washington, US, vol. 94, Nov. 1997, pp. 13057–13062, XP002115013.
Kenyon and Walker, Proc. Natl. Acad. Sci. U.S.A., 77:2819–2823 (1980).
Van Bogelen et al., J. Bacteriol. 169:26–32 (1987).
Spector et al. J. Bacteriol. 170:345–351 (1988).
DeRisi et al., Science, 278:680–686 (1997).
Chuang et al., J. Bacteriol. 175:2026–2036 (1993).
Richmond et al., Nucleic Acids Research, 19:3821–3835 (1999).
Kearney et al., Oxidative Pretreatment Accelerates TNT Metabolism in Soils, Chemosphere, col. 12, No. 11/12, pp 1583–1597 (1983).

*Primary Examiner*—Kenneth R. Horlick
*Assistant Examiner*—Cynthia Wilder

(57) ABSTRACT

The global effect on genes under different environmental conditions can be determined by a comprehensive gene expression profile. The present invention provides a method to monitor the changes in comprehensive cellular gene expression levels at single length resolution by using a high-density microarray prepared with a comprehensive collection of ORFs of a genome. Under different environmental conditions, directly and indirectly affected genes can be detected as the gene expression levels are induced or repressed in comparison to the control.

14 Claims, 5 Drawing Sheets

METHOD FOR HIGH-DENSITY MICROARRAY MEDICATED GENE EXPRESSION PROFILING

Figure 1A:
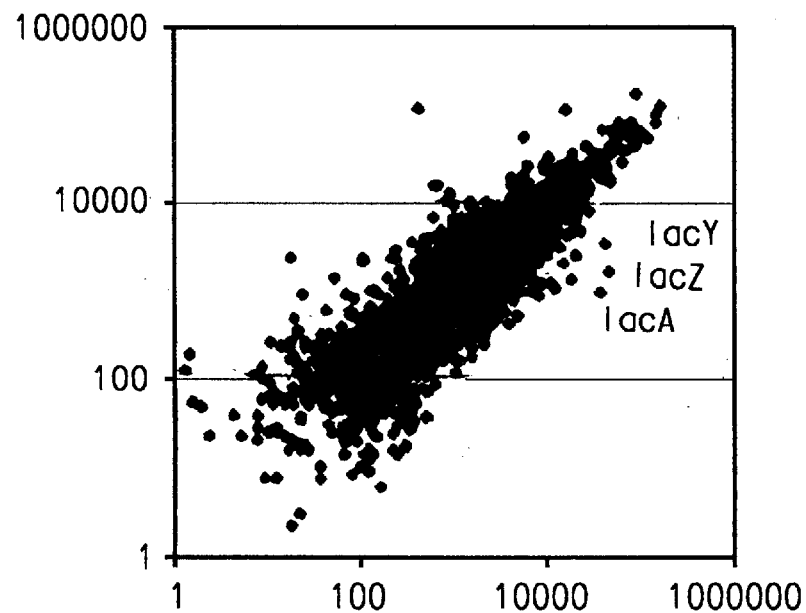

This application claims the benefit of U.S. Provisional Application No. 60/159,898, filed Oct. 15, 1999.

FIELD OF THE INVENTION

This invention is in the field of bacterial gene expression. More specifically, this invention is a method for the high density, microarray-mediated gene expression profiling of *Escherichia coli* for comprehensive gene expression analysis.

BACKGROUND OF THE INVENTION

*Escherichia coil* has been exhaustively studied for over 50 years. Early experiments measured the molecular fluxes from small compounds into macromolecular constituents. These studies were followed by others in which small molecule pools of central metabolic building blocks, nucleotides and amino acids were determined. The levels of several macromolecular components, including individual species of proteins, have been measured. Such measurements of the steady state provide a census of the cellular content while changes upon imposition of a stress catalogue the cell's fight for survival. This response to an insulting or adverse condition can take many forms from relieving end product inhibition to derepressing transcription.

In *E. coli*, experiments to define stress-related, global regulatory responses have often relied upon one of two approaches. In the first, operon fusions induced by a particular stress are isolated. In the second, proteomic measures in which the protein fractions from stressed and un-stressed cultures are separated by a two-dimensional method and then compared. Each method has an inherent technological hurdle; for the former, the map location of responsive gene fusions must be known precisely, and for the latter, induced or repressed proteins excised from the two-dimensional gels must be identified.

Another method uses a transposon-mediated mutagenesis (Spector et al. *J. Bacteriol.* 170:345–351 (1988)). A reporter gene is inserted at a random location in the genome using a transposon. By assaying for the reporter gene before and after the treatment, genes affected by the treatment can be mapped and cloned by using the linked transposon as a marker. However, this method is limited to non-essential genes.

Alternatively, mRNA measurements utilizing techniques (such as hybridization to DNA and primer extension) have allowed the monitoring of individual gene's expression profiles. DeRisi et al. (*Science* 278:680–686 (1997)) reported the expression profiling of most yeast genes. The measurements were facilitated by high-density arrays of individual genes and specific labeling of cDNA copies of eukaryotic mRNA using polyA tail-specific primers. The lack of a polyA tail and the extremely short bacterial mRNA half life represent hurdles for the application of DNA micro-array technology to prokaryotic research.

A comprehensive expression profiling has been performed previously with the yeast *Saccharomyces cerevisiae*. Adaptation of RNA isolation and labeling protocols from eukaryotes to prokaryotes is not straightforward since eukaryotic mRNA manipulations often exploit 3'-polyadenylation of this molecular species.

Chuang et al. (*J. Bacterol.* 175:2026–2036 (1993)) reported an expression profiling using large DNA fragments from an ordered λ library of *E. coli* genomic fragments as a capture reagent. It allowed the comparison of the expression patterns from large portions of DNA fragments by comparing mRNA levels from stressed and unstressed *E. coli* cultures. The resolution of this method, however, was unsatisfactory. Expression of groups of genes, as opposed to the expression of each individual gene was measured. Moreover, the method used radio-labeled DNA as a probe with the incumbent need for safety precautions. Furthermore, the use of radio-labeled probe prevents the simultaneous measurement of the expression level in a test sample and a control sample.

Richmond et al. (*Nucleic Acids Research*, 19:3821–3835 (1999)) has recently reported genome-wide expression profiling of *E. coli* at a single ORF level of resolution. Changes in RNA levels after exposure to heat shock or IPTG were analyzed using comprehensive low density blots of individual ORFs on a nylon matrix and comprehensive high density arrays of individual ORFs spotted on glass slides. The results of the two methods were compared.

The methods recited above permit monitoring of the effect of environmental changes on gene expression by comparing expression levels of a limited number of genes. They, however, fail to monitor the comprehensive responses of a preponderance of individual genes in the genome of an organism in reliable, useful manner.

The problem to be solved, therefore, is to provide a way to measure the comprehensive gene expression profile analysis of the organism.

SUMMARY OF THE INVENTION

The invention provides a method for identifying gene expression changes within a bacterial species comprising:

(a) providing a comprehensive micro-array synthesized from DNA comprised in a bacterial species;

(b) generating a first set of labeled probes from bacterial RNA, the RNA isolated from the bacterial species of step (a);

(c) hybridizing the first:set of labeled probes of step (b) to the comprehensive micro-array of step (a), wherein hybridization results in a detectable signal generated from the labeled probe;

(d) measuring the signal generated by the hybridization of the first set of labeled probe to the comprehensive micro-array of step (c);

(e) subjecting the bacterial species of step (a) to a gene expression altering condition whereby the gene expression profile of the bacterial species is altered to produce a modified bacterial species;

(f) generating a second set of labeled probes from bacterial RNA, the RNA isolated from the modified bacterial species of step (e);

(g) hybridizing the second set of labeled probes of step (f) to the comprehensive micro-array of step (a), wherein hybridization results in a detectable signal generated from the labeled probe;

(h) measuring the signal generated by the hybridization of the second set of labeled probes to the comprehensive micro-array of step (g); and (i) comparing signal generated from the first hybridization to the signal generated from the second hybridization to identify gene expression changes within a bacterial species.

Additionally the invention provides a method for identifying gene expression changes within a bacterial strain comprising:

(a) providing a comprehensive micro-array synthesized from DNA comprised in a bacterial species (b) generating a first set of fluorescent cDNA from bacterial RNA, the RNA isolated from the bacterial species of step (a);

(c) hybridizing the first set of fluorescent cDNA of step (b) to the comprehensive micro-array of step (a), wherein hybridization results in a detectable signal generated from the fluorescent cDNA;

(d) measuring the signal generated by the hybridization of the first set of fluorescent cDNA to the comprehensive micro-array of step (c);

(e) subjecting the bacterial species of step (a) to a gene expression altering condition whereby the gene expression profile of the bacterial species is altered to produce a modified bacterial species;

(f) generating a second set of fluorescent cDNA from bacterial RNA, the RNA isolated from the modified bacterial species of step (e);

(g) hybridizing the second set of fluorescent cDNA of step (f) to the comprehensive micro-array of step (a), wherein hybridization results in a detectable signal generated from the fluorescent cDNA;

(h) measuring the signal generated by the hybridization of the second set of fluorescent cDNA to the comprehensive micro-array of step (g); and (i) comparing signal generated from the first hybridization to the signal generated from the second hybridization to identify gene expression changes within a bacterial species.

In an alternate embodiment the invention provides a method for identifying gene expression changes within a genome comprising:

(a) providing a comprehensive micro-array synthesized from DNA comprised in a prokaryotic or eukaryotic species;

(b) generating a control set of fluorescent cDNA from total or polyadenylated RNA, the RNA isolated from the species of step (a), the fluorescent cDNA comprising at least one first fluorescent label and at least one different second fluorescent label;

(c) mixing the control set of fluorescent cDNA labeled with the at least one first label with the control set of fluorescent cDNA labeled with the at least second first label to for a dual labeled control cDNA;

(d) hybridizing the dual labeled control set of fluorescent cDNA of step (c) to the comprehensive micro-array of step (a), wherein hybridization results in a detectable signal generated from the fluorescent cDNA;

(e) measuring the signal generated by the hybridization of the dual labeled control set of fluorescent cDNA to the comprehensive micro-array of step (c);

(f) subjecting the prokaryote or eukaryote of step (a) to a gene expression altering condition whereby the gene expression profile of the prokaryote or eukaryote is altered to produce a modified prokaryote or eukaryote;

(g) generating an experimental set of fluorescent cDNA from total or polyadenylated RNA, the RNA isolated from the modified prokaryote or eukaryote of step (e), the fluorescent cDNA comprising the first fluorescent label and the different second fluorescent label to step (b);

(h) mixing the experimental set of fluorescent cDNA labeled with the at least one first label with the experimental set of fluorescent cDNA labeled with the at least second first label to form a dual labeled experimental cDNA;

(i) hybridizing the experimental set of fluorescent cDNA of step (h) to the comprehensive micro-array of step (a), wherein hybridization results in a detectable signal generated from the fluorescent cDNA;

(j) measuring the signal generated by the hybridization of the second set of fluorescent cDNA to the comprehensive micro-array of step (g); and (k) comparing signal generated from the dual labeled control hybridization with the dual labeled experimental hybridization to identify gene expression changes within a prokaryotic or eukaryotic species.

In another embodiment the invention provides a method for quantitating the amount of protein specifying RNA contained within a genome comprising:

(a) providing a comprehensive micro-array comprising a multiplicity of genes synthesized from genomic DNA comprised in a prokaryotic or eukaryotic organism;

(b) generating a set of fluorescent cDNA from total or poly-adenylated RNA isolated from the prokaryotic or eukaryotic organism of step (a);

(c) generating a set of fluorescent DNA from genomic DNA isolated from the prokaryotic or eukaryotic organism of step (a);

(d) hybridizing the fluorescent cDNA of step (b) to the comprehensive micro-array of step (a), wherein hybridization results in a first fluorescent signal generated from the fluorescent cDNA for each gene;

(e) hybridizing the fluorescent DNA of step (c) to the comprehensive micro-array of step (a), wherein hybridization results in a second fluorescent signal generated from the fluorescent DNA for each gene; and (f) dividing, for each open reading from, the first fluorescent signal into the second fluorescent signal to provide a quantitated measure of the amount of protein specifying RNA for each gene.

The methods of the present invention are applicable to genomes contained within a variety of organisms including bacteria, cyanobacteria, yeasts, filamentous fungi, plant cells and animal cells.

The present methods of identifying gene expression changes within genome may be additionally coupled with the methods of quantitating the amount of protein specifying RNA contained within a genome as disclosed herein.

BRIEF DESCRIPTION OF THE DRAWINGS AND SEQUENCE DESCRIPTIONS

FIG. 1A describes the gene expression analysis of IPTG induction in a single hybridization experiment using different slide sets as capture reagents for Cy3-labeled cDNA derived from treated and control cells and plotted in log-log form.

Figure 1B:
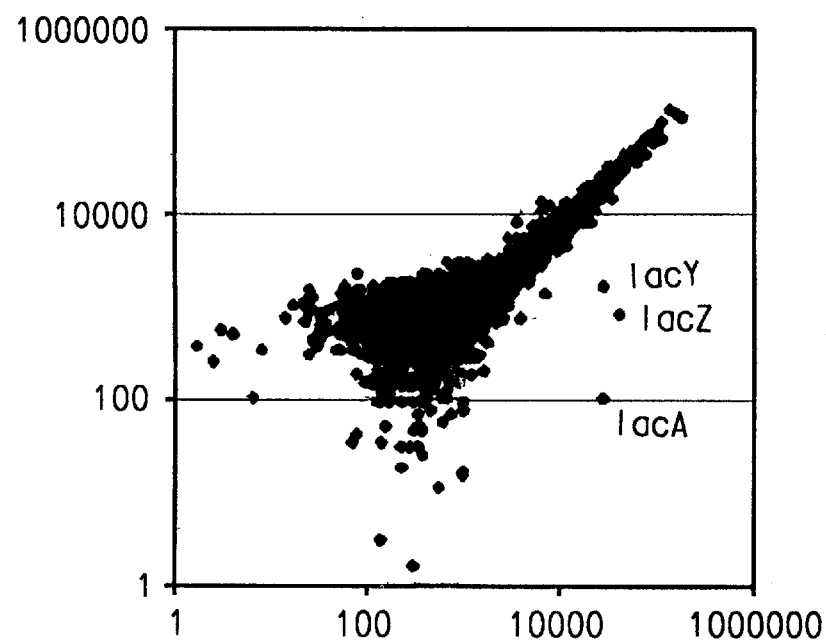

FIG. 1B describes the gene expression analysis of IPTG induction by labeling the control sample with Cy5 and the induced sample with Cy3 before hybridizing to a single set of 3 slides.

Figure 1C:
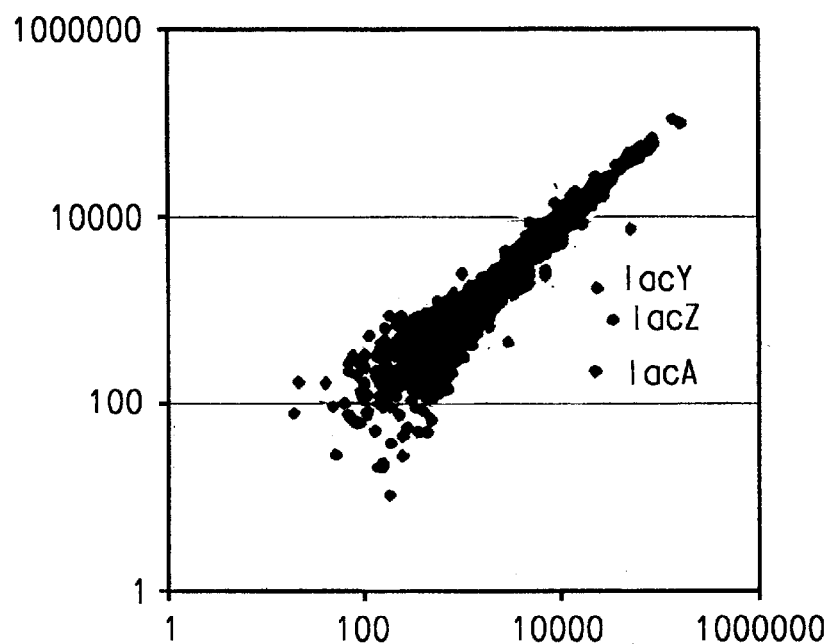

FIG. 1C describes an average of induced RNA and control RNA with Cy3 from IPTG induction, generated by label swapping.

Figure 1D:
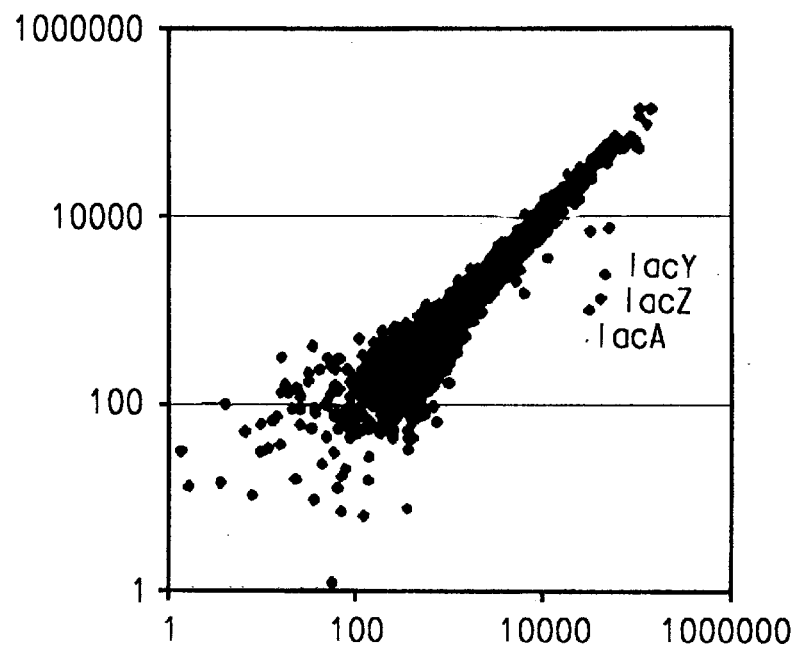

FIG. 1D describes data replicating the results shown in FIG. 1C.

Figure 1E:
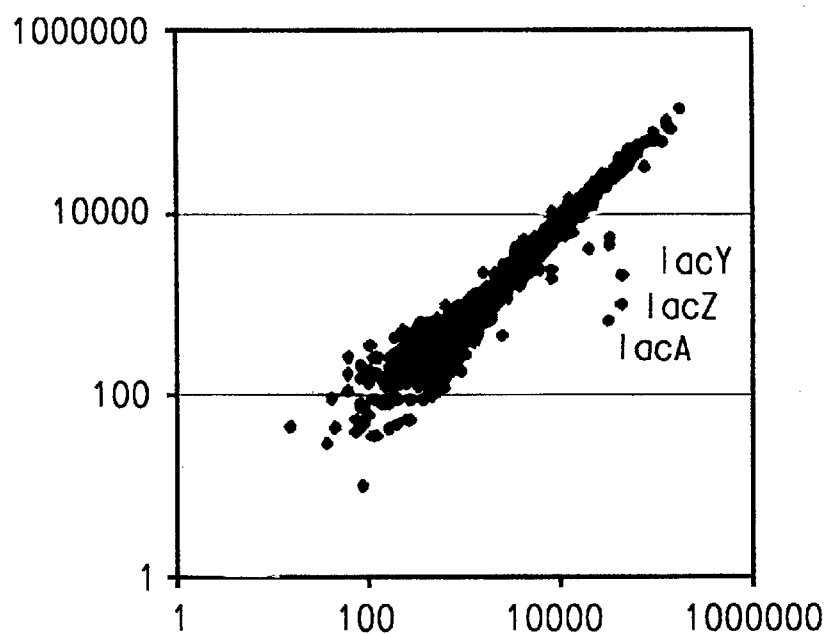

FIG. 1E describes an averaging of the data of FIG. 1C and FIG. 1D.

Figure 2:
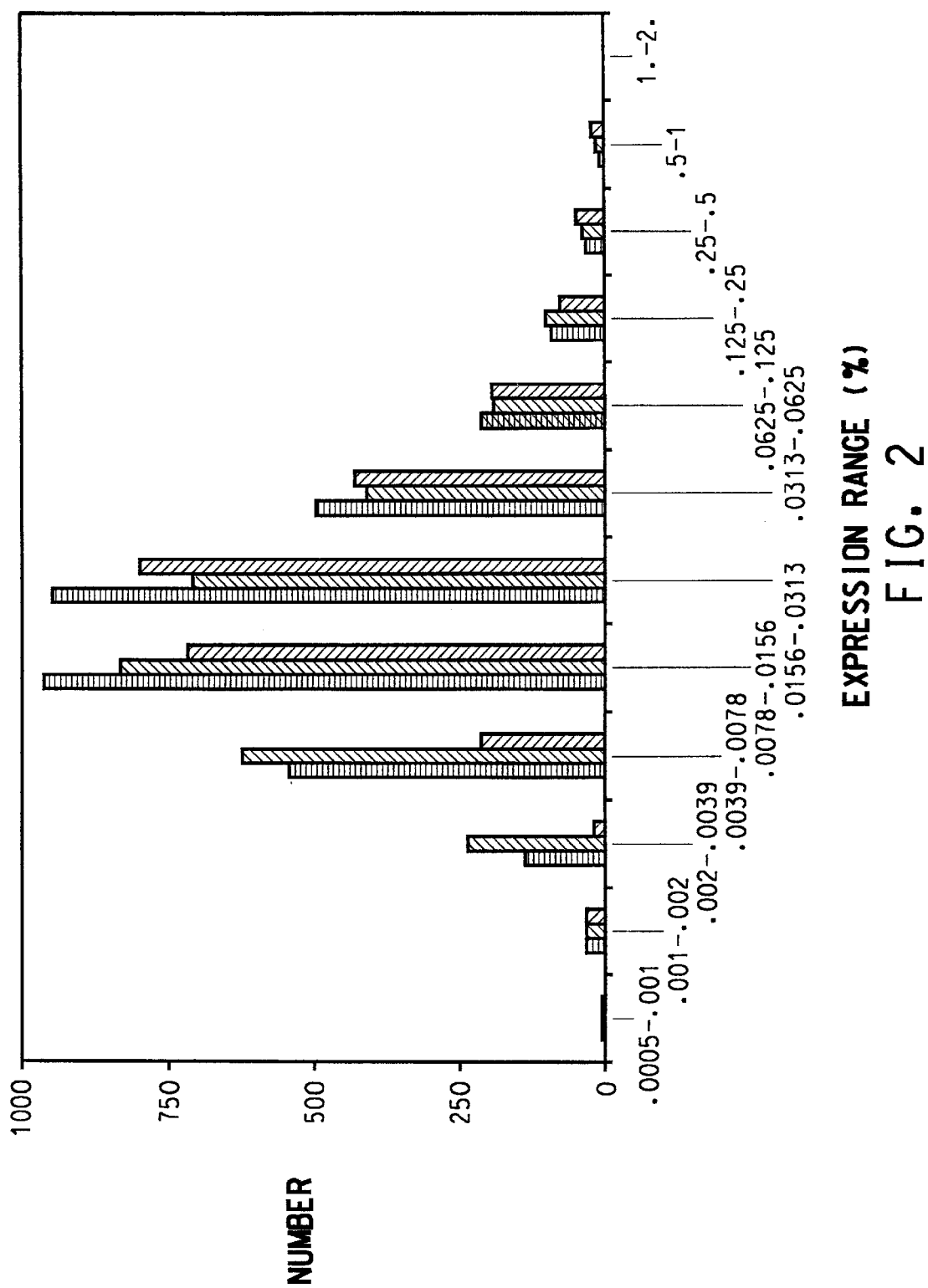

FIG. 2 describes the distribution of gene expression levels for cells grown in minimal or rich medium.

Figure 3:
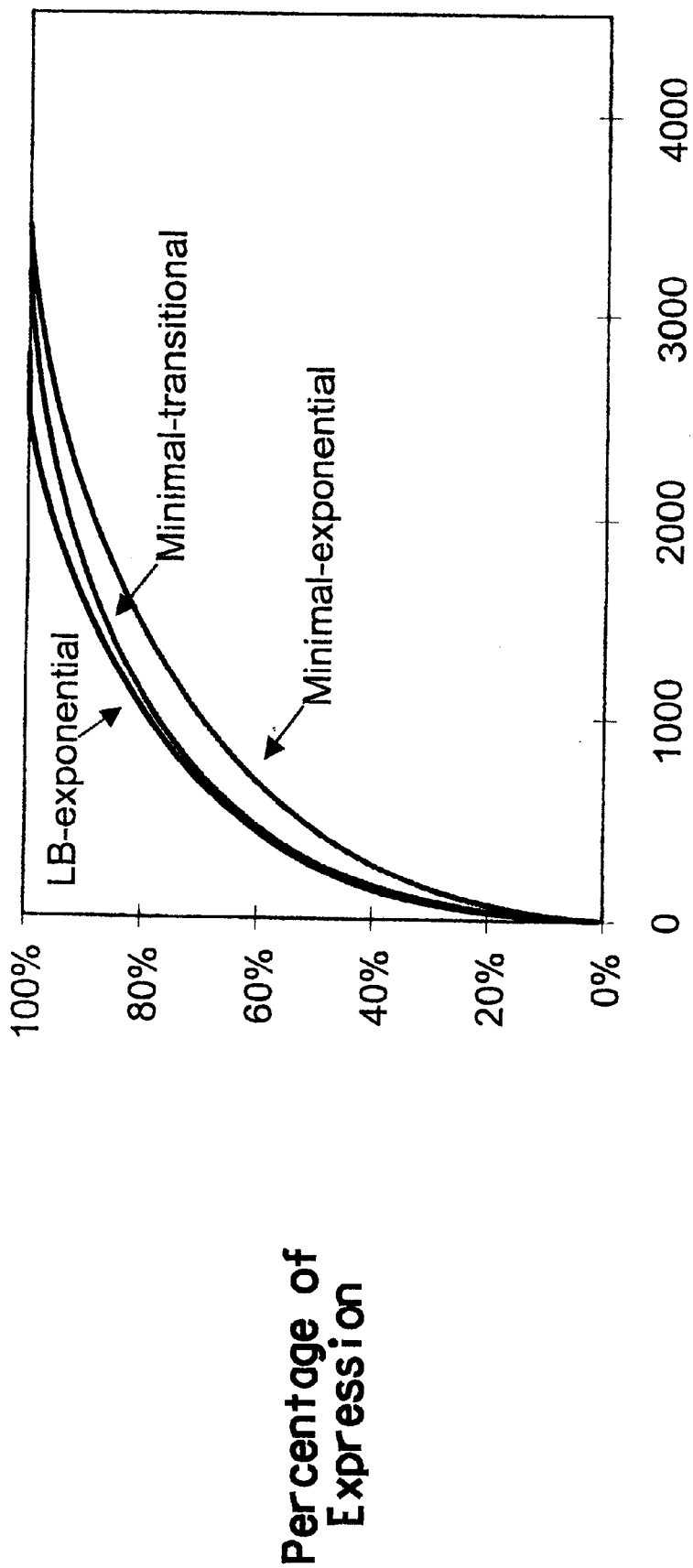

FIG. 3 describes the fractional (summed open reading frame transcripts/total open reading frame transcripts) analysis of gene expression.

The invention can be more fully understood from the following detailed description and the accompanying sequence descriptions which form a part of this application.

The following sequences comply with 37 C.F.R. 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 and 2 are primers used in the amplification of the sdiA gene.

DETAILED DESCRIPTION OF THE INVENTION

Applicants have solved the stated problem by providing a method to measure a comprehensive mRNA expression of *E. coli* using a high density DNA microarray with a near-complete collection of *E. coli* open reading frames (ORFs).

The present invention advances the art by providing:

(i) the first instance of a comprehensive micro-array comprising greater than 75% of all open reading frames from a prokaryotic organism, overcoming the problems of high concentration of endogenous RNAase and ribosomal RNA;

(ii) a method for quantitating the amount of each protein specifying RNA contained within a culture; and (iii) a method for decreasing the background noise generated within a gene expression profile through the combination of multiple signal generating labels.

The present invention has utility in many different fields. Many discovery compounds can be screened by comparing their gene expression profile to a known compound that affects the desirable target gene products. Additionally gene expression profiles are good indicators of genotypic alterations among strains. The present invention may allow the discovery of complementary target inhibitors in combination drug-therapy and may be used as a modeling system to test perturbations in process conditions to determine the conditions for the high yield of desired production in various bio-processes and biotransformations.

In this disclosure, a number of terms and abbreviations are used. The following definitions are provided.

"Open reading frame" is abbreviated ORF. The term "ORF" is refers to a gene that specifies a protein.

"Polymerase chain reaction" is abbreviated PCR.

The term "micro-array" means an array of regions having a density of discrete regions of oligonucleotides of at least about 100/cm$^2$, and preferably at least about 1000/cm$^2$.

The term "comprehensive micro array" refers to high-density micro-array containing at least 75% of all open reading frames of the organism.

The term "expression profile" refers to the expression of groups of genes.

The term "gene expression profile" refers to the expression of an individual gene and of suites of individual genes.

The "comprehensive expression profile" refers to the gene expression profile of more than 75% of all genes in the genome.

The term "high density" as used in conjunction with micro-array means and array having an array density of generally greater than about 60, more generally greater than about 100, most generally greater than about 600, often greater than about 1000, more often greater than about 5,000, most often greater than about 10,000, preferably greater than about 40,000 more preferably greater than about 100,000, and most preferably greater than about 400,000 different nucleic acids per cm.$^2$ As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The term "probe" refers to a single-stranded nucleic acid molecule that can base pair with a complementary single stranded target nucleic acid to form a double-stranded molecule.

The term "genotype" refers to the genetic constitution of an organism as distinguished from its physical appearance.

The term "genomic DNA" refers to total DNA from an organism.

The term "total RNA" refers to non-fractionated RNA from an organism.

The term "protein specifying RNA" or "protein specifying transcript" or "mRNA" refers to RNA derived from ORF.

The term "label" will refer to a substance which may be incorporated into DNA or RNA which will emit a detectable signal under various conditions. Typically a label will be a fluorescent moiety.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein. The conditions of temperature and ionic strength determine the "stringency" of the hybridization. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). Furthermore, the skilled artisan will recognize that the temperature and wash solution salt concentration may be adjusted as necessary according to factors such as length of the probe.

The term "complementary" is used to describe the relationship between nucleotide bases that are capable to hybridizing to one another. For example, with respect to DNA, adenosine is complementary to thymine and cytosine is complementary to guanine.

"Gene" refers to the part of the genome specifying a macromolecular product be it RNA or a protein and include regulatory sequences preceding (5' non-coding sequences) and following (3' non-coding sequences) the coding sequence.

A "genetic site" refers to a genomic region at which a gene product operates.

"Coding sequence" or "open reading frame" (ORF) refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

"RNA transcript" refers to the product resulting from RNA polymerase-catalyzed transcription of a DNA sequence. When the RNA transcript is the polymer product of an RNA polymerase, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA.

The term "expression", as used herein, refers to the transcription and stable accumulation of sense (mRNA) or antisense RNA derived from genomic DNA. Expression may also refer to translation of mRNA into a polypeptide.

The term "stress" or "environmental stress" refers to the condition produced in a cell as the result of exposure to an environmental insult.

The term "insult" or "environmental insult" refers to any substance or environmental change that results in an alteration of normal cellular metabolism in a bacterial cell or population of cells. Environmental insults may include, but are not limited to, chemicals, environmental pollutants, heavy metals, changes in temperature, changes in pH, as well as agents producing oxidative damage, DNA damage, anaerobiosis, and changes in nitrate availability or pathogenesis.

The term "stress response" refers to the cellular response to an environmental insult.

The term "stress gene" refers to any gene whose transcription is induced as a result of environmental stress or by the presence of an environmental insult.

The term "modified bacterial species" refers to a bacterial culture that has been exposed to a stress or insult such that either it demonstrates a change in its gene expression profile. Typically the modified bacterial species is produced as the result of induction or challenge of the culture with a chemical or environmental challenge. Similarly, a "modified prokaryotic or eukaryotic species" refers to either a prokarytoic or eukaryotic organism that has been exposed to a stress or insult such that the gene expression profile of that organisms as been altered.

The term "log phase", "log phase growth", "exponential phase" or "exponential phase growth" refers to cell cultures of organisms growing under conditions permitting the exponential multiplication of the cell number.

The term "growth-altering environment" refers to energy, chemicals, or living things that have the capacity to either inhibit cell growth or kill cells. Inhibitory agents may include but are not limited to mutagens, antibiotics, UV light, gamma-rays, x-rays, extreme temperature, phage, macrophages, organic chemicals and inorganic chemicals.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

The present invention provides a method to measure the changes in gene expression profiles of prokaryotic organisms. The present invention also provides a method to measure the levels of protein specifying RNA in prokaryotic and/or eukaryotic organisms. The present invention provides a method to compare the gene expression patterns of two samples differing in one variable. The variables may include but are not limited to genotype, media, temperature, depletion or addition of nutrient, addition of an inhibitor, physical assault, irradiation, heat, cold, elevated or lowered pressure, desiccation, low or high ionic strength, and growth phases.

Gene expression profiles were determined under the following conditions to find: (a) differences in gene expression profiles caused by growth of *E. coli* in either minimal or rich medium, (b) changes in gene expression associated with the transition from exponential phase to stationary phase growth in minimal medium, and (c) the specificity of induction mediated by isopropylthiogalactoside (IPTG), the classic lac operon inducer, (d) the specificity of expression changes mediated by the amplification of sdiA, a positive activator of an operon that includes ftsQAZ, genes essential for septation, and (e) the changes in gene expression patterns with cells that cannot turn on the SOS stress response in comparison to wild type response when the cells are exposed to mitomycin C (MMC).

In its most basic form the present invention creates a comprehensive micro-array from a bacterial genome. Any bacteria is suitable for analysis by the method of the present invention where enteric bacteria (Escherichia, and Salmonella for example) as well as cyanobacteria (such as Rhodobacter and Synechocystis and Bacillus, Acinetobacter, Streptomyces, Methylobacter, and Pseudomona are particularly suitable.

One of skill in the art will appreciate that in order to measure the transcription level (and thereby the expression level) of a gene or genes, it is desirable to provide a nucleic acid sample comprising mRNA transcript(s) of the gene or genes, or nucleic acids derived from the mRNA transcript(s). As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, suitable samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

Typically the genes are amplified by methods of primer directed amplification such as polymerase chain reaction (PCR) (U.S. Pat. No. 4,683,202 (1987, Mullis, et al.) and U.S. Pat. No. 4,683,195 (1986, Mullis, et al.), ligase chain reaction (LCR) (Tabor et al., *Proc. Acad. Sci. U.S.A.*, 82, 1074–1078 (1985)) or strand displacement amplification (Walker et al., *Proc. Natl. Acad. Sci. U.S.A.*, 89, 392, (1992) for example.

The micro-array is comprehensive in that it incorporates at least 75% of all ORF's present in the genome. Amplified ORF's are then spotted on slides comprised of glass or some other solid substrate by methods well known in the art to form a micro-array. Methods of forming high density arrays of oligonucleotides, with a minimal number of synthetic steps are known (see for example Brown et al., U.S. Pat. No. 6,110,426). The oligonucleotide analogue array can be synthesized on a solid substrate by a variety of methods, including, but not limited to, light-directed chemical coupling, and mechanically directed coupling. See Pirrung et al., U.S. Pat. No. 5,143,854 (see also PCT Application No. WO 90/15070) and Fodor et al., PCT Publication Nos. WO 92/10092 and WO 93/09668 which disclose methods of forming vast arrays of peptides, oligonucleotides and other molecules using, for example, light-directed synthesis techniques. See also, Fodor et al., *Science*, 251, 767–77 (1991).

Bacteria typically contain from about 2000 to about 6000 ORF's per genome and the present method is suitable for genomes of this size where genomes of about 4000 ORF's are most suitable. The ORF's are arrayed in high density on at least one glass microscope slide. This is in contrast to a low density array where ORF's are arrayed on a membranous material such as nitrocellulose. The small surface area of the high density array (often less than about 10 $cm^2$, preferably less than about 5 $cm^2$ more preferably less than about 2 $cm^2$, and most preferably less than about 1.6 $cm.^2$) permits extremely uniform hybridization conditions (temperature regulation, salt content, etc.).

Once all the genes of ORF's from the genome are amplified, isolated and arrayed, a set of probes, bearing a signal generating label are synthesized. Probes may be randomly generated or may be synthesized based on the sequence of specific open reading frames. Probes of the present invention are typically single stranded nucleic acid sequences which are complementary to the nucleic acid sequences to be detected. Probes are "hybridizable" to the ORF's. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Signal generating labels that may be incorporated into the probes are well known in the art. For example labels may include but are not limited to fluorescent moieties, chemiluminescent moieties, particles, enzymes, radioactive tags, or light emitting moieties or molecules, where fluorescent moieties are preferred. Most preferred are fluorescent dyes capable of attaching to nucleic acids and emitting a fluorescent signal. A variety of dyes are known in the art such as fluorescein, Texas red, and rhodamine. Preferred in the present invention are the mono reactive dyes cy3 (146368-16-3) and cy5 (146368-14-1) both available commercially (i.e. Amersham Pharmacia Biotech, Arlington Heights, Ill.). Suitable dyes are discussed in U.S. Pat. No. 5,814,454 hereby incorporated by reference.

Labels may be incorporated by any of a number of means well known to those of skill in the art. However, in a preferred embodiment, the label is simultaneously incorporated during the amplification step in the preparation of the probe nucleic acids. Thus, for example, polymerase chain reaction (PCR) with labeled primers or labeled nucleotides will provide a labeled amplification product. In a preferred embodiment, reverse transcription or replication, using a labeled nucleotide (e.g. dye-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the synthesis is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Following incorporation of the label into the probe the probes are then hybridized to the micro-array using standard conditions where hybridization results in a double stranded nucleic acid, generating a detectable signal from the label at the site of capture reagent attachment to the surface. Typically the probe and array must be mixed with each other under conditions which will permit nucleic acid hybridization. This involves contacting the probe and array in the presence of an inorganic or organic salt under the proper concentration and temperature conditions. The probe and array nucleic acids must be in contact for a long enough time that any possible hybridization between the probe and sample nucleic acid may occur. The concentration of probe or array in the mixture will determine the time necessary for hybridization to occur. The higher the probe or array concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature [Van Ness and Chen (1991) *Nucl. Acids Res.* 19:5143–5151]. Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3 M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1 M sodium chloride, about 0.05 to 0.1 M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons), polyvinylpyrrolidone (about 250–500 kdal), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate. Methods of optimizing hybridization conditions are well known to those of skill in the art (see, e.g., Laboratory Techniques in Biochemistry and Molecular Biology, Vol. 24: Hybridization With Nucleic Acid Probes, P. Tijssen, ed. Elsevier, N.Y., (1993)) and Maniatis, supra.

The basis of gene expression profiling via micro-array technology relies on comparing an organism under a variety of conditions that result in alteration of the genes expressed. Within the context of the present invention a single population of cells was exposed to a variety of stresses that resulted in the alteration of gene expression. Alternatively, the cellular environment may be kept constant and the genotype may be altered. Typical stresses that result in an alteration in gene expression profile will include, but is not limited to conditions altering the growth of a cell or strain, exposure to mutagens, antibiotics, UV light, gamma-rays, x-rays, phage, macrophages, organic chemicals, inorganic chemicals, environmental pollutants, heavy metals, changes in temperature, changes in pH, conditions producing oxidative damage, DNA damage, anaerobiosis, depletion or addition of nutrients, addition of a growth inhibitor, and desiccation. Non-stressed cells are used for generation of "control" arrays and stressed cells are used to generate an "experimental", "stressed" or "induced" arrays.

In an alternate embodiment the present invention provides a method for quantitating the amount of each protein specifying RNA contained within an organism. This is often necessary in gene expression profile analysis because the quantity of transcript produced as well as its fold elevation is needed for quantitative analysis of the cell's physiological state. The method is applicable to both prokaryotic and eukaryotic organisms including for example, cyanobacteria (such as Rhodobacter and Synechocystis) yeasts (such as Saccharomyces, Zygosaccharomyces, Kluyveromyces, Candida, Hansenula, Debaryomyces, Mucor, Pichia and Torulopsis), filamentous fungi (such as Aspergillus and Arthrobotrys), plant cells and animal cells. The method proceeds by generating a comprehensive micro-array as described above, from either total or poly-adenylated RNA, depending on the whether the organism is prokaryotic or eukaryotic. Following the generation of the array, a set of labeled DNA and a set of labeled cDNA are synthesized having complementarity to the ORF's of the array. The signals generated from the independent hybridization of either the labeled DNA or cDNA are used to quantitate the amount of protein specifying RNA contained within a genome.

In another embodiment the invention provides a method for gene expression profiling with a reduced signal to noise ratio. This is accomplished using a dual "label swapping" method and is again applicable to both prokaryotic and eukaryotic genomes. "Label swapping" refers to a system where a set of probes or cDNA generated from control or experimental conditions are labeled with two different labels and mixed prior hybridization with the array. Two sets of control and experimental probes or cDNA's are generated. One of the control sets is labeled with a first label (i.e. cy3) and the other is labeled with a different second label (i.e. cy5). The two differently labeled sets are mixed and then hybridized with the array. The same process is repeated for the experimental conditions and the resulting control and experimental fluorescent signals are compared. This combination of signals provides (a) additional measure of each transcript level and (b) allows for the canceling of any bias associate with differential incorporation of fluorescently labeled nucleotide into cDNA or the hybridization of that cDNA.

The preferred embodiments of the invention are discussed below.

Bulk *E. coli* RNA was reverse transcribed to prepare hybridization probes. Despite the large amount of stable RNA (ribosomal and transfer RNAs) in the template, hybridization to protein-encoding genes was readily detected.

As shown in FIG. 1 with IPTG induction, conditions have been optimized to yield highly reliable data. In FIG. 1, basal expression levels were plotted on the ordinate, induced levels on the abscissa. Panel A illustrates the results obtained when two Cy3-labeled probes were hybridized to duplicate whole genome array sets. Panel B represents an experiment in which the Cy5-labeled cDNA copy of control RNA and the Cy3-labeled copy of induced RNA were co-annealed to a single slide set. The RNAs used to generate the results in Panel B were each labeled with the other dye to allow a "reciprocal" hybridization. In Panel C, the resulting data were averaged with the data presented in Panel B to yield the scatter plot depicted in Panel C. A second independent set of RNA samples were isolated, their cDNAs labeled with both dyes and products hybridized in both possible combinations to generate the results depicted in Panel D. Panel E displays the averaged results of the two independent experiments depicted in Panels C and D.

Reciprocal Labeling. When the results of a single hybridization experiment using different slide sets as capture reagents for Cy3-labeled cDNA derived from treated and control cells were plotted in log-log form, lacZYA induction above the background was detected (FIG. 1A); variation of other genes was also significant as indicated by the width of the points falling along the diagonal of this scatter plot. Improvements were observed by labeling the control sample with Cy5 and the induced sample with Cy3 before hybridizing to a single set of 3 slides (FIG. 1B). However, there was a skewing of the data away from the abscissa and towards the ordinate (y-axis; Cy5-labeled probe). Averaging of these results with others obtained using reciprocal copying of the same RNA samples (induced RNA reverse transcribed with Cy5 and control RNA with Cy3) resulted in a decreased variation between the treated and control samples (FIG. 1C). Such "label swapping" lessened the skewing and decreased the scatter. The experiment, depicted in FIG. 1C, was replicated; fresh cultures were induced and nucleic acids processed to yield the data depicted in FIG. 1D. The experiments shown in FIGS. 1C and 1D each represent four measurements of individual transcript abundance; this repetition and averaging yielded the tight constellation shown in FIG. 1E which combined the data of FIGS. 1C and 1D. Nonetheless, the scatter plot resulting from an experiment using the optimized protocol (FIG. 1E) illustrated that measurements of gene expression were still subject to considerable variation when the signal was in the lowest part of the detectable range.

The effect of 1 mM IPTG upon expression of the arrayed genes was investigated. Duplicate RNA preparations of the control and IPTG treated cells were each labeled with Cy3 and Cy5 by first strand cDNA synthesis. Averaging of measurements gave an optimal reliability of the data (FIG. 1). Examination of the extent of hybridization to any individual gene revealed a wide dynamic range with more than a thousand fold variation in signal intensity between genes (see FIG. 1). The expression of only 8 genes increased by a factor of more than 2 after exposure to 1 mM IPTG for 15 min (FIG. 1E). These induced genes are listed in Table 1. Two-fold or greater repression was not observed after this treatment. The most highly induced RNAs corresponded to the lac operon structural genes. Examples of the induced genes are b0956, melA, uxaA and b1783.

Signal Quantitation. The present invention was applied to monitor the effects of growth stage and medium on gene expression. For these embodiments, signal quantitation was important. The percentage of RNA that programs protein synthesis has been determined under a wide variety of growth regimes (Bremer and Dennis, *Escherichia coli and Salmonella: Cellular and Molecular Biology* ASM Press: 922–937 (1996)). The fraction of those protein-specifying transcripts devoted to each arrayed gene was estimated. Hybridization signals arising from annealing of RNA-derived Cy3-labeled cDNA populations were quantitated by dividing by the signal generated using Cy3 fluorescent DNA arising from copying of sheared *E. coli* genomic DNA as a probe. The probe synthesized by copying genomic DNA was used to approximate equimolar transcription of the entire genome. This quantitation allowed calculation of mRNA inventories. Three RNA samples were measured. The samples were isolated from cells growing exponentially in rich medium, from cells growing exponentially in minimal medium, and from cells in minimal medium transitioning from exponential to stationary phase. RNAs from certain central metabolic (gapA, ptsH), defense (ahpC, cspC), DNA metabolic (hns), surface structure (acpP, ompACFT, lpp), translation (rplBCKLMPWX, rpmBCI, rpsACDHJNS, trmD, fusA, infC, tufAB), transcription (rpoAB), and unassigned (b4243) genes (Riley and Labedan, *Escherichia coli and Salmonella: Cellular and Molecular Biology*, ASM press: 2118–2202 (1996)) were abundant (>0.1%, among the top 100 transcripts) in all three samples.

The most highly transcribed genes in actively growing broth-cultured cells often encoded proteins involved in translation. In contrast, cultures at a similar growth stage in glucose minimal medium, expressed to a very high level several small molecule biosynthetic genes and the means to utilize glucose. Thus, an agreement between these molecular analyses and the accumulated understanding of *E. coli* physiology was observed (*Escherichia coli and Salmonella: Cellular and Molecular Biology*, ASM press). This agreement was underscored in the analysis of cells transitioning from the exponential growth phase; the elevated expression of several rpoS-controlled genes corresponded to expectations (*Escherichia coli and Salmonella: Cellular and Molecular Biology*, ASM press).

The genes, each representing between 0.0007% and 1% of the hybridizing signal, were expressed in LB grown cells. The distribution of genes as a function of expression level is plotted in FIG. 2. FIG. 3 depicts fractional expression as a function of summed genes with genes ranked by expression level. In FIG. 2, the histogram plots the number of genes as a function of expression range. Diagonally striped, solid, and horizontally striped bars reflect distributions observed in RNAs derived from cells growing exponentially in minimal medium, cells transitioning to stationary phase in minimal medium, and cells growing exponentially in rich medium, respectively. In FIG. 3, the fraction (summed open reading frame transcripts/total open reading frame transcripts) was plotted as a function of genes summed. The order in which genes were summed was based upon expression level with the most highly expressed gene summed first.

Fewer genes were expressed in LB than in minimal medium (FIG. 2); the fraction of rare transcripts appeared under-represented in LB medium (FIG. 3). The fifty most highly expressed genes in broth-grown cells are listed in left-most columns of Table 2; twenty-six of these intensely transcribed genes encode proteins involved in translation while three encode chaperones.

The broad distribution analyses (FIGS. 2 and 3) readily revealed the significant differences observed in expression of *E. coli* when grown in defined and rich media. In minimal media many more genes were transcribed over a somewhat broader range. The 50 genes most highly expressed in exponentially growing cells cultured in minimal medium with glucose as a carbon/energy source are listed in the middle columns of Table 2. Eight biosynthetic genes were highly expressed (Table 2). Notable among them were metE, encoding the aerobic methionine synthase, and ilvC, an isoleucine-valine biosynthetic gene subject to feed-forward transcriptional activation (Umbarger, H. E, *Escherichia coli and Salmonella: Cellular and Molecular Biology*, ASM Press (1996)) by its substrates. Both the ilvC-encoded enzyme (Petersen et al., *Nucleic Acids Res.* 14:9631–9651 (1986)) and metE-encoded enzyme (Green, R. C., *Escherichia coli and Salmonella: Cellular and Molecular Biology*, ASM Press (1996)) are sluggish catalysts. The metE product accounts for about 5% of *E. coli* protein when cells are cultured in minimal medium with glucose as a carbon/energy source (VanBogelen et al., *Escherichia coli and Salmonella: Cellular and Molecular Biology*, ASM Press (1996)). Other highly expressed biosynthetic genes included folE and cysK; the folE product, GTP cyclohydrolase I catalyzes both cleavage of the 5-membered ring of guanine and the rearrangement of the ribose moiety of the substrate, GTP (Green et al., *Escherichia coli and Salmonella: Cellular and Molecular Biology*, ASM Press (1996)). cysK, encoding o-acetylserine(thiol)-lyase isozyme A, is responsible for more than 90% of sulfur fixation under aerobic conditions (Kredich, N. M., Molecular Biology, ASM press (1996)). Transcripts of the pyrBI operon encoding aspartate transcarbamylase also were highly expressed during exponential growth in minimal medium relative to a broth-grown culture. This expression level is a characteristic signature of strain MG1655 whose aspartate transcarbamylase content is elevated more than 100 fold when grown in the absence of uracil due to an rph mutation that is polar on pyrE (Jensen, K. F., *J. Bacteriol.* 181:3525–3535 (1993)). The other highly expressed transcripts, thrL and pheF, encoded, respectively, the threonine leader polypeptide (Landick et al., *Escherichia coli and Salmonella: Cellular and Molecular Biology*, ASM Press (1996)) and the phenylalanine-inhibited first enzyme of the common aromatic pathway. The pheF product, one of three isozymes, is estimated to account for more than 80% of the activity catalyzing the first common step of aromatic amino acid synthesis (Pittard, A. J., *Escherichia coli and Salmonella: Cellular and Molecular Biology*, ASM Press (1996)).

In this embodiment, expression of several genes catalyzing fueling reactions was also elevated. Unexpectedly, aceAB, encoding the glyoxylate shunt enzymes malate synthase and isocitrate lyase (Cronan and Laporte, *Escherichia coli and Salmonella: Cellular and Molecular Biology*, ASM Press (1996)), was highly expressed. Perhaps the TCA cycle functions in its branched state during this phase of growth requiring the glyoxylate shunt for anapleurotic replenishment (Neidhardt et al., *Physiology of the Bacterial Cell: A Molecular Approach*, Sinauer Associates, Inc. (1990)). As expected, ptsHI transcripts encoding phosphotransferase sugar transport common components (Postma et al., *Escherichia coli and Salmonella: Cellular and Molecular Biology*, ASM Press (1996)) also accumulated to a very high titer in glucose-minimal medium.

The present invention was applied to monitor the transcripts of cells transitioning from exponential to stationary phase in defined, minimal medium. During this transition, significant changes in gene expression were expected and observed. Expressed gene levels were from 0.0023 to 1.6%. A total of 1030 genes, of which 110 have a defined role, did not appear to be expressed. In this embodiment, the 50 most highly expressed genes during this transition are listed in the rightmost columns of Table 2. Significantly, several rpoS-regulated genes (Hengge-Aronis, *Escherichia coli and Salmonella: Cellular and Molecular Biology*, ASM press, 1497–1512) including hdeA (11 fold), hdeB (8.9 fold), dps (4.4 fold), gadA (8.2 fold) and gadB (12 fold) (Castanie-Cornet et al., *J. Bacteriol.* 181:3525–3535 (1999)) as well as rpoS (2.6 fold) itself became quite highly expressed. Despite this remodeling of transcription, the overall patterns of gene number as a function of expression level (FIG. 2) and fractional expression as a function of ranked gene (FIG. 3) were not as distinct as might have been expected in comparison to the patterns observed for RNA extracted from exponentially growing cells.

The observed expression patterns are summarized in Table 3 where gene products were grouped by metabolic function using an established classification scheme (Riley and Labedan, *Escherichia coli and Salmonella: Cellular and Molecular Biology*, ASM Press (1996)). Exponential growth in minimal medium elevated the amount of pyrimidine and amino acid biosynthetic transcripts. In contrast cofactor and purine transcripts did not appear to accumulate relative to growth in broth. Expression of glyoxylate shunt and miscellaneous glucose transcripts was also elevated in minimal medium; the seven-fold elevation of glyoxylate shunt transcripts exceeded the average of that observed for amino acid biosynthetic mRNAs. Expression of genes involved in sulfur fixation was also elevated during growth in minimal medium.

The rapid growth observed in LB was reflected in the gene expression profile, as was the difference in carbon energy/source between glucose and amino acids. LB-grown cultures displayed elevated expression of genes specifying glucogenic enzymes and of genes whose products degrade small molecules. Expression of the ATP and proton motive force generating machinery, elevated by a factor of about 2, paralleled increased ribosomal protein, aminoacayl-tRNA synthetase and foldase/usher expression.

Changes observed upon entering the transitional period between exponential and stationary phase growth were less dramatic. Nonetheless, elevation of mRNAs specifying gluconogenic, glycolytic, and TCA cycle enzymes was observed as was an increase in transcripts-encoding enzymes responsible for metabolic pool interconversions and for the non-oxidative branch of the hexose monophosphate shunt. The cells also displayed an increased titer of foldase/usher-specifying and global regulatory function transcripts while transitioning between growth phases.

The present invention was used to monitor the change in gene expression when cells overexpressd sdiA gene. The sdiA is a positive activator of an operon that includes ftsQAZ, genes essential for septation.

RNA isolated from broth grown, exponential phase cultures harboring either a single copy (pUC19/RFM443) or many copies (PDEW140/RFM443) of sdiA were compared after conversion into fluorescently labeled cDNA by hybridization to individual genes arrayed on glass slides.

Expression of about 9% of the *E. coli* genes was elevated in the strain containing the multicopy sdiA plasmid (Table 4). Transcripts of seven genes involved in cell division were raised 2.1 to 11 fold by amplification of sdiA as were a large number (about 20) of genes involved in DNA replication, repair, and degradation. Transcript levels of eight genes whose products alter the susceptibility of *E. coli* to drugs were more highly expressed in the strain containing the gene amplification. This genetic configuration also resulted in elevated expression of several lipopolysaccharide biosynthetic genes (rfa) as well as open reading frames encoding membrane structural elements.

Expression of several genes of unknown function was also elevated in response to the presence of multiple copies of sdiA. The genes whose transcripts were highly (>6 fold) elevated in response to the multicopy sdiA plasmid included: b0135 (6.4 fold, annotated as putative fimbrial-like protein gene), b0225 (6.4 fold, a gene apparently co-transcribed with dinJ since between them there is only a 3 base pair intergenic region), b0157 (11 fold, encoding a putative malate dehydrogenase), b0530 (also known as sfmA and predicted to specify a fimbrial like protein was elevated 6.5 fold), b0712 (encoding a putative carboxylase had a 6.4 fold increase in transcript content) and b1438 (11 fold elevation in expression).

Around 3% of the *E. coli* genes were repressed in a strain harboring the sdiA plasmid relative to the control strain containing the vector (Table 5). The genes involved in chemotaxis, mobility, and flagella biosynthesis were repressed dramatically. Genes for transport of certain carbohydrate substrates and cations ($Fe^{++}$ and $K^+$), degradation of corresponding carbon compounds, as well as acetate fermentation were repressed. The presence of pDEW140, a pUC19 derivative harboring sdiA, resulted in a 30-fold elevation in detectable sdiA transcript. Expression of sdiA was very low (0.0015%, the 4212th most abundant transcript) in LB grown *E. coli* MG1655. The increased expression in the plasmid containing strain raised the transcript rank to about 300.

Genes ddl, ftsQ, ftsA, ftsZ and lpxC are organized in the order mentioned above in the complex ftsZ containing operon, and the above genes are transcribed in the same direction starting with ddl. Since the sdiA-encoded positive activator drives transcription of a mRNA including ddl, ftsQ, ftsA, ftsZ, and lpxC, increased quantities of RNA hybridizing to these genes were expected. Amplification of sdiA due to its presence on a multicopy plasmid elevated expression of ddl, ftsQ, ftsA, ftsZ and lpxC 4.6, 8.8, 10, 11 and 3.5 fold, respectively, relative to the strain that harbored pUC19 (Table 4).

In the immediate down stream of sdiA, there are yecF, followed by uvrY and uvrC gene, respectively. uvrY and uvrC genes are transribed in the same direction as sdiA and the yecF is transcribed in the opposite direction. Unexpectedly, amplification of sdiA elevated expression of two genes downstream of sdiA was observed. uvrY expression was elevated 12 fold while uvrC transcription was increased by a factor of 9 (Table 4). These two genes were transcribed in the same direction as sdiA. The expression of yecF decreased only slightly.

Amplification of sdiA caused the expression of 101 genes to fall by a factor of 2 or more. Among them, 44 were involved in motility and chemotaxis. Thirty four genes were down regulated more than five-fold by sdiA amplification. Of these, thirty were involved in chemotaxis or motility (cheW; flgB,C,D,E,F,G.H,I,J,K,L,M,N; fliA,C,E,F,G,H,J,L, M,N,P,S,T,Z; tar and tsr). The master regulator genes flhC and D controlling flagella operon expression were lowered by only 30–38%.

The swarming of strains having single or multiple copies of sdiA was examined by spotting four single colony isolates of each strain on semi-solid medium. Since almost all the genes involved in flagella biosynthesis, chemotaxis and motility were dramatically repressed in the sdiA overexpression strain, loss of mobility of the sdiA overexpression strain was predicted. Experiments were carried out to compare the mobility of the two strains. After 8 hr. at 37° C., the strain containing pUC19 had swarmed (diameter=32±2.5 mm) while that containing pDEW140 (sdiA$^+$) had not (diameter= 3.2±0.4 mm). After 23 h the pUC19 containing strain had filled the petri plate while the strain carrying the sdiA amplification had significantly swarmed covering about one half of each plate. This partial phenotype could be explained by either (a) plasmid loss allowing swarming of a revertant (sdiA$^+$ haploid) population as ampicillin was exhausted from the medium or (b) sdiA amplification only partially compromising motility. To distinguish between these possibilities, the site of inoculation and the edge of the swarm after 23 hr were streaked for single colonies to an ampicillin containing LB agar plate. Massive sdiA$^+$ plasmid loss from cells at the edge of the swarm was not observed suggesting that the motility defective phenotype was not an absolute one.

If the role of sdiA is to stimulate gene expression required for septation, sdiA might coordinate expression of the ftsZ-containing operon with action at the origin of replication, oriC. The two genes immediately flanking oriC are mioC and gidA. mioC is followed by asnC and asnA, and gidA is followed by gidB, atpI and atpB. All of the genes except asnA are transcribed in the same direction. gidA and mioC were over-transcribed relative to the vector-containing control strain. mioC transcript content was elevated 7 fold while those of the gidA and gidB genes were elevated 4 and 2 fold, respectively. This effect was most localized; adjoining genes were not over-expressed.

Having found enhanced action around oriC, it was reasonable to examine the transcript content of genes surrounding the termini of replication when sdiA was amplified. There are multiple termini in *E. coli*. The region surrounding terB spans minutes 35.3–37.3 (Berlyn et al., *Escherichia coli and Salmonella: Cellular and Molecular Biology* ASM Press: 922–937 (1996)) sdiA amplification-elevated expression of 12 of the 88 genes:in this region more than 3 fold. Transcripts from another 26 genes in the region were elevated by a factor of 1.5 to 3. Unlike the action observed around the terminus, the stimulation seen in the vicinity of terB was diffuse. Interestingly, tau, encoding the terminus-utilizing factor, was not over-expressed. Transcription of gusR, located at 36.5 minutes, was elevated 8 fold by sdiA amplification (Table 4).

acr genes specify sensitivity to acriflavines, molecules that intercalate into double stranded DNA containing monotonic runs of base pairs. Most acr mutants display a defect in acridine efflux; moreover they are often pleiotropic being hypersensitive to a wide variety of chemicals. Thus hyperexpression of these genes in a strain harboring an sdiA-bearing multicopy plasmid could lead to mitomycin C expulsion and the observed resistance to this DNA damaging agent. This expectation of acr hyper-expression was confirmed. Evidence for elevated expression of each acr operon was found as indicated by the fold expression reported in Table 4.

Elevated transcription of the gal operon genes at minute 17 was observed in the strain bearing the sdiA amplification. These genes, moderately expressed when strain MG1655 was grown in LB medium (ranks: galE 841, galT 1512, galK 599; Wei and LaRossa, unpublished), were elevated 3.8, 4.9 and 4.1 fold, respectively. Nearby, at minute 16 is the ybgIJKL-nei region. ybg genes are organized as ybg F, ybgJ, ybgK and ybgL, in that order followed by nei gene. These genes, transcribed in the same orientation, could constitute an operon since the open reading frames are densely packed, at times overlapping. sdiA amplification elevated expression of these genes 5.2, 4.7, 6.4, 3.8 and 8.6 fold, respectively. nei encodes an endonuclease responsible for the excision of oxidized pyrimidines in the double helix.

Two linked genes at minute 44, b1956 and b1957 were elevated 6.6 and 14 fold by sdiA amplification. Similarly, expression of b2017 and b2016, two genes at minute 45 divergently transcribed from and adjacent to the his operon, was elevated 3.8 and 3.5 fold, respectively by the presence of the sdiA-containing multicopy plasmid.

Mitomycin C (MMC) is a DNA damaging agent. *E. coli* strain, MG1655, was exposed to MMC, and gene expressions were compared in cells that were harvested at15 and 40 min post exposure. In the cells that were harvested at 15 min, very little SOS response was detected. At the 40 min, expression of 40 genes was elevated greater than 2 fold relative to the control strain. Among the 40, 13 stress response genes were induced (Table 6) more than 2 fold. The SOS genes that were induced by a 40 min exposure to MMC were recN, dinI, sulA, lexA, recA, uvrA, dinD, priC, umuC, mioC, uvrB, ruvA, and xseA.

The SOS responsive genes are lexA-dependent. In order to determine the gene expression patterns in the presence and the absence of the SOS response, DM800 and DM803 were exposed to MMC for 40 min and the gene expression profiles were compared. DM800 and DM803 harbor lexA$^+$ and lexA$^{ind}$ alleles, respectively. As expected, when exposed to MMC for 40 min, SOS responsive genes were induced greater than 2 fold in DM800 strain. SOS responsive genes, including lexA, were not induced in the DM803 strain (Tables 7 and 8). Many genes that were not induced by MMC in DM800 were induced by the DNA damaging agent in DM803. For examples, the expression of the following genes were induced greater than 2 fold in DM803 but not in DM800 (Tables 7 and 8): among the induced genes are those involved with cell division (i.e., dicB, dicC, and sdiA); chemotaxis and mobility (i.e., cheW and motA); and the transport of small molecules (i.e., cycA, fadL, chaC, codB and btuC).

The present invention is not limited to only highly expressed genes for several reasons. First, reproducible expression measurements were obtained over a wide dynamic range (FIG. 1E). Second, the data of FIG. 3 and Table 1 illustrate that the lac operon expression, although low before IPTG induction, was detected suggesting that most transcripts can be readily measured with the described techniques. Analyses of well-characterized "promoter-down" mutants or spiking experiments may be useful in defining the lower limits of expression that can be observed.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

The meaning of abbreviations is as follows: "hr" means hour(s), "min" means minute(s), "sec" means second(s), "d" means day(s), "mL" means milliliter(s), "µL" means microliter(s), "nL" means nanoliter(s), "µg" means microgram(s), "ng" means nanogram(s), "mM" means millimole(s), "µM" means micromole(s).

Media and Culture Conditions

Materials and methods suitable for the maintenance and growth of bacterial cultures were found in *Experiments in Molecular Genetics* (Jeffrey H. Miller), Cold spring Harbor Laboratory Press (1972), *Manual of Methods for General Bacteriology* (Phillip Gerhardt, R. G. E. Murray, Ralph N. Costilow, Eugene W. Nester, Willis A. Wood, Noel R. Krieg and G. Briggs Phillips, eds), pp. 210–213, American Society for Microbiology, Washington, D.C. or Thomas D. Brock in *Biotechnology: A Textbook of Industrial Microbiology*, Second Edition (1989) Sinauer Associates, Inc., Sunderland Mass. All reagents and materials used for the growth and maintenance of bacterial cells were obtained from Aldrich Chemicals (Milwaukee, Wis.), DIFCO Laboraoties (Detroit, Mich.), Gibco/BRL (Gaithersburg, Md.), or Sigma Chemical Company (St. Louis, Mo.) unless otherwise specified.

LB medium contains following per liter of medium: Bacto-tryptone (10 g), Bacto-yeast extract (5 g), and NaCl (10 g).

Minimal M9 medium contains following per liter of medium: $Na_2HPO_4$ (6 g), $KH_2PO_4$ (3 g), NaCl (0.5 g), and $NH_4Cl$ (1 g).

Above media were autoclaved for sterilization then 10 mL of 0.01 M $CaCl_2$ and 1 mL of $MgSO_4$. $7H_2O$ plus carbon source and other nutrient were added as mentioned in the examples. All additions were pre-sterilized before they were added to the media.

Molecular Biology Techniques

Restriction enzyme digestions, ligations, transformations, and methods for agarose gel electrophoresis were performed as described in Sambrook, J., et al., *Molecular Cloning: A Laboratory Manual*, Second Edition, Cold Spring Harbor Laboratory Press (1989). Polymerase Chain Reactions (PCR) techniques were found in White, B., *PCR Protocols: Current Methods and Applications*, Volume 15(1993) Humana Press Inc.

Example 1

Example 1 demonstrates genomic DNA amplification and the preparation of the high density DNA array.

Amplification of 4290 *E. coli* genes Specific primer pairs (available from Sigma Genosys Biotechnolgies, The Woodlands, TX.) for each protein-specifying gene of *E. coli* were used in two consecutive PCR amplification reactions. Genomic DNA (30 ng) was used as the template in the first round of PCR amplification, and 500-fold diluted PCR products served as templates for PCR re-amplification. Duplicate 50 µL scale reactions were performed. The PCR reactions were catalyzed with ExTaq™ polymerase (Panvera, Madison, Wis.) with the four dNTPs (Pharmacia), present at 0.25 mM and the primers at 0.5 µM. Twenty-five cycles of denaturation at 95° C. for 30 sec, annealing at 64° C. for 30 sec and polymerization at 72° C. for 2 min were conducted. A 2 µL aliquot of each PCR product was sized by electrophoresis through agarose gels. More than 95% of the second round PCR products displayed visible bands of the correct size. Second round PCR reactions devoid of templates and primers were saved to serve as negative controls for hybridization capture reagents. One third of each second round PCR reaction was purified using 96-well PCR purification kits (Qiagen, Valencia, Calif.). The eluted DNAs were dried using a vacuum centrifuge.

Arraying amplified genes. Twenty microliters of 6M $Na_2SCN$ or 50% DMSO was added to each dried DNA sample ($\geq 0.1$ ng/nL). A generation II DNA spotter (Molecular Dynamics, Sunnyvale, Calif.) was used to array the samples onto coated glass slides (Amersham Pharmacia Biotech, Arlington Heights, Ill.). Aliquots of approximately 1 nL from 1536 resuspended PCR products were arrayed in duplicate on each slide; a set of three slides supported all amplified *E. coli* genes. To serve as controls, 76 specific *E. coli* PCR products, 8 amplified genes of *Klebsiella pnuemoniae* and 12 plant cDNA clones were also spotted onto each slide. Spotted glass slides, after baking at 80° C. for 2 hr., were stored under vacuum in a desiccator at room temperature.

Example 2

Example 2 demonstrates gene expression analysis. *E. coli* mRNA was isolated, fluorescent labeled cDNA was prepared using mRNA as a template, and the labeled cDNA was hybridized to the high density DNA array. The amount of DNA hybridized to DNA array was quantitated and analyzed.

Microbiological Methods

*E. coli* MG1655 was cultured with aeration in either the minimal medium, M9 (Miller, J. H., *Experiments in Molecular Genetics*, Cold Spring Harbor (1972)), supplemented with 0.4% glucose or in the rich medium, LB (Miller, J. H., *Experiments in Molecular Genetics*, Cold Spring Harbor (1972)), at 37° C. The overnight culture was diluted 250 fold into fresh medium and aerated by shaking at 37° C. Samples of the minimal medium culture were harvested at $A_{600}=0.40$ (exponential phase) and 1.6 (transition to stationary phase) prior to RNA isolation. An IPTG induction (Miller, J. H., *Experiments in Molecular Genetics*, Cold Spring Harbor (1972)) was performed to examine the specificity with which it effects gene expression. A culture grown overnight in LB at 37° C. was diluted 250 fold into fresh LB and aerated at 37° C. When the culture achieved an appropriate density ($A_{600}=0.40$), it was split. To one portion was added IPTG to a final concentration of 1 mM; the untreated sample served as a control. Incubation of both samples was continued with aeration at 37° C. for another 15 min ($A_{600}$=0.45 for both cultures) before RNA isolation was initiated.

RNA Isolation. An equivalent volume of shaved ice was added to 50 mL samples which were pelleted immediately in a refrigerated centrifuge by spinning at 10,410×g for 2 min. Each resultant pellet was resuspended in a mixture containing 100 μL of Tris HCl (10 mM, pH 8.0) and 350 μL of β-mercaptoethanol supplemented RLT buffer [Qiagen RNeasy Mini Kit, Valencia, Calif.]. The cell suspension was added to a chilled 2 mL screwed-capped microfuge tube containing 100 μL of 0.1 mm zirconia/silica beads (Biospec Product Inc., Bartlesville, Okla.). The cells were broken by agitation at room temperature for 25 sec with a Mini-Beadbeater™ (Biospec Products Inc., Bartlesville, Okla.). Debris was pelleted by centrifugation for 3 min at 16,000×g and 4° C.; the resultant supernatant was mixed with 250 μL of ethanol. This mixture was loaded onto a column from the Qiagen RNeasy Mini Kit. RNA isolation was completed using the protocol supplied with this kit. Incubation for 1 hr. at 37° C. in 40 mM Tris pH 8.0, 10 mM NaCl, 6 mM $MgCl_2$ with RNase free RQ1 DNase (1 unit/μL, Promega, Madison, Wis.) digested any genomic DNA contaminating the RNA preparation. The digestion products were purified by a second passage through the RNeasy protocol (Qiagen, Valencia, Calif.). The product was eluted from the column in 50 μL RNAse-free water prior to determining sample concentration by an $A_{260}$ reading. RNA preparations were stored frozen at either −20 or −80° C.

Synthesis of fluorescent cDNA from total RNA. Six microgram of RNA template and 12 μg of random hexamer primers (Operon Technologies, Inc., Alameda, Calif.) were diluted with double distilled (dd) water to a volume of 22 μL. Annealing was accomplished by incubation at 70° C. for 10 min followed by 10 min at room temperature. In order were added: 8 μL of 5×SuperScript II reaction buffer (Life Technologies, Inc., Gaithersberg, Md.), 4 μL of 0.1 M DTT, 2 μL of the dNTP mix (2 mM dATP, 2 mM dGTP, 2 mM TTP, 1 mM dCTP), 2 μL of 0.5 mM Cy3- or Cy5-dCTP (Amersham Pharmacia Biotech, Arlington Heights, Ill.), and 2 μL of SuperScript II reverse transcriptase (200 units/mL, Life Technologies Inc., Gaithersberg, Md.). DNA synthesis proceeded at 42° C. for 2.5 hr. before the reaction was terminated by heating at 94° C. for 5 min. Alkaline hydrolysis of the RNA templates was achieved by adding 2 μL of 5M NaOH followed by incubation at 37° C. for 10 min. Hydrolysis was terminated by the sequential addition of 3 μL of 5M HCl and 5 μL of 1M Tris-HCl, pH 6.8. The labeled cDNA was purified with a PCR purification kit (Qiagen, Valencia, Calif.), dried in a speed vacuum and stored at −20° C. Labeling efficiency was monitored using either $A_{550}$, for Cy3 incorporation, or $A_{650}$, for Cy5 labeling, to $A_{260}$ ratios.

Fluorescent labeling of genomic DNA. Genomic DNA, isolated from strain MG1655 (Bachmann, B., *Escherichia coli and Samonella: Cellular and Molecular Biology*, ASM Press (1996)) by standard procedures (Van Dyk and Rosson, *Methods in Molecular Biology: Bioluminescence Methods and Protocols*, Humana Press Inc. (1998)), was nebulized to approximately 2 kb pair fragments. Three microgram of this DNA was mixed with 6 μg of random hexamers primers (Operon Technologies, Inc., Alameda, Calif.) in 33 μL of dd water. DNA was denatured by heating at 94° C. prior to annealing on ice for 10 min. Fluorescent copying of the genomic DNA was accomplished using the Klenow fragment of DNA polymerase 1 (5 μg/μL, Promega, Madison, Wis.). To the DNA mixture was added 6 μL of 10×Klenow buffer (supplied with the enzyme), 3 μL of the dNTP mix described above, 12 μL dd $H_2O$, 3 μL of 0.5 mM Cy3-dCTP (Amersham Pharmacia Biotech, Arlington Heights, Ill.), and 3 μL of the Klenow fragment of DNA polymerase I. After a static, 2.5 h incubation at room temperature, the labeled DNA probe was purified using a PCR purification kit (Qiagen, Valencia, Calif.) before drying in a speed vacuum.

Hybridization and washing. Spotted slides were placed in isopropanol for 10 min, boiled in dd $H_2O$ for 5 min and dried by passage of ultra-clean $N_2$ gas prior to pre-hybridization. The prehybridization solution (PHS) was 3.5×SSC (BRL, Life Technologies Inc., Gaithersberg, Md.), 0.2% SDS (BRL, Life Technologies Inc., Gaithersberg, Md.), 1% bovine serum albumin (BSA, Fraction V, Sigma, St. Louis, Mo.). The hybridization solution (HS) contained 4 μL of dd water, 7.5 μL of 20×SSC, 2.5 μL of 1% SDS (BRL, Life Technologies Inc., Gaithersberg, Md.), 1 μL of 10 mg/ml Salmon sperm DNA (Sigma, St. Louis, Mo.) and 15 μL of formamide (Sigma, St. Louis, Mo.). The slides were incubated at 60° C. for 20 min in PHS. The slides were next rinsed 5 times in dd water at room temperature and twice in isopropanol before drying by the passage of nitrogen. The dried probe was resuspended in the HS and denatured by heating at 94° C. for 5 min. Thirty microliter of the probe-containing HS was applied to a dried, pre-hybridized slide, covered with a cover slip (Corning, Corning, N.Y.), and put into a sealed hybridization chamber containing a small reservoir of water to maintain moisture. Hybridization occurred for approximately 14 h at 35° C. Cover slips were removed in washing buffer I (WB I=2×SSC, 0.1% SDS) warmed to 35° C. prior to incubation for 5 min. Next, the slides were washed sequentially for 5 min in 1×SSC, 0.1% SDS and 0.1×SSC, 0.1% SDS. Slides were then passed through three baths, each passage lasting 2 min, 0.1×SSC. The slides were dried with a nitrogen gas flow.

Data Collection and Analysis. Hybridization to each slide was quantified with a confocal laser microscope (Molecular Dynamics, Sunnyvale, Calif.) whose photomultiplier tube was set to 700 volts and 800 volts for obtaining Cy3 and Cy5 signals respectively. The images were analyzed with Array Vision 4.0 software (Imaging Research, Inc., Ontario, Canada). The fluorescent intensity associated with each spotted gene was reduced by subtracting the fluorescence of an adjoining, non-spotted region of the slide. These readings were exported to a spreadsheet for further manipulation. The four "no DNA" spots derived from PCR reactions devoid of template were controls used to determine the noise (background signal) level.

The 96 genes present on each slide were used as internal controls to quantify signal intensities yielding equivalent readings among the three slides of a whole genome array set. This corrected for slide-to-slide signal variation.

For the IPTG induction experiment, it was presumed that the overall transcriptional pattern did not change significantly. Thus the summed equivalent reading for the entire genome was quantified; analogous quantitation of the underlying equivalent readings allowed calculation of fold induction of each gene's expression by comparison of such quantified equivalent readings.

RNA abundance. To convert normalized equivalent readings into measures of transcript abundance, a further correction was needed. That correction required the hybridization signal arising from an equimolar concentration of all transcripts. The surrogate for this transcript pool was the fluorescent copy of genomic DNA. Thus, the fluorescent intensities from hybridization with RNA-derived probes were corrected using fluorescent intensities arising from genomic DNA derived probes. Specifically, the abundance of each gene's transcription product(s) was determined by dividing the normalized equivalent reading of the genomic DNA derived sample into the normalized equivalent reading from the RNA derived sample. The convention of Riley (Riley and Labedan *Escherichia coli and Salmonella: Cellular and Molecular Biology ASM Press,* 1996)) was followed in grouping genes into functional sets.

Example 3

Example 3 demonstrates gene expression profile changes when cell were exposed to IPTG, or grown in different culture media. The results are illustrated in Tables 1,2 and 3 (Listing of Tables) as described above.

IPTG Induction An *E. coli* strain MG1655 was grown overnight in LB at 37° C. The culture was diluted 250 fold into fresh LB and aerated at 37° C. When the culture achieved an appropriate density ($A_{600}$=0.40) it was split into two portions.

To one portion, IPTG was added to a final concentration of 1 mM. The other portion was untreated and served as a control.

Both samples was incubated with aeration at 37° C. for another 15 min ($A_{600}$=0.45 for both cultures) before RNA isolation. Gene expression analysis was performed as described in Examples 1 and 2.

Cells were grown in different culture media *E. coli* MG1655 was cultured with aeration overnight in either the minimal medium, M9, supplemented with 0.4% glucose or in the rich medium, LB at 37° C. The overnight culture was diluted 250 fold into fresh medium and aerated by shaking at 37° C. Samples of the minimal medium culture were harvested at $A_{600}$=0.40 (exponential phase) and $A_{600}$=1.6 (transition to stationary phase) prior to RNA isolation. The LB culture was harvested at $A_{600}$=0.4 prior to RNA isolation. Gene expression analysis was performed as described in Examples 1 and 2.

Example 4

Example 4 demonstrates gene expression changes and the effect on mobility when sdiA gene was overexpressed in *E. coli*. The results are tabulated in Tables 4 and 5 (Listing of Tables) as described above.

The following plasmids and strains were used in this example.

| strain or plasmid | genotype |
|---|---|
| MG1655 | rph-1 |
| RFM443 | rpsL galK2 lacΔ74 |
| pUC19 | Cloning vector |
| pDEW140 | pUC19 + sdiA (EcoRI) |

Strains and Growth Conditions

Strains of MG1655 (Bachmann, B., *Escherichia coli and Samonella: Cellular and Molecular Biology,* ASM Press (1996)) and RFM443 (Menzel R., *Anal. Biochem.,* 181:40–50 (1989)) have been described.

pDEW140 was constructed as following: Chromosomal DNA isolated from *E. coli* W3110 was partially digested with restriction enzyme Sau3A1 and size fractionated on agarose gels. Fractions of two size ranges (average sizes of approximately 2.5 and 4.0 Kbp) were ligated to pBR322 (0.11 pmol) or pUC18 (0.11 pmol) that had previously been digested with restriction enzyme BamHI and treated with calf intestinal alkaline phosphatase. The molar ratio of chromosomal DNA to vector in each of the ligation reactions was approximately 0.2:1. The ligation products were used to transform ultracompetent *E. coli* XL2Blue (Stratagene) to ampicillin resistance. Pooled transformants (>$10^5$ for each transformation) were used to isolate plasmid DNA.

0.3 ng of the pUC18 library was electro-transformed into RFM443. The MMC resistant clones were selected on LB agar plates supplemented with 100 μg/mL of ampicillin and 6 mg/mL of MMC. Resistant colonies appeared after the incubation at 37° C. The colonies underwent single colony purification on the same medium. Plasmids derived from single colonies were isolated with the Qiagen 96-well turbo plasmid prep kit. These plasmids served as a template for primer-directed DNA sequencing of the insert ends. One of the plasmids, Plasmid p[3+4/B10], was shown by sequencing to carry the sdiA and surrounding genes. From this plasmid SdiA was amplified by PCR using the primers:

f primer=TGGCA CGCAG GACAG AA (SEQ ID NO:1)

d primer=TAACA AATCA GCATA ACTCA T (SEQ ID NO:2)

The PCR used Ampli-Taq Gold. Conditions were 94° C., 11 min followed by 32 cycles of 94° C. for 45 sec, 45° C. for 45 sec, 72° C. for 90 sec, the 72° C. for 7 min.

The PCR product was blunt end ligated into EcoRV digested pT7Blue-3 (Novagen). A clone having the proper sized fragment was obtained after transformation into DH5-alpha. From colonies, inserts of the proper size were detected by PCR-based analysis. Such colonies served as a source of plasmid DNA from which sdiA was liberated by digestion with EcoRI. The fragment was sized by electrophoresis through agarose gels and ligated into EcoRI digested pUC19. The ligation mixture was used to tranform DH5alpha. Plasmid preps of the transformants were sequenced. One such plasmid containing sdiA was named pDEW140 and transformed into strain RFM443.

Plasmids pUC19 and pDEW140 were transformed into RFM 443 selecting for ampicillin resistance on solidified LB agar medium.

Strains of RFM443 (pUC19) and RFM443 (pDEW140) were grown overnight with aeration in LB with 150 μg/mL ampicillin (LB with amp). The overnight culture was diluted 250 fold into fresh medium (LB with amp) and incubated further at 37° C. with shaking. Cells were collected at O.D.600=0.45, and total RNA was purified using Qiagen RNeasy mini.

Motility Experiment

A single colony was picked from freshly grown RFM443 (pUC19) or RFM443 (pDEW140) cultured on LB agar (1.2%), and the center of a LB with amp soft agar (0.3%) plate was stabbed. The soft agar plate containing each culture was incubated at 37° C. The diameters of the growth zones of the two strains were measured and compared.

Example 5

Example 5 demonstrates the differences in gene expression profile between strains proficient or deficient in their ability to respond to DNA damaging agents. An isogenic pair of strains, differing only in lexA, was used to investigate the cell's range of responses to the DNA damaging agent mitomycin C (MMC). The results are tabulated in Tables 6, 7, and 8 (Listing of Tables) as described above.

Strains *E. coli* strain, MG1655, was used to determine the gene expression profile of *E. coli* in response to a MMC challenge. Two isogenic *E. coli* strains (Mount et al, *J. Bacteriol.* 112:886–893 (1972)), DM800 (lexA⁺), used as control displaying a normal response to DNA damage, and DM803 (lexA$^{ind}$), a strain unable to mount the predominant "SOS" response to DNA damage, were compared using comprehensive gene expression profiling.

MMC experiment MG1655 cells were grown in LB overnight with aeration. The overnight cultures were diluted 100 fold in LB to final volume of 500 mL and grown at 37° C. to exponential phase. 200 mL of culture was treated with MMC to the final concentration of 250 ng/mL. Another 200 mL of culture were mock treated without MMC for comparison. Cells were harvested at 15 min and 40 min for MG1655 strain. With DM800 and DM803 stains, cells, cultured in an identical manner, were harvested after 40 min exposure. RNA was isolated and gene expression profile was analyzed as shown in Examples 1 and 2. As seen in Tables 7 and 8, the lexA allele has a great influence on the response of cells to MMC. Table 8 shows that the strain deficient in SOS response still response to MMC but in different manner.

Example 6

Preparation of a Synechocystis sp. PCC6803 cDNA Probes

This example describes the construction of Synechocystis sp. PCC6803 cDNA probes following growth of the cells in either minimal growth media (control) or minimal media plus UV-B light treatment. The prepared cDNA probes are used to determine gene expression patterns of many genes simultaneously on a Synechocystis sp. PCC6803 DNA microarray as described in Examples 7 and 8 below.
Hybridization of Microarray Slides and Quantitation of Gene Expression Microarray glass slides were treated with isopropanol for 10 min, boiling double distilled water for 5 min, then treated with blocking buffer (3.5×SSC, 0.2% SDS, 1% BSA) for 20 min at 60° C., rinsed five times with double distilled water, then twice with isopropanol, followed by drying under nitrogen. Cy3 labeled cDNA probes prepared from the total RNA of the UV-B treated Synechocystis culture, mixed with an equal amount of Cy5 labeled cDNA probes prepared from the total RNA of the untreated Synechocystis culture, were applied to the glass slide in a total volume of 30 µL. The hybridization was repeated using Cy5 labeled cDNA probes prepared from total RNA of UV-B treated Synechocystis culture mixed with an equal amount of Cy3 labeled cDNA probes prepared from the total RNA of the untreated culture, and applied to a second glass slide in a total volume of 30 µL. The hybridization reactions on the glass slides were performed for 16 hr at 42° C., in a humidified chamber. Hybridized slides were washed in 1×SSC (0.15 M NaCl, 0.015 M sodium citrate), 0.1% SDS for 5 min at 42° C.; 0.1×SSC, 0.1% SDS for 5 min at 42° C.; three washes in 0.1×SSC for 2 min at room temperature; rinsed with double distilled water and isopropanol; and dried under nitrogen. The slides were scanned using a Molecular Dynamics laser scanner for imaging of Cy3 and Cy5 labeled cDNA probes. The images were analyzed using Array Vision Software (Molecular Dynamics, Imaging Research) to obtain fluorescence signal intensities of each spot (each ORF on the array) to quantitate gene expression. The ratio between the signals in the two channels (red:green) is calculated and the relative intensity of Cy5/Cy3 probes for each spot represents the relative abundance of specific mRNAs in each sample.
Synechocystis Strain and Culture Methods Briefly, Synechocystis sp. PCC6803 cells were grown at 30 µES-$^1$m-$^2$ light intensity in a minimal growth media, BG-11 (Catalog # C-3061, Sigma Chemical Co., St. Louis, Mo.) at 30° C., with shaking at 100 rpm with 5% $CO_2$. Fifty milliliters of Synechocystis cells grown to mid logarithmic phase ($OD_{730\ nm}$=0.8 to 1.0) were divided into two 25 mL cultures and transferred from the Erlenmeyer growth flask to two 100 mL petri dishes. The petri dishes, with the lids on, were placed on a rotary shaker and shaken at 100 rpm.
Cell Treatments For the control, the petri dishes comprising the Synechocystis cells were placed on a rotary shaker with the lids on, and shaken at 100 rpm. For the UV-B treated group, the petri dishes comprising the Synechocystis cells were placed on a rotary shaker with the lids on, and shaken at 100 rpm. A UV-B lamp (302 nm,) was positioned above the petri dishes and the distance between the UV-B light source and the petri dishes was adjusted to give the desired level of UV-B light intensity. The level of UV-B light intensity was measured at the surface of the cell culture using a UV light meter, following the manufacturer's instructions. UV-B treatment was performed for either 20 min or 120 min. Following UV-B irradiation, the cells were immediately cooled on ice and their RNA isolated as described below.
Total RNA Isolation and cDNA Probe Synthesis Control-treated Synechocystis cells and UV-B treated Synechocystis cells were cooled rapidly on ice and centrifuged at 4000 rpm for 5 min. Total RNA samples were isolated using Qiagen RNeasy Mini Kit (Qiagen), following the manufacturer's protocol. RNase A digestion was performed as described in the protocol, and a second round purification was performed using the RNeasy Mini Kit. The purified total RNA was analyzed by agarose gel electrophoresis.

From each total RNA preparation, both Cy3 and Cy5 florescent dye labeled cDNA probes were prepared. To synthesize the Cy3 or Cy5 labeled cDNA probes, a reverse transcription reaction was performed using 10 µg total RNA, 12 µg random hexamer (Ambion), 50 µM of dATP, dGTP, dTTP, 25 µM of dCTP, and 15 µM Cy3-dCTP or 22 µM Cy5-dCTP (Amersham Pharmacia Biotech), DTT, and AMV reverse transcriptase (Gibco BRL). The reaction was carried out at 42° C. for 2.5 hr. After the labeling reaction, RNA templates were degraded by alkaline hydrolysis and the cDNA probes were purified using Qiagen PCR purification kit. The purified probes were quantitated by measuring the absorbance at 260 nm, 550 nm (Cy5 dye incorporation) and 650 nm (Cy3 dye incorporation). Prior to hybridization, 100–200 pmol of the purified Cy3 or Cy5 labeled cDNA probes were dried under vacuum, and re-dissolved in the hybridization buffer (5×SSC, 50% formamide, 0.1% SDS, and 0.03 mg/mL salmon sperm DNA).

Example 7

Analysis of Synechocystis sp. PCC6803 Gene Expression in Minimal Media

Using a Synechocystis sp. PCC6803 DNA microarray prepared according to the methods described above and the cDNA probes prepared as described in Example 6, Applicants have identified herein promoters that can be employed for engineering high levels of gene expression in Synechocystis sp. PCC6803, other Synechocystis species, Synechococcus, and like organisms. This Example describes the identification of the most highly expressed genes and their corresponding strong promoters in Synechocystis sp. PCC6803 when grown in BG11 media containing 5 mM glucose as described above.

Specifically, a DNA microarray was prepared according to the methods described above using DNA isolated from Synechocystis sp. PCC6803 cells grown in BG11 media containing 5 mM glucose. Minimal media Synechocystis sp. PCC6803 gene expression was determined by hybridizing this DNA microarray as described above with fluorescent cDNA probes synthesized from total RNA isolated from Synechocystis sp. PCC6803 cells grown in BG11 media containing 5mM glucose as described in Example 6.

Briefly, for each minimal media experiment, two hybridization reactions were performed as described above. Specifically, the first reaction used equal molar (typically 100–200 pmol) of Cy5-labeled cDNA from total RNA of the minimal media treated sample, and Cy3-labeled cDNA probes synthesized from Synechocystis sp. PCC6803 genomic DNA; the second reaction used Cy3-labeled cDNA from total RNA of the minimal media treated sample, and Cy5-labeled cDNA probes synthesized from Synechocystis sp. PCC6803 genomic DNA. The signal intensities were quantitated as described above. To calculate the ratio of fold induction (i.e., minimal media/genomic), the minimal media treated sample signal intensities were divided by the signal intensities of the genomic sample. As there were two sets of data from duplicated spotting within each slide, the total number of gene expression measurements for each gene was four. All four induction ratios for each gene were analyzed using an Excel program (Microsoft) to determine the standard deviation; an indicator of the level of confidence for the specific data set for each gene. The ratio of signal intensities represents a relative transcription level of each gene in the same experiment. Herein, Applicants have identified the most highly expressed genes, i.e., those genes that are under the control of the strongest promoters, in Synechocystis under this minimal media condition (see Table 9).

Example 8

Analysis of Synechocystis sp. PCC6803 Gene Expression Following UV-B Exposure

Using a Synechocystis sp. PCC6803 DNA microarray prepared according to the methods described above and the probes prepared as described above in Example 6, Applicants have identified herein UV-B inducible promoters that can be employed for engineering high levels of gene expression in Synechocystis sp. PCC6803, other Synechocystis species, Synechococcus, and like organisms. This Example describes the identification of the most highly UV-B responsive genes in Synechocystis sp. PCC6803 when grown under minimal media conditions and exposed to 20 minutes of UV-B irradiation at 20 $\mu ES^{-1}m^{-2}$ intensity. These UV inducible promoters can be used to control expression of certain proteins that may be toxic to Synechocystis cells.

Specifically, a DNA microarray was prepared according to the methods described above using DNA isolated from Synechocystis sp. PCC6803. For each UV-B treatment experiment, two hybridization reactions were performed as described above. In particular, the first reaction used equal molar (typically 100–200 pmol) of Cy5-labeled cDNA from total RNA of the UV-B treated sample, and Cy3-labeled cDNA from total RNA of the control sample (Synechocystis sp. PCC6803 grown in BG11 media containing 5 mM glucose); the second reaction used Cy3-labeled cDNA from total RNA of the UV-B treated sample, and Cy5-labeled cDNA from total RNA of the control sample. The signal intensities were quantitated as described above. To calculate the ratio of fold induction (i.e., UV-B/control), the UV-B treated sample signal intensities were divided by the signal intensities of the control sample. As there were two sets of data from duplicated spotting within each slide, the total number of gene expression measurements for each gene was four. All four induction ratios for each gene were analyzed using an Excel program (Microsoft) to determine the standard deviation; an indicator of the level of confidence for the specific data set for each gene.

Applicants have identified herein the most highly UV-B induced genes in Synechocystis following UV-B treatment (see Table 10). Only genes whose expression was induced more than 4 folds by UV-B light (20 min at 20 $\mu ES^{-1}m^{-2}$ intensity) as compared to the minimal media control are listed in Table 10. The promoters of these genes can be used to construct UV inducible expression vectors in Synechocystis.

Some of the gene families induced by UV-B light include D1 protein (psbA), phycobilisome degradation proteins (nblA, nblB), carotenoid biosynthesis enzymes (crtD, crtD, crtQ), chaperones (clpB, ctpA, dnaJ, dnaK, htpG, hsp17), RNA polymerase sigma factor (rpoD), superoxide dismutase (sodB), high light inducible protein (hliA), FtsH protease, which is responsible for the degradation of photo-damaged D1 protein (ftsH), and DNA repair enzyme (uvrC). Among the group of UV inducible genes, there are several genes of unknown function: ssr2016, and sll0185. Applicants' discovery has lead to the first level of functional assignment for these genes. The promoters of these genes can be used to construct UV inducible expression vectors in Synechocystis.

A subgroup of Applicants' identified UV-B induced genes comprise two Escherichia coli-like -35 promoter sequences in the 5' upstream untranslated regions (UTR), including slr1604 (ftsH), slr0228 (ftsH), sll1867 (psbA3), slr1311 (psbA2), ssl0452 (nblA), ssl0453 (nblA), ssl2542 (hliA), ssr2016 (unknown protein with homologues in green algae and plant), and sll0185 (unknown protein). The nucleotide sequence "GTTACA" is present in the 5' untranslated regions of psbA2, psbA3, and ssr2016 nucleic acids. The nucleotide sequence "TTTACA" was also found to be present in the 5' UTR regions of psbA2, psbA3, ssr2016, rpoD, and ndhD2 nucleic acids.

TABLE 1

| | | LB | | | MM exp.phase | | MM transition phase | |
|---|---|---|---|---|---|---|---|---|
| gene | function | fold IPTG induction | fn[a] | rank[b] | fn | rank | fn | rank |
| lacA | thiogalactoside acyltransferase | 36 | 4.00E − 05 | 3747 | 2.46E − 07 | 4244 | 2.09E − 05 | 3816 |
| lacZ | galactosidase | 29 | 8.88E − 05 | 2420 | 2.16E − 05 | 3879 | 1.98E − 05 | 3849 |
| lacY | galactoside permease | 14 | 6.07E − 05 | 3125 | 6.10E − 06 | 4202 | 1.63E − 05 | 3975 |

TABLE 1-continued

| | LB | | | MM exp.phase | | MM transition phase | |
|---|---|---|---|---|---|---|---|
| gene | function | fold IPTG induction | fn[a] | rank[b] | fn | rank | fn | rank |
| b2324 | peptidase? | 5.3 | 2.78E − 04 | 621 | 7.30E − 05 | 2639 | 5.43E − 05 | 2717 |
| uxaA | altronate hydrolase | 4.0 | 2.93E − 04 | 575 | 7.82E − 05 | 2530 | 9.03E − 05 | 1990 |
| b1783/ yeaG | | 3.6 | 3.71E − 04 | 401 | 3.23E − 04 | 576 | 1.04E − 03 | 136 |
| melA | galactosidase | 2.9 | 4.05E − 05 | 3729 | 1.36E − 05 | 4050 | 1.65E − 05 | 3966 |
| b0956/ ycbG | hydrogenase? | 2.5 | 2.63E − 04 | 678 | 1.41E − 04 | 1573 | 1.27E − 04 | 1529 |

[a] = fraction of particular transcript/summed transcripts hybridizing to all open reading frames on the micro-arrays;
[b] = genes are ranked in order of expression with 1 being the most highly expressed gene
MM: Minimal media,
exp phase: exponential growth phase

TABLE 2

Highly Expressed Genes under Three Different Culture Conditions

| name | fraction[a] in LB | name | fraction in minimal (exp. phase) | name | fraction in minimal (transition) |
|---|---|---|---|---|---|
| infC[b] | 0.0070 | cspA | 0.0054 | hdeA | 0.016 |
| rplK | 0.0068 | metE | 0.0050 | hdeB | 0.0099 |
| rplL | 0.0066 | tufB | 0.0048 | rmf | 0.0083 |
| rplA | 0.0048 | ompA | 0.0046 | dps | 0.0065 |
| hemK | 0.0047 | ilvC | 0.0042 | lpp | 0.0063 |
| rpmI | 0.0046 | rmf | 0.0038 | ompC | 0.0059 |
| rplW | 0.0044 | tufA | 0.0038 | icdA | 0.0059 |
| rplJ | 0.0043 | ompT | 0.0037 | metE | 0.0053 |
| acpP | 0.0042 | infC | 0.0036 | gapA | 0.0049 |
| lpp | 0.0040 | ahpC | 0.0034 | tufA | 0.0049 |
| glpQ | 0.0039 | rplM | 0.0031 | ompA | 0.0044 |
| fusA | 0.0039 | ptsH | 0.0031 | infC | 0.0044 |
| gatB | 0.0038 | aceB | 0.0030 | uspA | 0.0040 |
| rpsF | 0.0038 | lpp | 0.0029 | tufB | 0.0039 |
| tufB | 0.0037 | rpsJ | 0.0028 | ilvC | 0.0037 |
| ompC | 0.0037 | cirA | 0.0028 | rpsN | 0.0036 |
| mopB | 0.0035 | gapA | 0.0026 | eno | 0.0036 |
| atpF | 0.0035 | rpmI | 0.00266 | ahpC | 0.0035 |
| hns | 0.0035 | yjjS | 0.0026 | ompT | 0.0033 |
| rpmB | 0.0034 | rpmC | 0.0024 | gadA | 0.0033 |
| ompA | 0.0033 | fusA | 0.0024 | aceB | 0.0033 |
| tnaA | 0.0033 | b2745 | 0.0024 | rplX | 0.0032 |
| rpoA | 0.0033 | ompF | 0.0023 | fusA | 0.0032 |
| trmD | 0.0032 | cspC | 0.0022 | ptsH | 0.0031 |
| rplI | 0.0031 | aceA | 0.0021 | rpsD | 0.0029 |
| gapA | 0.0030 | pyrB | 0.0021 | b3512 | 0.0029 |
| rplM | 0.0028 | rplK | 0.0021 | gpmA | 0.0028 |
| rpmG | 0.0028 | rpsD | 0.0021 | metK | 0.0028 |
| rpsC | 0.0027 | cysK | 0.0020 | rpmC | 0.0027 |
| rplT | 0.0027 | ptsI | 0.0020 | gadB | 0.0027 |
| rplX | 0.0027 | b1452 | 0.0019 | rpsV | 0.0027 |
| priB | 0.0026 | rpsS | 0.0019 | cysK | 0.0026 |
| ompF | 0.0025 | fepA | 0.0019 | rpsJ | 0.0025 |
| hupA | 0.0025 | pyrI | 0.0018 | rpsH | 0.0025 |
| rpsJ | 0.0025 | aroF | 0.0018 | rplE | 0.0025 |
| rplB | 0.0025 | rpsH | 0.0017 | aceA | 0.0025 |
| rplU | 0.0025 | rpsN | 0.0017 | b2266 | 0.0023 |
| tig | 0.0024 | b0805 | 0.0017 | rplM | 0.0023 |
| tufA | 0.0024 | ompC | 0.0017 | rpsS | 0.0023 |
| rplD | 0.0024 | rspA | 0.0017 | nlpD | 0.0022 |
| rplC | 0.0024 | thrL | 0.0017 | acpP | 0.0022 |
| gatA | 0.0024 | rplX | 0.0016 | rpmI | 0.0022 |
| rpsA | 0.0024 | rplL | 0.0016 | rpoS | 0.0021 |
| gatY | 0.0023 | rspM | 0.0016 | rpoA | 0.0020 |
| rpsS | 0.0023 | w4148 | 0.0016 | hns | 0.0020 |
| ppa | 0.0022 | rplB | 0.0016 | b4253 | 0.0020 |
| gatZ | 0.0022 | w0793 | 0.0016 | rplB | 0.0020 |
| cspE | 0.0021 | folE | 0.0015 | b1452 | 0.0019 |
| cspC | 0.0021 | icdA | 0.0015 | b0817 | 0.0019 |
| mopA | 0.0021 | rplW | 0.0015 | b1003 | 0.0019 |

[a]fraction of transcripts hybridizing to specified gene/summed transcripts hybridizing to all open reading frames on the midro-arrays
bold, double underlined -foldase/unsher genes; bold, underlined -stress responsive genes; bold -central metabolic enzyme-specifying genes; double underlined -biosynthetic genes; dotted underlined - translation-associated genes; underlined -rpoS controlled genes

TABLE 3

Summary of three *E. coli* Expression Profiles

| | fraction in MM[a], exp.[b] phase | fraction in MM/ transition phase | fraction in LB/exp. phase |
|---|---|---|---|
| 1. Cell processes | | | |
| Cell division-26[c] | 0.011 | 0.010 | 0.010 |
| Chemotaxis motility | | | |
| Chemotaxis and mobility-12 | 0.0014 | 0.00068 | 0.0011 |
| Folding and ushering proteins-7 | 0.0032 | 0.0061 | 0.01 |
| Transport of large molecules | | | |
| Protein, peptide secretion-32 | 0.0082 | 0.01014 | 0.010 |
| Transport of small molecules | | | |
| Amino acids, amines-49 | 0.0091 | 0.0081 | 0.0068 |
| Anions-20 | 0.0029 | 0.0028 | 0.0023 |
| Carbohydrates, organic acids, alcohols-82 | 0.020 | 0.016 | 0.034 |
| Cations-52 | 0.012 | 0.0098 | 0.0076 |
| Nucleosides, purines, pyrimidines-6 | 0.0010 | 0.00090 | 0.0017 |
| Other-12 | 0.0021 | 0.0027 | 0.0012 |
| 2. Elements of external origin: | | | |
| Laterally acquired elements Colicin-related functions-5 | 0.024 | 0.017 | 0.023 |
| Phage-related functions and prophages-27 | 0.0055 | 0.0042 | 0.0065 |
| Plasmid-related functions-1 | 0.00017 | 0.00055 | 0.00086 |
| Transposon-related functions-34 | 0.0058 | 0.0035 | 0.0038 |
| 3. Global functions | | | |
| Energy transfer, ATP-proton motive force-9 | 0.0077 | 0.0054 | 0.015 |
| Global regulatory functions-51 | 0.0176 | 0.029 | 0.018 |
| 4. Macromolecule metabolism | | | |
| Basic proteins | | | |
| Basic proteins - synthesis, modification-6 | 0.0047 | 0.0048 | 0.0074 |
| Macromolecule degradation | | | |
| Degradation of DNA-23 | 0.0038 | 0.0030 | 0.0031 |
| Degradation of RNA-11 | 0.0029 | 0.0015 | 0.0022 |
| Degradation of polysaccharides-3 | 0.00056 | 0.00033 | 0.00040 |
| Degradation of proteins, peptides, glyco-61 | 0.00842 | 0.0093 | 0.011 |
| Macromolecule synthesis, modification | | | |
| DNA - replication, repair, restr./modific'n-89 | 0.023 | 0.019 | 0.031 |
| Lipoprotein-11 | 0.0041 | 0.0050 | 0.0037 |
| Phospholipids-11 | 0.0020 | 0.0015 | 0.0021 |
| polysaccharides - (cytoplasmic)-6 | 0.0015 | 0.0016 | 0.00060 |
| proteins - translation and modification-34 | 0.029 | 0.030 | 0.043 |
| RNA synthesis, modification, DNA transcript'n-27 | 0.010 | 0.010 | 0.015 |
| Macromolecules | | | |
| Glycoprotein Lipopolysaccharide-13 | .0015 | 0.0012 | 0.0018 |
| aa-tRNAs | | | |
| Amino acyl tRNA syn; tRNA modific'n-40 | 0.013 | 0.013 | 0.021 |
| 5. Metabolism of small molecules | | | |
| Amino acid biosynthesis | 0.012 | 0.0093 | 0.0033 |
| Biosynthesis of cofactors, carriers | 0.072 | 0.069 | 0.064 |
| Central intermediary metabolism | | | |
| 2'-Deoxyribonucleotide metabolism-12 | 0.0034 | 0.0032 | 0.0032 |
| Amino sugars-10 | 0.0012 | 0.0011 | 0.0015 |
| Entner-Douderoff-3 | 0.00040 | 0.00034 | 0.00060 |
| Gluconeogenesis-4 | 0.00086 | 0.0012 | 0.0021 |
| Glyoxylate bypass-5 | 0.0076 | 0.0075 | 0.0012 |
| Misc. glucose metabolism-3 | 0.00085 | 0.00050 | 0.00039 |
| Non-oxidative branch, pentose pwy-8 | 0.0026 | 0.0043 | 0.0043 |
| Nucleotide hydrolysis-2 | 0.00010 | 0.00011 | 0.00027 |
| Nucleotide interconversions-13 | 0.0041 | 0.0039 | 0.002 |
| Phosphorus compounds-17 | 0.0032 | 0.0030 | 0.0022 |
| Polyamine biosynthesis-8 | 0.0016 | 0.0013 | 0.0013 |
| Salvage of nucleosides and nucleotides-18 | 0.0037 | 0.0038 | 0.0054 |
| Sugar-nucleotide biosynthesis, conversions-18 | 0.0042 | 0.0034 | 0.0048 |
| Sulfur metabolism-10 | 0.0039 | 0.0025 | 0.00095 |
| Pool, multipurpose conversions of intermed. Met'-46 | 0.012 | 0.019 | 0.021 |
| Degradation of small molecules | | | |
| Amines-9 | 0.0016 | 0.0010 | 0.0025 |
| Amino acids-17 | 0.0022 | 0.0014 | 0.0072 |
| Carbon compounds-90 | 0.014 | 0.011 | 0.025 |
| Fatty acids-10 | 0.0020 | 0.0017 | 0.0030 |
| Other-8 | 0.0015 | 0.0021 | 0.00075 |
| Energy metabolism carbon | | | |
| Aerobic respiration-27 | 0.0077 | 0.0058 | 0.012 |
| Anaerobic respiration-80 | 0.0075 | 0.0057 | 0.011 |
| Electron transport-24 | 0.0032 | 0.0024 | 0.0048 |
| Fermentation-21 | 0.0040 | 0.0050 | 0.0044 |
| Glycolysis-18 | 0.013 | 0.024 | 0.015 |
| Oxidative branch, pentose pwy-2 | | | |
| Pyruvate dehydrogenase-6 | 0.0046 | 0.0041 | 0.0040 |
| TCA cycle-18 | 0.0089 | 0.012 | 0.0093 |
| Fatty acid biosynthesis | | | |
| Fatty acid and phosphatidic acid biosynthesis-23 | 0.0073 | 0.0094 | 0.015 |
| Nucleotide synthesis | 0.019 | 0.013 | 0.010 |
| Purine ribonucleotide biosynthesis-22 | 0.011 | 0.0077 | 0.0083 |
| Pyrimidine ribonucleotide biosynthesis-10 | 0.0079 | 0.0049 | 0.0018 |
| 6. Miscellaneous | 0.37 | 0.37 | 0.28 |
| Not classified-109 | 0.022 | 0.023 | 0.025 |
| 7. Open reading frames | | | |
| Unknown proteins-1324 | 0.35 | 0.34 | 0.26 |
| 8. Processes | | | |
| Adaptation | | | |
| Adaptations, atypical conditions-16 | 0.012 | 0.0083 | 0.0074 |
| Osmotic adaptation-14 | 0.0038 | 0.0063 | 0.0026 |

TABLE 3-continued

Summary of three E. coli Expression Profiles

| | fraction in MM[a], exp.[b] phase | fraction in MM/ transition phase | fraction in LB/exp. phase |
|---|---|---|---|
| Protection responses | | | |
| Cell killing-3 | 0.00052 | 0.00031 | 0.00031 |
| Detoxification-11 | 0.0080 | 0.0083 | 0.0097 |
| Drug/analog sensitivity-32 | 0.0042 | 0.0031 | 0.0038 |
| 9. Structural elements | | | |
| Cell envelope | | | |
| Inner membrane-4 | | | |
| Murein sacculus, peptidoglycan-34 | 0.0095 | 0.012 | 0.013 |
| Outer membrane constituents-17 | 0.023 | 0.026 | 0.020 |
| Cell exterior constituents-16 | 0.0037 | 0.0039 | 0.0062 |
| Surface polysaccharides & antigens | | | |
| Surface structures-57 | 0.0075 | 0.0051 | 0.0052 |
| Ribosome constituents | | | |
| Ribosomal and stable RNAs-3 | | | |
| Ribosomal proteins - synthesis, modificationRiboso-54 | 0.079 | 0.086 | 0.15 |
| Ribosomes - maturation and modification-6 | 0.0056 | 0.011 | 0.00066 |
| 10. ORFs not listed-102 | | | |

[a]MM = Minimal medium,
[b]exp. = exponential,
[c]the number following each description is the number of genes summed

TABLE 4

Gene expression elevated by the presence of a sdiA multi-copy plasmid.

| Genes (grouping by function) | Fold induction |
|---|---|
| 1. Cell processes | |
| Cell division | |
| fisA | 10. |
| fisQ | 8.8 |
| fisZ | 11 |
| minC | 2.1 |
| minD | 2.7 |
| minE | 2.4 |
| sdiA | 30. |
| sulA | 2.6 |
| Chemotaxis and motility | |
| Transport of large molecules | |
| Protein, peptide secretion | |
| msyB | 2.1 |
| oppA | 2.1 |
| sapB | 2.2 |
| secD | 2.5 |
| secF | 2.4 |
| Transport of small molecules | |
| Amino acids, amines | |
| glnH | 4.0 |
| glnQ | 2.5 |
| Carbohydrates, organic acids, alc | |
| araE | 5.0 |
| frvA | 3.2 |
| frwD | 2.1 |
| gntU-I | 2.0 |
| srlB | 2.1 |
| xylF | 3.8 |

TABLE 4-continued

Gene expression elevated by the presence of a sdiA multi-copy plasmid.

| Genes (grouping by function) | Fold induction |
|---|---|
| Cations | |
| bfr | 2.0 |
| chaA | 2.0 |
| feoA | 5.8 |
| fepD | 2.1 |
| trkG | 4.1 |
| 2. Elements of external origin: | |
| Transposon-related functions | |
| rhsC | 6.3 |
| 3. Global regulatory functions | |
| lon | 2.4 |
| lrp | 2.2 |
| lytB? | 3.0 |
| rpoE | 2.4 |
| rseA | 2.5 |
| rseB | 2.2 |
| 4. Macromolecule metabolism | |
| Degradation of proteins, peptides | |
| htrA | 2.3 |
| hycI | 2.8 |
| ptr | 2.1 |
| Degradation of DNA | |
| endA | 2.2 |
| mcrB | 2.1 |
| mcrC | 3.5 |
| recD | 2.4 |
| uvrC | 9.3 |
| Macromolecule synthesis, modifi | |
| DNA - replication, repair, | |
| gidA | 4.1 |
| gidB | 2.3 |
| hupB | 4.5 |
| mioC | 7.0 |
| mutH | 2.2 |
| nei | 8.6 |
| priC | 2.8 |
| recN | 3.6 |
| umuC | 2.3 |
| uvrA | 2.0 |
| xerD | 2.3 |
| Lipoprotein | |
| blc | 2.8 |
| nlpC | 3.2 |
| vacJ | 2.1 |
| Phospholipids | |
| pgsA | 2.4 |
| polysaccharides - (cytoplasmic) | |
| glgC | 2.1 |
| glgS | 2.1 |
| proteins - translation and modific | |
| prfH | 2.2 |
| Lipopolysaccharide | |
| rfaK | 2.3 |
| rfaL | 2.1 |
| rfaY | 2.1 |
| rfaz | 2.5 |
| 5. Metabolism of small molecule | |
| Amino acids | |
| argA | 3.4 |
| aroD | 2.6 |
| glnA | 2.5 |

TABLE 4-continued

Gene expression elevated by the presence of a sdiA multi-copy plasmid.

| Genes (grouping by function) | Fold induction |
|---|---|
| glnD | 2.6 |
| lysR | 3.6 |
| Biosynthesis of cofactors, carrier | |
| thiD | 2.1 |
| thiM | 2.2 |
| gst | 3.1 |
| Central intermediary metabolism | |
| 2'-Deoxyribonucleotide metaboli | |
| nrdA | 2.1 |
| Amino sugars | |
| agaD | 4.5 |
| Gluconeogenesis | |
| ppsA | 2.4 |
| Phosphorus compounds | |
| psiF | 3.2 |
| Polyamine biosynthesis | |
| speC | 9.5 |
| Salvage of nucleosides and nucle | |
| apt | 2.4 |
| gsk | 2.4 |
| Pool, multipurpose conversions o | |
| galM | 2.3 |
| gcvA | 4.6 |
| glnK | 2.1 |
| pntA | 10.4 |
| pntB | 8.2 |
| Degradation of small molecules | |
| Amino acids | |
| tdcB | 2.0 |
| tdcR | |
| Carbon compounds | |
| fucA | 2.8 |
| fucU | 14 |
| galE | 3.8 |
| galK | 4.1 |
| galT | 4.9 |
| glcD | 2.0 |
| gusR (uidR) | 8.0 |
| lacA | 3.7 |
| lacI | 2.5 |
| uxuC | |
| Fatty acids | |
| atoD | 3.8 |
| Energy metabolism, carbon | |
| Aerobic respiration | |
| nuoH | 2.1 |
| nuoI | 2.1 |
| Anaerobic respiration | |
| dniR | 5.8 |
| hybD | 3.8 |
| hybE | 12 |
| hybF | 6.6 |
| hycA | 3.1 |
| hycG | 2.7 |
| hycH | 3.8 |
| hydN | 13 |
| hypC | 2.3 |
| nrfB | 2.7 |
| nrfG | 2.1 |

TABLE 4-continued

Gene expression elevated by the presence of a sdiA multi-copy plasmid.

| Genes (grouping by function) | Fold induction |
|---|---|
| Electron transport | |
| appB | 2.5 |
| cybC | 2.1 |
| Pyruvate dehydrogenase | |
| pdhR | 4.4 |
| TCA cycle | |
| fumc | 5.8 |
| sucA | 2.1 |
| sucB | 2.6 |
| sucC | 2.2 |
| sucD | 2.7 |
| Fatty acid and phosphatidic acid | |
| aas | 2.0 |
| cdh | 2.3 |
| Purine ribonucleotide biosynthes | |
| purE | 2.1 |
| purR | 2.3 |
| Pyrimidine ribonucleotide | |
| pyrL | 2.1 |
| 6. Processes | |
| Detoxification | |
| cutC | 2.1 |
| Drug/analog sensitivity | |
| acrA | 6.8 |
| acrD | 3.0 |
| acrE | 14 |
| acrF | 6.3 |
| acrR | 4.5 |
| ampC | 2.6 |
| arsC | 2.1 |
| tolC | 2.6 |
| 7. Structural elements | |
| Cell envelope | |
| Inner membrane | |
| smpA | 2.6 |
| Murein sacculus, peptidoglycan | |
| ddlB | 4.6 |
| hipB | 2.0 |
| mreD | 2.0 |
| Outer membrane constituents | |
| sip | 2.5 |
| Cell exterior constituents | |
| kdsA | 2.3 |
| lpxC | 3.4 |
| rfaB? | 2.6 |
| Ribosome constituents | |
| Ribosomal proteins - synthesis, | |
| rpsL | 3.1 |
| 8. Not classified | |
| agaI | 3.3 |
| chpA | 3.0 |
| dinI | 2.0 |
| dinP | |
| envR | 2.2 |
| ppdB | 2.9 |
| sohA | 4.9 |
| sugE | 2.2 |
| uvrY | 11.9 |

TABLE 4-continued

Gene expression elevated by the presence of a sdiA multi-copy plasmid.

| Genes (grouping by function) | Fold induction |
| --- | --- |
| 9. Open reading frames of unknown functions | |
| apaG | 2.0 |
| hdeB | 2.4 |
| relE | 2.1 |
| sprT | 3.8 |
| b0065 | 3.7 |
| b0097 | 2.1 |
| b0135 | 6.4 |
| b0137 | 2.5 |
| b0138 | 2.1 |
| b0141 | 4.6 |
| b0163 | 2.8 |
| b0189 | 2.3 |
| b0224 | 2.1 |
| b0225 | 6.4 |
| b0232 | 3.1 |
| b0233 | 2.9 |
| b0234 | 3.1 |
| b0245 | 2.3 |
| b0269 | 3.2 |
| b0281 | 2.4 |
| b0295 | 2.8 |
| b0300 | 2.0 |
| b0303 | 4.7 |
| b0322 | 2.5 |
| b0404 | 3.0 |
| b0407 | 2.9 |
| b0412 | 2.4 |
| b0443 | 2.2 |
| b0461 | 2.1 |
| b0498 | 2.3 |
| b0517 | 11.2 |
| b0519 | 2.5 |
| b0530 | 6.5 |
| b0534 | 2.6 |
| b0567 | 2.2 |
| b0625 | 3.5 |
| b0710 | 5.2 |
| b0711 | 4.7 |
| b0712 | 6.4 |
| b0713 | 3.8 |
| b0715 | 2.2 |
| b0767 | 3.3 |
| b1023 | 2.7 |
| b1024 | 2.1 |
| b1069 | 3.8 |
| b1113 | 3.8 |
| b1214 | 2.3 |
| b1321 | 2.1 |
| b1438 | 11 |
| b1451 | 2.0 |
| b1454 | 2.2 |
| b1455 | 6.4 |
| b1458 | 2.3 |
| b1463 | 2.1 |
| b1487 | 3.0 |
| b1491 | 2.3 |
| b1498 | 3.7 |
| b1499 | 2.6 |
| b1504 | 2.1 |
| b1540 | 2.5 |
| b1541 | 6.2 |
| b1542 | 3.2 |
| b1543 | 2.4 |
| b1544 | 3.0 |
| b1545 | 4.4 |
| b1547 | 2.2 |
| b1551 | 2.1 |
| b1560 | 3.8 |
| b1565 | 3.4 |
| b1567 | 3.5 |
| b1568 | 2.0 |
| b1579 | 2.6 |
| b1586 | 2.2 |
| b1601 | 4.0 |
| b1606 | 8.0 |
| b1607 | 7.7 |
| b1624 | 2.1 |
| b1627 | 2.4 |
| b1628 | 3.0 |
| b1632 | 2.1 |
| b1648 | 2.6 |
| b1649 | 2.7 |
| b1657 | 4.7 |
| b1664 | 2.1 |
| b1673 | 2.4 |
| b1688 | 2.6 |
| b1699 | 2.0 |
| b1700 | 3.7 |
| b1701 | 2.0 |
| b1706 | 2.4 |
| b1707 | 30 |
| b1721 | 6.5 |
| b1724 | 2.1 |
| b1743 | 2.2 |
| b1744 | 2.5 |
| b1746 | 2.9 |
| b1756 | 3.2 |
| b1789 | 3.6 |
| b1847 | 2.3 |
| b1848 | 2.7 |
| b1870 | 2.4 |
| b1871 | 2.8 |
| b1875 | 3.4 |
| b1877 | 2.4 |
| b1935 | 2.1 |
| b1953 | 3.5 |
| b1955 | 5.1 |
| b1956 | 14 |
| b1965 | 5.2 |
| b1967 | 6.6 |
| b1968 | 2.4 |
| b2006 | 4.4 |
| b2007 | 2.1 |
| b2015 | 3.6 |
| b2016 | 3.5 |
| b2017 | 3.8 |
| b2061 | 2.2 |
| b2071 | 3.1 |
| b2145 | 2.7 |
| b2190 | 2.3 |
| b2229 | 2.1 |
| b2247 | 2.3 |
| b2253 | 2.3 |
| b2267 | 2.0 |
| b2268 | 2.0 |
| b2269 | 2.6 |
| b2270 | 2.2 |
| b2301 | 3.8 |
| b2302 | 7.5 |
| b2339 | 2.0 |
| b2352 | 2.6 |
| b2356 | 2.3 |
| b2385 | 2.1 |
| b2387 | 3.6 |
| b2419 | 3.2 |
| b2420 | 3.2 |
| b2439 | 2.1 |
| b2443 | 2.7 |
| b2444 | 2.1 |
| b2445 | 2.7 |
| b2485 | 2.2 |
| b2505 | 2.1 |
| b2597 | 2.8 |
| b2628 | 2.2 |
| b2629 | 3.4 |
| b2631 | 2.9 |
| b2632 | 4.2 |

TABLE 4-continued

Gene expression elevated by the presence of a sdiA multi-copy plasmid.

| Genes (grouping by function) | Fold induction |
|---|---|
| b2640 | 5.0 |
| b2641 | 2.3 |
| b2642 | 15 |
| b2643 | 2.6 |
| b2648 | 3.7 |
| b2649 | 3.0 |
| b2756 | 2.4 |
| b2767 | 2.9 |
| b2833 | 2.1 |
| b2845 | 2.6 |
| b2846 | 3.0 |
| b2851 | 2.6 |
| b2862 | 2.4 |
| b2874 | 3.3 |
| b2912 | 2.6 |
| b2931 | 2.2 |
| b2984 | 2.1 |
| b3021 | 2.4 |
| b3022 | 2.7 |
| b3047 | 2.2 |
| b3050 | 2.2 |
| b3130 | 2.7 |
| b3142 | — |
| b3254 | 3.8 |
| b3372 | 2.2 |
| b3379 | 2.0 |
| b3395 | 4.6 |
| b3397 | 3.5 |
| b3398 | 2.2 |
| b3441 | 4.0 |
| b3465 | 2.1 |
| b3467 | 2.5 |
| b3487 | 2.1 |
| b3494 | 2.2 |
| b3513 | 5.3 |
| b3535 | 2.2 |
| b3536 | 2.9 |
| b3548 | 2.0 |
| b3615 | 2.0 |
| b3697 | 2.9 |
| b3711 | 2.3 |
| b3712 | 2.1 |
| b3713 | 2.1 |
| b3714 | 2.2 |
| b3719 | 2.5 |
| b3720 | 3.0 |
| b3776 | 2.9 |
| b3820 | 2.5 |
| b3888 | 3.4 |
| b3937 | 2.1 |
| b3944 | 2.0 |
| b3964 | 2.2 |
| b4038 | 2.4 |
| b4068 | 2.5 |
| b4141 | 2.3 |
| b4156 | 2.2 |
| b4191 | 5.1 |
| b4221 | 5.0 |
| b4222 | 4.8 |
| b4234 | 2.9 |
| b4248 | 2.9 |
| b4282 | 2.1 |
| b4298 | 2.3 |
| b4300 | 2.2 |
| b4325 | 2.1 |
| b2088 | 9.4 |
| b4404 | 5.9 |
| b4405 | 4.2 |
| yieD (b3695) | 3.8 |
| b3914 | 3.5 |
| b3913 | 3.3 |
| yjiT (b4352) | 2.8 |
| yjiU (b4342) | 2.7 |
| yjjQ (b4364) | 2.4 |
| yhiL (b3486) | 2.3 |
| b2848 | 2.0 |
| b3573 | 2.0 |

TABLE 5

Gene expression reduced by the presence of a sdiA multi-copy plasmid.

| Genes (grouping by function) | Fold repression |
|---|---|
| 1. Cell processes | |
| Cell division | |
| fisx | 2.4 |
| Taxis and mobility | |
| air (aer) | 4.6 |
| cheA | 3.7 |
| cheB | 3.3 |
| cheR | 2.2 |
| cheW | 5.3 |
| cheY | 4.6 |
| cheZ | 4.0 |
| motA | 2.9 |
| motB | 2.9 |
| tar | 5.3 |
| tsr | 5.9 |
| Transport | |
| Protein, peptide secretion | |
| dppA | 2.3 |
| Amino acids, amines | |
| sdaC | 3.9 |
| Carbohydrates, organic acids alcohols | |
| fadL | 2.5 |
| glpF | 3.6 |
| glpT | 2.5 |
| lamB | 3.0 |
| malE | 3.7 |
| mglA | 2.7 |
| rbsA | 2.6 |
| treB | 5.3 |
| Cations | |
| fecA | 3.5 |
| fecB | 2.7 |
| fecE | 3.2 |
| ftn | 2.6 |
| kdpA | 3.5 |
| 2. Elements of external origin: Phage-related functions and prophages | |
| lar | 4.0 |
| nmpC | 2.1 |
| 3. Global regulatory functions | |
| cytR | 2.2 |
| 4. Degradation of macromolec | |
| DNA | |
| xseB | 4.8 |
| Proteins, peptides | |
| pepE | 2.6 |

TABLE 5-continued

Gene expression reduced by the presence of a sdiA multi-copy plasmid.

| Genes (grouping by function) | Fold repression |
|---|---|
| 5. Metabolism of small molecu | |
| Pool, multipurpose conversions of intermed. Met[1] | |
| glpK | 3.5 |
| glpQ | 2.3 |
| gltF | 2.6 |
| Degradation of small molecule | |
| Amino acids | |
| sdaB | 3.2 |
| tnaA | 4.0 |
| tnaL | 2.4 |
| Carbon compounds | |
| fucR | 2.8 |
| lacZ | 6.7 |
| malM | 3.0 |
| malT | 2.6 |
| treC | 2.6 |
| Energy metabolism, carbon | |
| Anaerobic respiration | |
| hypD | 2.2 |
| Fermentation | |
| ackA | 3.1 |
| aldA | 3.3 |
| pta | 2.3 |
| Fatty acid and phosphatidic acid biosynth | |
| accD | 3.0 |
| Purine ribonucleotide biosynth | |
| ndk | 2.2 |
| 6. Structural elements | |
| Outer membrane constituents | |
| flu | 7.7 |
| Cell exterior constituents | |
| nanA | 3.7 |
| Surface structures | |
| fimA | 2.6 |
| flgA | 2.3 |
| flgB | 14 |
| flgC | 17 |
| flgD | 17 |
| flgE | 17 |
| flgF | 7.1 |
| flgG | 13 |
| flgH | 5.9 |
| flgI | 5.6 |
| flgJ | 6.3 |
| flgK | 6.3 |
| flgL | 11 |
| flgM | 7.1 |
| flgN | 5.6 |
| flhA | 3.1 |
| fliA | 10. |
| fliC | 14. |
| fliD | 4.6 |
| fliE | 5.9 |
| fliF | 11 |
| fliG | 9.1 |
| fliH | 5.0 |
| fliI | 3.9 |
| fliJ | 7.1 |
| fliK | 4.8 |
| fliL | 7.7 |
| fliM | 13 |
| fliN | 5.0 |
| fliO | 4.4 |
| fliP | 6.3 |
| fliR | 3.1 |
| fliS | 5.9 |
| fliT | 5.6 |
| fliZ | 8.3 |
| Ribosomes - maturation and modification | |
| gutM | 2.1 |
| 7. Not classified | |
| fsr | 2.1 |
| 8. Open reading frames with unknown functions | |
| b0105 | 2.4 |
| b0235 | 2.1 |
| b0290 | 3.5 |
| b0307 | 2.4 |
| b0704 | 2.7 |
| b0732 | 2.0 |
| b1100 | 2.5 |
| b1194 | 5.0 |
| b1200 | 2.9 |
| b1329 | 2.2 |
| b1339 | 2.2 |
| b1383 | 2.4 |
| b1520 | 2.7 |
| b1566 | 4.4 |
| b1690 | 2.1 |
| b1722 | 2.2 |
| b1880 | 3.6 |
| b1929 | 2.1 |
| b1930 | 3.1 |
| b2001 | 2.3 |
| b2005 | 2.0 |
| b2014 | 2.4 |
| b2537 | 2.2 |
| b2844 | 2.7 |
| b3010 | 2.2 |
| b3111 | 2.6 |
| b3323 | 2.9 |
| b3442 | 2.5 |
| b3539 | 2.4 |
| b3872 | 2.1 |
| yjiZ (b4354) | 3.3 |
| yjbP (b3877) | 4.0 |
| yhjH (b3524) | 4.8 |

TABLE 6

Gene expression profiles of MG1655 strain when exposed to MMC

| m15 | control | final ratio | Gene name | M40 | control | total ratio | Gene name |
|---|---|---|---|---|---|---|---|
| 25115.41 | 4700.39 | 5.34 | recN | 98536.33 | 11895.47 | 8.28 | recN |
| 34003.66 | 4565.91 | 7.45 | hslS | 11287.86 | 1677.72 | 6.73 | hslS |
| 1146.46 | 769.58 | 1.49 | dinI | 10515.16 | 1564.72 | 6.72 | dinI |
| 2516.14 | 1468.51 | 1.71 | sulA | 13936.20 | 2416.81 | 5.77 | sulA |
| 4531.55 | 2030.86 | 2.23 | w1816 | 18614.34 | 3231.00 | 5.76 | w1816 |
| 34497.54 | 4438.78 | 7.77 | hslT | 21578.60 | 5358.30 | 4.03 | hslT |
| 8490.60 | 4896.22 | 1.73 | lexA | 22768.75 | 6375.09 | 3.57 | lexA |
| 992.44 | 1322.83 | 0.75 | w0522 | 8750.63 | 2628.39 | 3.33 | w0522 |
| 3207.65 | 2219.58 | 1.45 | w1815 | 16206.30 | 4874.54 | 3.32 | w1815 |
| 1844.00 | 1864.81 | 0.99 | w2141 | 2156.14 | 691.51 | 3.12 | w2141 |
| 21169.76 | 11055.79 | 1.91 | recA | 34375.81 | 11386.61 | 3.02 | recA |
| 756.88 | 510.08 | 1.48 | smpA | 1614.58 | 558.50 | 2.89 | smpA |
| 17140.20 | 23337.13 | 0.73 | cspA | 12566.23 | 4347.87 | 2.89 | cspA |
| 165.71 | 396.95 | 0.42 | ecpD | 227.53 | 80.37 | 2.83 | ecpD |
| 780.07 | 941.22 | 0.83 | w3019 | 802.62 | 288.87 | 2.78 | w3019 |
| 821.35 | 733.39 | 1.12 | w2878 | 1151.78 | 439.75 | 2.62 | w2878 |
| 301.47 | 384.64 | 0.78 | entD | 491.14 | 189.39 | 2.59 | entD |
| 385.41 | 778.62 | 0.49 | fhuC | 818.05 | 321.73 | 2.54 | fhuC |
| 7203.63 | 6899.86 | 1.04 | w1201 | 4623.01 | 1874.23 | 2.47 | w1201 |
| 1476.06 | 1291.17 | 1.14 | w2999 | 1710.57 | 709.13 | 2.41 | w2999 |
| 269.15 | 393.30 | 0.68 | caiB | 326.51 | 139.49 | 2.34 | caiB |
| 5327.31 | 6525.35 | 0.82 | infA | 8186.35 | 3504.89 | 2.34 | infA |
| 9150.34 | 6624.37 | 1.38 | uvrA | 33530.31 | 14452.89 | 2.32 | uvrA |
| 1657.22 | 1816.09 | 0.91 | w2879 | 3946.52 | 1727.30 | 2.28 | w2879 |
| 4322.77 | 5547.40 | 0.78 | insB_2 | 6522.25 | 2894.35 | 2.25 | insB_2 |
| 2310.26 | 1778.19 | 1.30 | dinD | 5316.67 | 2385.63 | 2.23 | dinD |
| 5349.03 | 4945.79 | 1.08 | secG | 6754.21 | 3076.60 | 2.20 | secG |
| 136.50 | 367.57 | 0.37 | priC | 341.80 | 156.11 | 2.19 | priC |
| 617.58 | 603.54 | 1.02 | w0561 | 11989.75 | 5479.59 | 2.19 | w0561 |
| 2228.66 | 2966.21 | 0.75 | exbD | 7165.39 | 3289.27 | 2.18 | exbD |
| 1282.58 | 893.81 | 1.43 | umuC | 5697.94 | 2659.80 | 2.14 | umuC |
| 6703.55 | 7422.39 | 0.90 | mioC | 8113.11 | 3804.25 | 2.13 | mioC |
| 3289.24 | 4228.67 | 0.78 | insB_1 | 6065.02 | 2854.20 | 2.12 | insB_1 |
| 4042.60 | 3531.25 | 1.14 | trkH | 17795.29 | 8430.83 | 2.11 | trkH |
| 867.30 | 1494.75 | 0.58 | w1345 | 1026.33 | 487.58 | 2.10 | w1345 |
| 541.83 | 848.15 | 0.64 | dniR | 1878.65 | 899.98 | 2.09 | dniR |
| 5469.65 | 4392.09 | 1.25 | uvrB | 14508.65 | 6960.78 | 2.08 | uvrB |
| 1561.63 | 2155.11 | 0.72 | insA_4 | 2298.22 | 1111.79 | 2.07 | insA_4 |
| 5398.87 | 3786.47 | 1.43 | ruvA | 10492.52 | 5134.38 | 2.04 | ruvA |
| 343.85 | 654.22 | 0.53 | appY | 815.11 | 400.28 | 2.04 | appY |
| 18257.00 | 17197.04 | 1.06 | xseA | 13206.64 | 6494.62 | 2.03 | xseA |
| 1863.91 | 1771.47 | 1.05 | w0224 | 6686.92 | 3310.73 | 2.02 | w0224 |
| 5595.42 | 6241.55 | 0.90 | w3139 | 11174.79 | 5555.32 | 2.01 | w3139 |
| 1656.98 | 1560.47 | 1.06 | w2512 | 24511.01 | 12207.10 | 2.01 | w2512 |
| 349.40 | 648.41 | 0.54 | w3304 | 428.93 | 850.84 | 0.50 | w3304 |
| 297.42 | 326.64 | 0.91 | w2228 | 271.97 | 539.98 | 0.50 | w2228 |
| 226.05 | 501.68 | 0.45 | chaB | 721.77 | 1433.44 | 0.50 | chaB |
| 678.56 | 880.61 | 0.77 | cydA | 699.94 | 1392.46 | 0.50 | cydA |
| 1422.74 | 2311.13 | 0.62 | melR | 5081.98 | 10140.17 | 0.50 | melR |
| 1051.64 | 763.06 | 1.38 | w1004 | 1265.66 | 2528.73 | 0.50 | w1004 |
| 386.58 | 562.93 | 0.69 | hofG | 315.25 | 630.05 | 0.50 | hofG |
| 513.59 | 611.47 | 0.84 | w1429 | 360.81 | 721.16 | 0.50 | w1429 |
| 1256.86 | 1688.60 | 0.74 | w0299 | 9464.02 | 18943.08 | 0.50 | w0299 |
| 695.83 | 807.90 | 0.86 | rpiR | 748.66 | 1502.59 | 0.50 | rpiR |
| 904.58 | 1028.97 | 0.88 | celD | 2009.30 | 4041.66 | 0.50 | celD |
| 2139.22 | 1712.26 | 1.25 | w0801 | 2801.71 | 5636.83 | 0.50 | w0801 |
| 749.35 | 812.05 | 0.92 | w0241 | 712.18 | 1434.35 | 0.50 | w0241 |
| 827.51 | 522.31 | 1.58 | w0621 | 1293.49 | 2605.36 | 0.50 | w0621 |
| 3746.49 | 3442.41 | 1.09 | putP | 12834.08 | 25859.69 | 0.50 | putP |
| 428.60 | 231.66 | 1.85 | w4099 | 377.87 | 764.43 | 0.49 | w4099 |
| 197.66 | 171.90 | 1.15 | prsA | 535.40 | 1091.60 | 0.49 | prsA |
| 158.38 | 114.75 | 1.38 | hybD | 177.80 | 363.82 | 0.49 | hybD |
| 83.33 | 438.61 | 0.19 | sapB | 501.32 | 1027.11 | 0.49 | sapB |
| 334.88 | 643.56 | 0.52 | w3821 | 412.40 | 845.78 | 0.49 | w3821 |
| 388.49 | 568.82 | 0.68 | w1459 | 417.69 | 857.67 | 0.49 | w1459 |
| 275.47 | 170.99 | 1.61 | agaD | 222.68 | 459.00 | 0.49 | agaD |
| 309.42 | 402.34 | 0.77 | ccmD | 646.05 | 1331.95 | 0.49 | ccmD |
| 328.75 | 360.49 | 0.91 | cpsG | 1070.07 | 2212.14 | 0.48 | cpsG |
| 421.02 | 702.69 | 0.60 | relB | 1002.28 | 2072.50 | 0.48 | relB |
| 1361.48 | 1629.16 | 0.84 | w2809 | 3556.91 | 7365.32 | 0.48 | w2809 |
| 924.92 | 626.14 | 1.48 | w0824 | 1242.77 | 2589.98 | 0.48 | w0824 |
| 794.28 | 965.82 | 0.82 | osmE | 2901.61 | 6072.91 | 0.48 | osmE |
| 277.27 | 66.53 | 4.17 | w0362 | 1234.58 | 2592.98 | 0.48 | w0362 |
| 612.37 | 471.85 | 1.30 | w1927 | 481.28 | 1014.05 | 0.47 | w1927 |

TABLE 6-continued

Gene expression profiles of MG1655 strain when exposed to MMC

| m15 | control | final ratio | Gene name | M40 | control | total ratio | Gene name |
|---|---|---|---|---|---|---|---|
| 726.43 | 629.35 | 1.15 | w0211 | 639.90 | 1353.69 | 0.47 | w0211 |
| 779.65 | 724.87 | 1.08 | w0237 | 855.85 | 1815.70 | 0.47 | w0237 |
| 853.25 | 919.94 | 0.93 | w2592 | 585.96 | 1247.13 | 0.47 | w2592 |
| 829.44 | 1006.55 | 0.82 | phnH | 987.67 | 2146.99 | 0.46 | phnH |
| 537.66 | 1161.05 | 0.46 | flgA | 577.37 | 1255.75 | 0.46 | flgA |
| 656.68 | 723.92 | 0.91 | w2595 | 377.12 | 821.43 | 0.46 | w2595 |
| 800.14 | 800.17 | 1.00 | w2600 | 792.47 | 1732.89 | 0.46 | w2600 |
| 69.56 | 216.88 | 0.32 | pheL | 93.28 | 205.15 | 0.45 | pheL |
| 892.86 | 431.26 | 2.07 | w3049 | 1146.62 | 2524.70 | 0.45 | w3049 |
| 764.84 | 318.13 | 2.40 | w1031 | 1045.43 | 2305.88 | 0.45 | w1031 |
| 937.41 | 1834.97 | 0.51 | w0295 | 473.49 | 1044.97 | 0.45 | w0295 |
| 486.50 | 540.31 | 0.90 | marB | 872.85 | 1928.83 | 0.45 | marB |
| 587.05 | 622.95 | 0.94 | w0665 | 786.69 | 1744.63 | 0.45 | w0665 |
| 711.12 | 397.24 | 1.79 | w1016 | 1399.58 | 3109.10 | 0.45 | w1016 |
| 903.55 | 1024.80 | 0.88 | w0298 | 8569.57 | 19066.70 | 0.45 | w0298 |
| 570.42 | 464.88 | 1.23 | w0812 | 1381.42 | 3073.94 | 0.45 | w0812 |
| 1112.52 | 446.12 | 2.49 | w2026 | 1456.45 | 3270.04 | 0.45 | w2026 |
| 909.59 | 321.83 | 2.83 | w0715 | 1050.65 | 2361.56 | 0.44 | w0715 |
| 739.31 | 960.38 | 0.77 | pyrL | 689.56 | 1552.58 | 0.44 | pyrL |
| 1533.58 | 1350.22 | 1.14 | menE | 1802.56 | 4058.69 | 0.44 | menE |
| 38.16 | 216.63 | 0.18 | rnb | 703.05 | 1594.10 | 0.44 | rnb |
| 707.80 | 1099.36 | 0.64 | fucR | 1770.89 | 4026.45 | 0.44 | fucR |
| 973.74 | 681.23 | 1.43 | w2818 | 278.71 | 634.22 | 0.44 | w2818 |
| 603.99 | 388.89 | 1.55 | acpD | 1990.24 | 4539.42 | 0.44 | acpD |
| 610.87 | 662.57 | 0.92 | w0489 | 332.52 | 758.67 | 0.44 | w0489 |
| 144.96 | 121.61 | 1.19 | ppdA | 177.26 | 405.05 | 0.44 | ppdA |
| 439.04 | 478.63 | 0.92 | w1966 | 488.90 | 1118.27 | 0.44 | w1966 |
| 277.30 | 324.71 | 0.85 | no template | 333.36 | 764.15 | 0.44 | no template |
| 1245.39 | 1015.95 | 1.23 | w2401 | 1085.45 | 2497.91 | 0.43 | w2401 |
| 570.79 | 872.26 | 0.65 | w4094 | 1505.90 | 3477.91 | 0.43 | w4094 |
| 100.79 | 255.85 | 0.39 | dicC | 543.43 | 1266.31 | 0.43 | dicC |
| 1035.07 | 1108.91 | 0.93 | w0286 | 844.03 | 1986.63 | 0.42 | w0286 |
| 4510.92 | 4439.04 | 1.02 | selB | 341.91 | 808.87 | 0.42 | selB |
| 1625.34 | 1568.78 | 1.04 | w2733 | 3589.01 | 8496.95 | 0.42 | w2733 |
| 187.58 | 341.03 | 0.55 | no template | 301.58 | 716.01 | 0.42 | no template |
| 1841.41 | 2180.01 | 0.84 | trpC | 10007.85 | 23940.58 | 0.42 | trpC |
| 278.39 | 137.91 | 2.02 | relF | 449.81 | 1077.54 | 0.42 | relF |
| 791.31 | 342.34 | 2.31 | w1318 | 1106.98 | 2655.28 | 0.42 | w1318 |
| 224.27 | 312.05 | 0.72 | agaV | 202.28 | 490.11 | 0.41 | agaV |
| 791.41 | 366.08 | 2.16 | w1002 | 1315.80 | 3189.26 | 0.41 | w1002 |
| 890.33 | 701.73 | 1.27 | w0685 | 1124.73 | 2728.61 | 0.41 | w0685 |
| 622.65 | 681.13 | 0.91 | potH | 500.10 | 1228.03 | 0.41 | potH |
| 993.12 | 584.36 | 1.70 | w2399 | 853.26 | 2107.06 | 0.40 | w2399 |
| 1275.28 | 924.58 | 1.38 | metA | 991.35 | 2449.36 | 0.40 | metA |
| 146.54 | 178.28 | 0.82 | lytB | 310.99 | 770.46 | 0.40 | lytB |
| 419.51 | 730.52 | 0.57 | w2987 | 638.04 | 1593.08 | 0.40 | w2987 |
| 827.42 | 695.16 | 1.19 | w0552 | 1225.71 | 3084.40 | 0.40 | w0552 |
| 568.15 | 412.40 | 1.38 | w1846 | 382.41 | 968.10 | 0.40 | w1846 |
| 114.29 | 119.19 | 0.96 | dicB | 533.34 | 1351.95 | 0.39 | dicB |
| 842.23 | 490.95 | 1.72 | w1005 | 970.38 | 2465.94 | 0.39 | w1005 |
| 912.78 | 720.90 | 1.27 | w2587 | 509.45 | 1301.74 | 0.39 | w2587 |
| 1229.46 | 751.44 | 1.64 | w1260 | 963.45 | 2507.31 | 0.38 | w1260 |
| 1448.48 | 1055.79 | 1.37 | w3068 | 12241.51 | 31901.37 | 0.38 | w3068 |
| 1010.15 | 949.49 | 1.06 | w0551 | 2143.72 | 5619.44 | 0.38 | w0551 |
| 794.65 | 573.71 | 1.39 | w2599 | 616.94 | 1633.89 | 0.38 | w2599 |
| 905.72 | 963.26 | 0.94 | w0569 | 912.64 | 2444.12 | 0.37 | w0569 |
| 1708.81 | 2679.92 | 0.64 | fruR | 7146.34 | 19274.42 | 0.37 | fruR |
| 1170.58 | 1168.59 | 1.00 | w3927 | 1323.78 | 3637.02 | 0.36 | w3927 |
| 2894.91 | 2291.60 | 1.26 | w3069 | 15445.74 | 42484.53 | 0.36 | w3069 |
| 1162.90 | 1058.22 | 1.10 | w0162 | 5614.02 | 15712.25 | 0.36 | w0162 |
| 494.27 | 467.07 | 1.06 | w0564 | 1311.37 | 3713.19 | 0.35 | w0564 |
| 2542.41 | 5907.71 | 0.43 | lar | 367.19 | 1045.32 | 0.35 | lar |
| 145.60 | 352.49 | 0.41 | agaB | 174.76 | 500.90 | 0.35 | agaB |
| 360.63 | 406.91 | 0.89 | w0356 | 893.83 | 2593.46 | 0.34 | w0356 |
| 146.66 | 228.04 | 0.64 | ptrB | 583.62 | 1710.66 | 0.34 | ptrB |
| 89.69 | 85.82 | 1.05 | tdcA | 140.71 | 420.20 | 0.33 | tdcA |
| 1569.84 | 1131.81 | 1.39 | w0005 | 854.54 | 2591.31 | 0.33 | w0005 |
| 949.03 | 723.77 | 1.31 | w2820 | 711.72 | 2231.62 | 0.32 | w2820 |
| 382.29 | 200.74 | 1.90 | racC | 145.56 | 473.98 | 0.31 | racC |
| 966.21 | 528.97 | 1.83 | w1323 | 814.12 | 2717.50 | 0.30 | w1323 |
| 2804.26 | 3141.20 | 0.89 | tolQ | 7715.84 | 26048.34 | 0.30 | tolQ |
| 349.28 | 732.94 | 0.48 | w0535 | 238.50 | 834.39 | 0.29 | w0535 |

TABLE 6-continued

Gene expression profiles of MG1655 strain when exposed to MMC

| m15 | control | final ratio | Gene name | M40 | control | total ratio | Gene name |
|---|---|---|---|---|---|---|---|
| 19047.83 | 10107.02 | 1.88 | w2546 | 13321.17 | 46691.65 | 0.29 | w2546 |
| 580.46 | 495.64 | 1.17 | w0553 | 734.83 | 2584.37 | 0.28 | w0553 |
| 213.09 | 433.84 | 0.49 | w1426 | 136.41 | 525.28 | 0.26 | w1426 |
| 28409.79 | 32349.40 | 0.88 | glpT | 25094.68 | 97868.64 | 0.26 | glpT |
| 271.65 | 813.15 | 0.33 | sapC | 354.68 | 1417.55 | 0.25 | sapC |
| 1502.52 | 1107.42 | 1.36 | w2597 | 631.01 | 2727.88 | 0.23 | w2597 |
| 274.59 | 176.87 | 1.55 | ais | 706.69 | 3093.84 | 0.23 | ais |
| 191.80 | 216.29 | 0.89 | cefA | 864.54 | 3806.84 | 0.23 | celA |
| 109.10 | 59.92 | 1.82 | ppdB | 38.01 | 182.15 | 0.21 | ppdB |
| 249.88 | 204.52 | 1.22 | agaC | 80.45 | 386.08 | 0.21 | agaC |
| 56.62 | 13.68 | 4.14 | hrpA | 546.07 | 2814.78 | 0.19 | hrpA |
| 182.61 | 92.19 | 1.98 | tdcR | 62.07 | 330.94 | 0.19 | tdcR |
| 5374.56 | 5767.37 | 0.93 | spoU | 10944.76 | 60533.88 | 0.18 | spoU |
| 456.55 | 279.26 | 1.63 | w0549 | 956.45 | 5470.42 | 0.17 | w0549 |
| 195.25 | 128.74 | 1.52 | agaW | 77.80 | 464.51 | 0.17 | agaW |
| 556.82 | 343.19 | 1.62 | w0548 | 783.67 | 4816.90 | 0.16 | w0548 |
| 177.02 | 182.96 | 0.97 | alpA | 37.14 | 237.77 | 0.16 | alpA |
| 230.79 | 63.00 | 3.66 | hybF | 85.60 | 616.14 | 0.14 | hybF |

Gene names written in bold letters are SOS response genes; M15: 15 min exposure to MMC; M40: 40 min exposure to MMC

TABLE 7

Gene expressions in DM800 and DM803 when exposed to MMC

| Gene name | b number | DM800 MMC | control | ratio | DM803 MMC | DM803 control | ratio |
|---|---|---|---|---|---|---|---|
| recN | | 98536.3 | 11895.5 | 8.3 | 2454.6 | 2089.9 | 1.2 |
| hslS | | 11287.9 | 1677.7 | 6.7 | 426.0 | 370.9 | 1.1 |
| dinI | | 10515.2 | 1564.7 | 6.7 | 780.0 | 516.8 | 1.5 |
| sulA | | 13936.2 | 2416.8 | 5.8 | 1167.7 | 801.5 | 1.5 |
| w1816 | b1848 | 18614.3 | 3231.0 | 5.8 | 124.7 | 900.3 | 0.1 |
| hslT | | 21578.6 | 5358.3 | 4.0 | 1486.7 | 962.6 | 1.5 |
| lexA | | 22768.8 | 6375.1 | 3.6 | 2935.3 | 2950.2 | 1.0 |
| w0522 | b0531 | 8750.6 | 2628.4 | 3.3 | 1299.3 | 752.0 | 1.7 |
| w1815 | b1847 | 16206.3 | 4874.5 | 3.3 | 236.0 | 660.6 | 0.4 |
| w2141 | b2181 | 2156.1 | 691.5 | 3.1 | 0.0 | 934.4 | 0.0 |
| recA | | 34375.8 | 11386.6 | 3.0 | 8505.3 | 6677.0 | 1.3 |
| smpA | | 1614.6 | 558.5 | 2.9 | 591.3 | 624.8 | 0.9 |
| cspA | | 12566.2 | 4347.9 | 2.9 | 52966.2 | 42356.6 | 1.3 |
| ecpD | | 227.5 | 80.4 | 2.8 | 384.4 | 287.9 | 1.3 |
| w3019 | b3080 | 802.6 | 288.9 | 2.8 | 970.7 | 621.6 | 1.6 |
| w2878 | b2939 | 1151.8 | 439.8 | 2.6 | 0.0 | 373.7 | 0.0 |
| entD | | 491.1 | 189.4 | 2.6 | 491.6 | 328.8 | 1.5 |
| fhuC | | 818.1 | 321.7 | 2.5 | 964.7 | 712.6 | 1.4 |
| w1201 | b1228 | 4623.0 | 1874.2 | 2.5 | 2598.3 | 2567.4 | 1.0 |
| w2999 | b3059 | 1710.6 | 709.1 | 2.4 | 1279.4 | 1182.6 | 1.1 |
| caiB | | 326.5 | 139.5 | 2.3 | 834.2 | 806.6 | 1.0 |
| infA | | 8186.4 | 3504.9 | 2.3 | 2964.1 | 3046.5 | 1.0 |
| uvrA | | 33530.3 | 14452.9 | 2.3 | 6731.4 | 5941.1 | 1.1 |
| w2879 | b2940 | 3946.5 | 1727.3 | 2.3 | 281.8 | 1248.5 | 0.2 |
| insB2 | | 6522.2 | 2894.3 | 2.3 | 4566.2 | 4307.9 | 1.1 |
| dinD | | 5316.7 | 2385.6 | 2.2 | 3182.2 | 2522.4 | 1.3 |
| secG | | 6754.2 | 3076.6 | 2.2 | 9867.2 | 8993.5 | 1.1 |
| priC | | 341.8 | 156.1 | 2.2 | 1151.2 | 509.8 | 2.3 |
| w0561 | b0571 | 11989.7 | 5479.4 | 2.2 | 0.0 | 636.5 | 0.0 |
| exbD | | 7165.4 | 3289.3 | 2.2 | 1867.7 | 1621.7 | 1.2 |
| umuC | | 5697.9 | 2659.8 | 2.1 | 1014.3 | 908.3 | 1.1 |
| mioC | | 8113.1 | 3804.3 | 2.1 | 3218.1 | 2444.7 | 1.3 |
| insB_1 | | 6065.0 | 2854.2 | 2.1 | 45332 | 4432.3 | 1.0 |
| trkH | | 17795.3 | 8430.8 | 2.1 | 2293.2 | 1959.1 | 1.2 |
| w1345 | b1374 | 1026.3 | 487.6 | 2.1 | 0.0 | 522.9 | 0.0 |
| dniR | | 1878.7 | 900.0 | 2.1 | 1427.1 | 899.9 | 1.6 |
| uvrB | | 14508.7 | 6960.8 | 2.1 | 5425.4 | 5179.7 | 1.0 |
| insA_4 | | 2298.2 | 1111.8 | 2.1 | 939.3 | 1747.8 | 0.5 |
| ruvA | | 10492.5 | 5134.4 | 2.0 | 1819.4 | 1918.2 | 0.9 |
| appY | | 815.1 | 400.3 | 2.0 | 593.1 | 340.6 | 1.7 |
| xseA | | 13206.6 | 6494.6 | 2.0 | 17733.8 | 8677.0 | 2.0 |
| w0224 | b0231 | 6686.9 | 3310.7 | 2.0 | 2353.4 | 1760.8 | 1.3 |
| w3139 | b3199 | 11174.8 | 5555.3 | 2.0 | 2171.5 | 3228.1 | 0.7 |
| w2512 | b2559 | 24511.0 | 12207.1 | 2.0 | 1537.4 | 1511.4 | 1.0 |
| entF | | 179.8 | 91.5 | 2.0 | 494.1 | 339.5 | 1.5 |
| glnK | | 408.6 | 208.4 | 2.0 | 571.9 | 212.8 | 2.7 |
| insB_4 | | 6575.4 | 3364.4 | 2.0 | 2823.1 | 2738.2 | 1.0 |
| rnpA | | 5250.2 | 2686.3 | 2.0 | 1722.3 | 2000.1 | 0.9 |
| pheP | | 2467.2 | 1263.6 | 2.0 | 2974.0 | 2187.8 | 1.4 |
| w0491 | b0500 | 508.2 | 925.1 | 0.5 | 176.3 | 96.9 | 1.8 |
| w4088 | b4183 | 384.5 | 701.1 | 0.5 | 777.9 | 583.0 | 1.3 |
| w0570 | b0580 | 1956.2 | 3578.9 | 0.5 | 867.8 | 197.6 | 4.4 |
| w0221 | b0228 | 1612.4 | 2950.5 | 0.5 | 326.2 | 420.6 | 0.8 |
| w1347 | b1376 | 5383.3 | 9852.6 | 0.5 | 1194.3 | 1736.1 | 0.7 |
| rem | | 540.5 | 989.7 | 0.5 | 0.0 | 0.0 | |
| xylF | | 2117.7 | 3885.5 | 0.5 | 4289.6 | 3178.7 | 1.3 |
| w2284 | b2325 | 452.5 | 830.6 | 0.5 | 894.8 | 911.0 | 1.0 |
| w0627 | b0637 | 1984.5 | 3647.0 | 0.5 | 0.0 | 299.3 | 0.0 |
| nlp | | 487.4 | 895.9 | 0.5 | 1004.9 | 549.6 | 1.8 |
| w2940 | b3001 | 3777.0 | 6949.2 | 0.5 | 2725.9 | 1950.7 | 1.4 |
| w0591 | b0601 | 1658.1 | 3060.6 | 0.5 | 602.0 | 402.6 | 1.5 |
| w0270 | b0278 | 1175.1 | 2170.8 | 0.5 | 493.9 | 428.3 | 1.2 |
| w2790 | b2849 | 455.2 | 841.4 | 0.5 | 489.3 | 455.5 | 1.1 |
| pyrI | | 1174.7 | 2171.6 | 0.5 | 752.3 | 509.1 | 1.5 |
| w1018 | b1045 | 2359.6 | 4364.5 | 0.5 | 525.2 | 272.8 | 1.9 |
| w2709 | b2767 | 1312.2 | 2440.9 | 0.5 | 597.4 | 383.4 | 1.6 |
| w2329 | b2371 | 594.8 | 1107.2 | 0.5 | 861.9 | 690.9 | 1.2 |
| aidB | | 12189 | 2269.2 | 0.5 | 4969.4 | 3102.9 | 1.6 |
| w2791 | b2850 | 773.2 | 1441.3 | 0.5 | 508.9 | 523.1 | 1.0 |
| w2605 | b2659 | 6211.7 | 11600.3 | 0.5 | 3614.2 | 2885.4 | 1.3 |
| cmtB | | 141.2 | 263.8 | 0.5 | 275.0 | 164.4 | 1.7 |
| w3890 | b3975 | 824.3 | 1541.5 | 0.5 | 607.0 | 403.6 | 1.5 |
| gntV | | 1242.4 | 2324.3 | 0.5 | 311.4 | 446.1 | 0.7 |
| aspA | | 92135.1 | 173324.7 | 0.5 | 10420.0 | 16655.6 | 0.6 |
| w3210 | b3268 | 479.3 | 903.6 | 0.5 | 551.4 | 372.6 | 1.5 |
| w0271 | b0279 | 792.9 | 1496.9 | 0.5 | 471.2 | 426.9 | 1.1 |
| w1003 | b1029 | 2145.7 | 4051.8 | 0.5 | 2.6 | 0.0 | |
| w1017 | b1044 | 1431.3 | 2703.5 | 0.5 | 1035.5 | 413.5 | 2.5 |
| feoA | | 470.5 | 888.8 | 0.5 | 1313.4 | 1090.4 | 1.2 |
| chpS | | 1657.3 | 3141.1 | 0.5 | 568.1 | 558.4 | 1.0 |
| w0619 | b0629 | 2054.3 | 3896.8 | 0.5 | 289.0 | 43.4 | 6.7 |
| yjjM | b4357 | 1966.9 | 3732.7 | 0.5 | 2090.3 | 1457.0 | 1.4 |

TABLE 7-continued

Gene expressions in DM800 and DM803 when exposed to MMC

| Gene name | b number | DM800 MMC | control | ratio | DM803 MMC | DM803 control | ratio |
|---|---|---|---|---|---|---|---|
| w2816 | b2876 | 1687.7 | 3205.6 | 0.5 | 1046.1 | 858.8 | 1.2 |
| w3272 | b3337 | 587.3 | 1115.5 | 0.5 | 430.3 | 359.9 | 1.2 |
| w3443 | b3507 | 446.9 | 849.1 | 0.5 | 591.4 | 598.3 | 1.0 |
| w0351 | b0359 | 1435.0 | 2731.1 | 0.5 | 0.0 | 72.1 | 0.0 |
| w1527 | b1556 | 253.0 | 482.4 | 0.5 | 726.3 | 421.9 | 1.7 |
| w0263 | b0271 | 955.9 | 1824.5 | 0.5 | 484.0 | 330.6 | 1.5 |
| csgA | | 522.9 | 998.6 | 0.5 | 703.7 | 599.6 | 1.2 |
| fimZ | | 536.1 | 1024.6 | 0.5 | 424.3 | 343.7 | 1.2 |
| w2314 | b2356 | 581.8 | 1113.3 | 0.5 | 1114.7 | 731.5 | 1.5 |
| w2596 | b2649 | 370.7 | 710.0 | 0.5 | 1024.4 | 605.2 | 1.7 |
| yigJ | b3823 | 542.9 | 1039.7 | 0.5 | 1372.3 | 817.5 | 1.7 |
| w1025 | b1052 | 1003.1 | 1922.7 | 0.5 | 177.0 | 90.5 | 2.0 |
| w1359 | b1388 | 2953.5 | 5661.9 | 0.5 | 328.5 | 262.2 | 1.3 |
| w0673 | b0690 | 1558.5 | 2992.7 | 0.5 | 249.4 | 313.2 | 0.8 |
| fixX | | 313.0 | 601.3 | 0.5 | 1259.9 | 891.9 | 1.4 |
| w4093 | b4188 | 953.2 | 1839.0 | 0.5 | 901.6 | 606.7 | 1.5 |
| w0674 | b0691 | 1466.3 | 2840.2 | 0.5 | 129.0 | 350.8 | 0.4 |
| w2400 | b2447 | 1214.0 | 2355.8 | 0.5 | 810.8 | 406.3 | 2.0 |
| w1963 | b2004 | 537.0 | 1043.7 | 0.5 | 667.7 | 598.5 | 1.1 |
| w3974 | b4066 | 455.1 | 884.6 | 0.5 | 816.0 | 462.9 | 1.8 |
| w1242 | b1271 | 3047.5 | 5958.6 | 0.5 | 1870.6 | 336.3 | 5.6 |
| w0525 | b0534 | 930.8 | 1822.0 | 0.5 | 829.3 | 490.0 | 1.7 |
| w4132 | b4227 | 1602.0 | 3151.2 | 0.5 | 3125.1 | 2509.8 | 1.2 |
| w3304 | b3369 | 428.9 | 850.8 | 0.5 | 728.3 | 701.9 | 1.0 |
| w2228 | b2269 | 272.0 | 540.0 | 0.5 | 482.1 | 399.3 | 1.2 |
| chaB | | 721.8 | 1433.4 | 0.5 | 177.0 | 0.0 | |
| cydA | | 699.9 | 1392.5 | 0.5 | 963.9 | 305.9 | 3.2 |
| melR | | 5082.0 | 10140.2 | 0.5 | 1511.6 | 1528.2 | 1.0 |
| w1004 | b1030 | 1265.7 | 2528.7 | 0.5 | 27.8 | 163.0 | 0.2 |
| hofG | | 315.2 | 630.0 | 0.5 | 694.2 | 767.7 | 0.9 |
| w1429 | b1458 | 360.8 | 721.2 | 0.5 | 711.8 | 488.3 | 1.5 |
| w0299 | b0307 | 9464.0 | 18943.1 | 0.5 | 2048.3 | 2846.3 | 0.7 |
| rpiR | | 748.7 | 1502.6 | 0.5 | 536.3 | 419.6 | 1.3 |
| celD | | 2009.3 | 4041.7 | 0.5 | 1094.3 | 303.1 | 3.6 |
| w0801 | b0825 | 2801.7 | 5636.8 | 0.5 | 920.2 | 417.5 | 2.2 |
| w0241 | b0249 | 712.2 | 1434.3 | 0.5 | 772.1 | 649.4 | 1.2 |
| w0621 | b0631 | 1293.5 | 2605.4 | 0.5 | 0.0 | 170.6 | 0.0 |
| putP | | 12834.1 | 25859.7 | 0.5 | 5693.7 | 6221.7 | 0.9 |
| w4099 | b4194 | 377.9 | 764.4 | 0.5 | 709.5 | 539.0 | 1.3 |
| prsA | | 535.4 | 1091.6 | 0.5 | 24.5 | 0.0 | |
| hybD | | 177.8 | 363.8 | 0.5 | 510.9 | 573.9 | 0.9 |
| sapB | | 501.3 | 1027.1 | 0.5 | 258.8 | 0.0 | |
| w3821 | b3901 | 412.4 | 845.8 | 0.5 | 945.9 | 539.7 | 1.8 |
| w1459 | b1488 | 417.7 | 857.7 | 0.5 | 994.9 | 740.6 | 1.3 |
| agaD | | 222.7 | 459.0 | 0.5 | 966.6 | 465.2 | 2.1 |
| ccmD | | 646.1 | 1332.0 | 0.5 | 92.3 | 64.5 | 1.4 |
| cpsG | | 1070.1 | 2212.1 | 0.5 | 0.0 | 8.9 | 0.0 |
| relB | | 1002.3 | 2072.5 | 0.5 | 0.0 | 92.3 | 0.0 |
| w2809 | b2869 | 3556.9 | 7365.3 | 0.5 | 1264.0 | 1453.8 | 0.9 |
| w0824 | b0848 | 1242.8 | 2590.0 | 0.5 | 370.9 | 350.1 | 1.1 |
| osmE | | 2901.6 | 6072.9 | 0.5 | 350.0 | 900.3 | 0.4 |
| w0362 | b0370 | 1234.6 | 2593.0 | 0.5 | 0.0 | 0.0 | |
| w1927 | b1963 | 481.3 | 1014.0 | 0.5 | 824.4 | 612.6 | 1.3 |
| w0211 | b0218 | 639.9 | 1353.7 | 0.5 | 198.7 | 321.6 | 0.6 |
| w0237 | b0245 | 855.9 | 1815.7 | 0.5 | 355.4 | 461.1 | 0.8 |
| w2592 | b2645 | 586.0 | 1247.1 | 0.5 | 1032.5 | 566.6 | 1.8 |
| phnH | | 987.7 | 2147.0 | 0.5 | 1103.3 | 937.7 | 1.2 |
| flgA | | 577.4 | 1255.7 | 0.5 | 1482.3 | 1396.3 | 1.1 |
| w2595 | b2648 | 377.1 | 821.4 | 0.5 | 647.4 | 431.6 | 1.5 |
| w2600 | b2654 | 792.5 | 1732.9 | 0.5 | 222.5 | 309.6 | 0.7 |
| pheL | | 93.3 | 205.1 | 0.5 | 256.4 | 258.7 | 1.0 |
| w3049 | b3107 | 1146.6 | 2524.7 | 0.5 | 53.4 | 180.9 | 0.3 |
| w1031 | b1058 | 1045.4 | 2305.9 | 0.5 | 188.9 | 101.9 | 1.9 |
| w0295 | b0303 | 473.5 | 1045.0 | 0.5 | 468.2 | 461.2 | 1.0 |
| marB | | 872.9 | 1928.8 | 0.5 | 843.0 | 130.7 | 6.5 |
| w0665 | b0682 | 786.7 | 1744.6 | 0.5 | 0.0 | 592.3 | 0.0 |
| w1016 | b1043 | 1399.6 | 3109.1 | 0.5 | 419.6 | 203.5 | 2.1 |
| w0298 | b0306 | 8569.6 | 19066.7 | 0.4 | 1722.6 | 2401.5 | 0.7 |
| w0812 | b0836 | 1381.4 | 3073.9 | 0.4 | 356.8 | 314.2 | 1.1 |
| w2026 | b2067 | 1456.5 | 3270.0 | 0.4 | 22.0 | 337.9 | 0.1 |
| w0715 | b0732 | 1050.7 | 2361.6 | 0.4 | 154.8 | 30.1 | 5.1 |
| pyrL | | 689.6 | 1552.6 | 0.4 | 520.5 | 338.7 | 1.5 |
| menE | | 1802.6 | 4058.7 | 0.4 | 4640.7 | 928.2 | 5.0 |
| rnb | | 703.1 | 1594.1 | 0.4 | 399.4 | 0.0 | |
| fucR | | 1770.9 | 4026.5 | 0.4 | 2264.4 | 1572.6 | 1.4 |
| w2818 | b2878 | 278.7 | 634.2 | 0.4 | 787.6 | 511.9 | 1.5 |
| acpD | | 1990.2 | 4539.4 | 0.4 | 0.0 | 287.0 | 0.0 |
| w0489 | b0498 | 332.5 | 758.7 | 0.4 | 137.3 | 183.4 | 0.7 |
| ppdA | | 177.3 | 405.0 | 0.4 | 662.6 | 505.3 | 1.3 |
| w1966 | b2007 | 488.9 | 1118.3 | 0.4 | 1163.2 | 680.8 | 1.7 |
| "no template" | | 333.4 | 764.2 | 0.4 | 470.2 | 368.3 | 1.3 |
| w2401 | b2448 | 1085.4 | 2497.9 | 0.4 | 1160.0 | 715.4 | 1.6 |
| w4094 | b4189 | 1505.9 | 3477.9 | 0.4 | 1022.3 | 932.0 | 1.1 |
| dicC | | 543.4 | 1266.3 | 0.4 | 319.5 | 67.2 | 4.8 |
| w0286 | b0294 | 844.0 | 1986.6 | 0.4 | 498.7 | 447.4 | 1.1 |
| selB | | 341.9 | 808.9 | 0.4 | 7781.6 | 7090.5 | 1.1 |
| w2733 | b2789 | 3589.0 | 8496.9 | 0.4 | 5638.1 | 3562.2 | 1.6 |
| "no template" | | 301.6 | 716.0 | 0.4 | 408.2 | 329.1 | 1.2 |
| trpC | | 10007.8 | 23940.6 | 0.4 | 421.9 | 2562.2 | 0.2 |
| relF | | 449.8 | 1077.5 | 0.4 | 0.0 | 0.0 | |
| w1318 | b1347 | 1107.0 | 2655.3 | 0.4 | 1.4 | 308.5 | 0.0 |
| agaV | | 202.3 | 490.1 | 0.4 | 673.0 | 669.2 | 1.0 |
| w1002 | b1028 | 1315.8 | 3189.3 | 0.4 | 288.3 | 62.7 | 4.6 |
| w0685 | b0702 | 1124.7 | 2728.6 | 0.4 | 198.6 | 229.5 | 0.9 |
| potH | | 500.1 | 1228.0 | 0.4 | 641.9 | 243.8 | 2.6 |
| w2399 | b2446 | 853.3 | 2107.1 | 0.4 | 770.2 | 485.4 | 1.6 |
| metA | | 991.4 | 2449.4 | 0.4 | 2026.6 | 1816.4 | 1.1 |
| lytB | | 311.0 | 770.5 | 0.4 | 353.9 | 181.5 | 1.9 |
| w2987 | b3047 | 638.0 | 1593.1 | 0.4 | 509.8 | 303.9 | 1.7 |
| w0552 | b0562 | 1225.7 | 3084.4 | 0.4 | 0.0 | 588.7 | 0.0 |
| w1846 | b1878 | 382.4 | 968.1 | 0.4 | 1322.3 | 1154.7 | 1.1 |
| dicB | | 533.3 | 1351.9 | 0.4 | 260.1 | 54.8 | 4.7 |
| w1005 | b1031 | 970.4 | 2465.9 | 0.4 | 0.0 | 106.0 | 0.0 |
| w2587 | b2640 | 509.5 | 1301.7 | 0.4 | 557.1 | 371.8 | 1.5 |
| w1260 | b1289 | 963.5 | 2507.3 | 0.4 | 0.0 | 353.6 | 0.0 |
| w3068 | b3127 | 12241.5 | 31901.4 | 0.4 | 2383.9 | 3185.5 | 0.7 |
| w0551 | b0561 | 2143.7 | 5619.4 | 0.4 | 477.1 | 864.7 | 0.6 |
| w2599 | b2653 | 616.9 | 1633.9 | 0.4 | 456.5 | 107.8 | 4.2 |
| w0569 | b0579 | 912.6 | 2444.1 | 0.4 | 673.5 | 612.3 | 1.1 |
| fruR | | 7146.3 | 19274.4 | 0.4 | 2076.3 | 2369.5 | 0.9 |
| w3927 | b4020 | 1323.8 | 3637.0 | 0.4 | 2685.9 | 2131.9 | 1.3 |
| w3069 | b3128 | 15445.7 | 42484.5 | 0.4 | 499.8 | 1153.3 | 0.4 |
| w0162 | b0162 | 5614.0 | 15712.2 | 0.4 | 4564.1 | 3889.2 | 1.2 |
| w0564 | b0574 | 1311.4 | 3713.2 | 0.4 | 584.5 | 175.8 | 3.3 |
| lar | | 367.2 | 1045.3 | 0.4 | 82.1 | 122.0 | 0.7 |
| agaB | | 174.8 | 500.9 | 0.3 | 371.8 | 504.1 | 0.7 |
| w0356 | b0364 | 893.8 | 2593.5 | 0.3 | 10.4 | 32.6 | 0.3 |
| ptrB | | 583.6 | 1710.7 | 0.3 | 246.4 | 69.2 | 3.6 |
| tdcA | | 140.7 | 420.2 | 0.3 | 612.3 | 343.6 | 1.8 |
| w0005 | b0005 | 854.5 | 2591.3 | 0.3 | 442.3 | 388.2 | 1.1 |
| w2820 | b2880 | 711.7 | 2231.6 | 0.3 | 904.4 | 609.4 | 1.5 |
| racC | | 145.6 | 474.0 | 0.3 | 167.4 | 26.9 | 6.2 |
| w1323 | b1352 | 814.1 | 2717.5 | 0.3 | 297.1 | 235.6 | 1.3 |
| tolQ | | 7715.8 | 26048.3 | 0.3 | 1213.4 | 1001.3 | 1.2 |
| w0535 | b0545 | 238.5 | 834.4 | 0.3 | 114.4 | 162.5 | 0.7 |
| w2546 | b2597 | 13321.2 | 46691.6 | 0.3 | 2567.6 | 4164.9 | 0.6 |
| w0553 | b0563 | 734.8 | 2584.4 | 0.3 | 0.0 | 277.1 | 0.0 |
| w1426 | b1455 | 136.4 | 525.3 | 0.3 | 672.5 | 358.6 | 1.9 |
| glpT | | 25094.7 | 97868.6 | 0.3 | 7769.7 | 14648.6 | 0.5 |
| sapC | | 354.7 | 1417.6 | 0.3 | 546.0 | 0.0 | |
| w2597 | b2650 | 631.0 | 2727.9 | 0.2 | 1000.0 | 566.4 | 1.8 |
| ais | | 706.7 | 3093.8 | 0.2 | 352.9 | 114.6 | 3.1 |
| celA | | 864.5 | 3806.8 | 0.2 | 0.0 | 512.6 | 0.0 |
| ppdB | | 38.0 | 182.1 | 0.2 | 399.9 | 345.8 | 1.2 |
| agaC | | 80.5 | 386.1 | 0.2 | 598.1 | 602.8 | 1.0 |
| hrpA | | 546.1 | 2814.8 | 0.2 | 0.0 | 147.3 | 0.0 |
| tdcR | | 62.1 | 330.9 | 0.2 | 350.0 | 232.7 | 1.5 |
| spoU | | 10944.8 | 60533.9 | 0.2 | 4024.5 | 3163.9 | 1.3 |
| w0549 | b0559 | 956.6 | 5470.4 | 0.2 | 115.5 | 287.2 | 0.4 |
| agaW | | 77.8 | 464.5 | 0.2 | 479.9 | 779.3 | 0.6 |
| w0548 | b0558 | 783.7 | 4816.9 | 0.2 | 327.8 | 85.0 | 3.9 |
| alpA | | 37.1 | 237.7 | 0.2 | 366.3 | 269.2 | 1.4 |
| hybF | | 85.6 | 616.1 | 0.1 | 332.8 | 456.6 | 0.7 |

TABLE 8

Gene expressions in DM800 and DM803 when exposed to MMC

| Gene name | b # | DM800-MMC | DM800-control | DM800 ratio (MMC/control) | DM803-MMC | DM803-control | DM803 ratio (MMC/control) |
|---|---|---|---|---|---|---|---|
| chaB | | 721.8 | 1433.4 | 0.5 | 177.0 | 0.0 | |
| gusC | | 1069.6 | 1178.1 | 0.9 | 39.2 | 0.0 | |
| prsA | | 535.4 | 1091.6 | 0.5 | 24.5 | 0.0 | |
| rnb | | 703.1 | 1594.1 | 0.4 | 399.4 | 0.0 | |
| rspB | | 987.2 | 1520.0 | 0.6 | 480.4 | 0.0 | |
| sapB | | 501.3 | 1027.1 | 0.5 | 258.8 | 0.0 | |
| sapC | | 354.7 | 1417.6 | 0.3 | 546.0 | 0.0 | |
| uxaB | | 2051.4 | 2423.2 | 0.8 | 527.4 | 0.0 | |
| w0367 | b0375 | 1010.4 | 1827.8 | 0.6 | 179.0 | 0.0 | |
| w0492 | b0501 | 717.2 | 769.2 | 0.9 | 85.3 | 0.0 | |
| w0521 | b0530 | 425.3 | 746.2 | 0.6 | 169.9 | 0.0 | |
| w0537 | b0547 | 711.1 | 851.5 | 0.8 | 87.9 | 0.0 | |
| w0544 | b0554 | 602.7 | 558.1 | 1.1 | 98.8 | 0.0 | |
| w1114 | b1141 | 1523.8 | 1839.4 | 0.8 | 30.1 | 0.0 | |
| w0508 | b0517 | 2160.9 | 2528.0 | 0.9 | 480.7 | 1.0 | 457.9 |
| w0541 | b0551 | 542.2 | 591.7 | 0.9 | 140.0 | 7.6 | 18.4 |
| molR | | 4939.4 | 4515.9 | 1.1 | 5518.5 | 513.6 | 10.7 |
| w2514 | b2561 | 7715.4 | 7319.4 | 1.1 | 23955.8 | 2367.6 | 10.1 |
| molR | | 3903.5 | 3852.3 | 1.0 | 2355.4 | 243.6 | 9.7 |
| w1329 | b1358 | 1909.4 | 1872.1 | 1.0 | 649.0 | 75.2 | 8.6 |
| w1381 | b1410 | 2104.8 | 1895.7 | 1.1 | 2603.5 | 309.6 | 8.4 |
| w1088 | b1115 | 3071.3 | 4218.6 | 0.7 | 1543.9 | 184.8 | 8.4 |
| dsdX | | 2030.3 | 2282.9 | 0.9 | 1833.5 | 227.0 | 8.1 |
| thrS | | 277.1 | 318.4 | 0.9 | 1498.9 | 196.8 | 7.6 |
| w0873 | b0898 | 2210.6 | 1636.1 | 1.4 | 1001.4 | 132.9 | 7.5 |
| w0617 | b0627 | 4834.3 | 7145.9 | 0.7 | 2171.5 | 301.1 | 7.2 |
| w3258 | b3323 | 4107.7 | 3439.8 | 1.2 | 9485.3 | 1318.6 | 7.2 |
| w0999 | b1025 | 1233.1 | 888.5 | 1.4 | 199.5 | 28.3 | 7.1 |
| rspA | | 1862.1 | 2002.0 | 0.9 | 1297.2 | 191.4 | 6.8 |
| w0843 | b0867 | 2593.1 | 2957.8 | 0.9 | 1333.5 | 197.9 | 6.7 |
| w0619 | b0629 | 2054.3 | 3896.8 | 0.5 | 289.0 | 43.4 | 6.7 |
| marB | | 872.9 | 1928.8 | 0.5 | 843.0 | 130.7 | 6.5 |
| w1128 | b1155 | 865.4 | 1384.1 | 0.6 | 157.3 | 24.8 | 6.3 |
| napH | | 1548.4 | 1771.5 | 0.9 | 2445.8 | 392.2 | 6.2 |
| racC | | 145.6 | 474.0 | 0.3 | 167.4 | 26.9 | 6.2 |
| w1266 | b1295 | 1834.3 | 3178.5 | 0.6 | 1111.8 | 178.6 | 6.2 |
| w2857 | b2918 | 2013.5 | 2025.3 | 1.0 | 2905.4 | 475.0 | 6.1 |
| pfkB | | 5266.9 | 4949.8 | 1.1 | 1148.4 | 188.9 | 6.1 |
| w1309 | b1338 | 3612.6 | 4271.9 | 0.8 | 3943.9 | 660.9 | 6.0 |
| napG | | 4522.3 | 4522.5 | 1.0 | 5243.5 | 900.1 | 5.8 |
| w1242 | b1271 | 3047.5 | 5958.6 | 0.5 | 1870.6 | 336.3 | 5.6 |
| w0991 | b1017 | 2292.7 | 1982.0 | 1.2 | 564.2 | 101.9 | 5.5 |
| vsr | | 5927.8 | 3617.9 | 1.6 | 3758.3 | 687.4 | 5.5 |
| w0996 | b1022 | 954.0 | 881.7 | 1.1 | 406.4 | 74.4 | 5.5 |
| w0957 | b0983 | 1903.7 | 1772.1 | 1.1 | 1280.4 | 234.3 | 5.5 |
| w1287 | b1316 | 4404.7 | 4724.2 | 0.9 | 481.3 | 89.0 | 5.4 |
| w1113 | b1140 | 2063.9 | 2466.4 | 0.8 | 1674.5 | 315.1 | 5.3 |
| w1168 | b1195 | 1068.7 | 1662.1 | 0.6 | 105.1 | 19.9 | 5.3 |
| w0918 | b0943 | 964.3 | 1122.4 | 0.9 | 166.1 | 31.9 | 5.2 |
| hslJ | | 1701.0 | 1353.6 | 1.3 | 952.9 | 183.4 | 5.2 |
| fdnH | | 2916.7 | 3353.8 | 0.9 | 1551.5 | 299.3 | 5.2 |
| w0715 | b0732 | 1050.7 | 2361.6 | 0.4 | 154.8 | 30.1 | 5.1 |
| menE | | 1802.6 | 4058.7 | 0.4 | 4640.7 | 928.2 | 5.0 |
| w0511 | b0520 | 2664.2 | 3109.8 | 0.9 | 2221.0 | 452.5 | 4.9 |
| w2508 | b2555 | 3575.2 | 2467.8 | 1.4 | 5237.2 | 1078.9 | 4.9 |
| pspC | | 670.6 | 809.3 | 0.8 | 370.0 | 76.5 | 4.8 |
| w0767 | b0791 | 2562.9 | 3359.1 | 0.8 | 2376.4 | 497.9 | 4.8 |
| dicC | | 543.4 | 1266.3 | 0.4 | 319.5 | 67.2 | 4.8 |
| dicB | | 533.3 | 1351.9 | 0.4 | 260.1 | 54.8 | 4.7 |
| chaC | | 3102.1 | 3008.4 | 1.0 | 1480.1 | 314.6 | 4.7 |
| w0387 | b0395 | 2772.4 | 3361.1 | 0.8 | 1676.5 | 362.0 | 4.6 |
| w0986 | b1012 | 1670.0 | 1494.6 | 1.1 | 1627.0 | 352.8 | 4.6 |
| w1002 | b1028 | 1315.8 | 3189.3 | 0.4 | 288.3 | 62.7 | 4.6 |
| w0570 | b0580 | 1956.2 | 3578.9 | 0.5 | 867.8 | 197.6 | 4.4 |
| w1972 | b2013 | 2191.0 | 2234.9 | 1.0 | 1878.6 | 435.2 | 4.3 |
| gatR | | 16844.2 | 12487.4 | 1.3 | 2559.5 | 598.3 | 4.3 |
| w2582 | b2634 | 3769.3 | 4821.9 | 0.8 | 3379.2 | 793.9 | 4.3 |
| w2599 | b2653 | 616.9 | 1633.9 | 0.4 | 456.5 | 107.8 | 4.2 |
| w0793 | b0817 | 9409.7 | 8201.4 | 1.1 | 8721.9 | 2060.6 | 4.2 |
| w3260 | b3325 | 1313.1 | 1350.2 | 1.0 | 544.2 | 131.4 | 4.1 |
| w0888 | b0913 | 3553.0 | 2732.1 | 1.3 | 3682.2 | 899.6 | 4.1 |
| w0446 | b0454 | 1294.0 | 1873.1 | 0.7 | 1977.3 | 483.5 | 4.1 |
| xthA | | 7322.0 | 7765.8 | 0.9 | 3014.3 | 750.9 | 4.0 |
| w2574 | b2626 | 1092.4 | 1842.3 | 0.6 | 1984.7 | 494.8 | 4.0 |

TABLE 8-continued

Gene expressions in DM800 and DM803 when exposed to MMC

| Gene name | b # | DM800-MMC | DM800-control | DM800 ratio (MMC/control) | DM803-MMC | DM803-control | DM803 ratio (MMC/control) |
|---|---|---|---|---|---|---|---|
| w1211 | b1240 | 2015.0 | 1589.9 | 1.3 | 685.0 | 171.1 | 4.0 |
| btuC | | 5381.6 | 3197.6 | 1.7 | 3189.6 | 804.9 | 4.0 |
| osmB | | 1731.8 | 2164.1 | 0.8 | 1092.6 | 281.1 | 3.9 |
| w1308 | b1337 | 1961.3 | 2585.3 | 0.8 | 2106.4 | 544.5 | 3.9 |
| w1210 | b1239 | 1397.2 | 1027.0 | 1.4 | 1996.6 | 516.3 | 3.9 |
| w0616 | b0626 | 2728.7 | 3046.4 | 0.9 | 840.4 | 217.6 | 3.9 |
| w0548 | b0558 | 783.7 | 4816.9 | 0.2 | 327.8 | 85.0 | 3.9 |
| dsrB | | 803.9 | 1220.8 | 0.7 | 1792.6 | 471.9 | 3.8 |
| w1382 | b1411 | 2709.0 | 2309.7 | 1.2 | 2107.7 | 554.9 | 3.8 |
| alkB | | 1424.0 | 1719.3 | 0.8 | 437.2 | 115.3 | 3.8 |
| pyrF | | 4511.4 | 3724.1 | 1.2 | 3376.5 | 903.9 | 3.7 |
| w1292 | b1321 | 12154.3 | 8766.6 | 1.4 | 1109.1 | 305.2 | 3.6 |
| w1331 | b1360 | 2085.1 | 2530.6 | 0.8 | 1174.9 | 324.1 | 3.6 |
| w0764 | b0788 | 2579.2 | 2813.6 | 0.9 | 2474.3 | 682.9 | 3.6 |
| mcrA | | 2912.9 | 3609.3 | 0.8 | 476.8 | 132.0 | 3.6 |
| celD | | 2009.3 | 4041.7 | 0.5 | 1094.3 | 303.1 | 3.6 |
| w3213 | b3271 | 1521.2 | 1151.6 | 1.3 | 2042.2 | 570.1 | 3.6 |
| w0998 | b1024 | 2410.5 | 1957.8 | 1.2 | 2866.7 | 803.1 | 3.6 |
| ptrB | | 583.6 | 1710.7 | 0.3 | 246.4 | 69.2 | 3.6 |
| malY | | 3296.2 | 3398.9 | 1.0 | 876.6 | 250.7 | 3.5 |
| prfH | | 632.2 | 648.7 | 1.0 | 212.1 | 61.6 | 3.4 |
| w3013 | b3074 | 2711.4 | 2653.2 | 1.0 | 2576.4 | 760.8 | 3.4 |
| w3259 | b3324 | 840.9 | 1191.9 | 0.7 | 942.0 | 278.2 | 3.4 |
| w0719 | b0736 | 2884.4 | 2820.3 | 1.0 | 866.1 | 257.5 | 3.4 |
| w0765 | b0789 | 3699.1 | 3911.8 | 0.9 | 2615.0 | 783.7 | 3.3 |
| w0564 | b0574 | 1311.4 | 3713.2 | 0.4 | 584.5 | 175.8 | 3.3 |
| recT | | 1612.4 | 1717.9 | 0.9 | 303.3 | 91.9 | 3.3 |
| w0923 | b0948 | 9321.0 | 6900.1 | 1.4 | 4604.2 | 1402.6 | 3.3 |
| w0817 | b0841 | 3320.7 | 3960.8 | 0.8 | 3196.3 | 975.8 | 3.3 |
| w3086 | b3145 | 1310.1 | 1251.5 | 1.0 | 1040.6 | 317.9 | 3.3 |
| bisZ | | 6146.6 | 4998.7 | 1.2 | 4600.8 | 1407.5 | 3.3 |
| thrL | | 1057.1 | 1045.9 | 1.0 | 1851.9 | 566.6 | 3.3 |
| w0497 | b0506 | 9030.8 | 9211.8 | 1.0 | 5078.5 | 1555.4 | 3.3 |
| w1971 | b2012 | 1758.9 | 1667.2 | 1.1 | 691.8 | 213.9 | 3.2 |
| w0540 | b0550 | 2028.9 | 1744.8 | 1.2 | 1549.0 | 480.5 | 3.2 |
| w1630 | b1660 | 5454.2 | 5556.5 | 1.0 | 4639.8 | 1450.4 | 3.2 |
| cpsB | | 3575.1 | 4298.5 | 0.8 | 1022.1 | 322.1 | 3.2 |
| cydA | | 699.9 | 1392.5 | 0.5 | 963.9 | 305.9 | 3.2 |
| hisQ | | 1785.2 | 2681.4 | 0.7 | 608.3 | 194.5 | 3.1 |
| hisC | | 6681.3 | 9140.8 | 0.7 | 846.1 | 270.9 | 3.1 |
| w0500 | b0509 | 1305.4 | 1278.1 | 1.0 | 419.4 | 134.9 | 3.1 |
| w1174 | b1201 | 4364.8 | 3477.3 | 1.3 | 4444.2 | 1441.8 | 3.1 |
| ais | | 706.7 | 3093.8 | 0.2 | 352.9 | 114.6 | 3.1 |
| w0779 | b0803 | 1650.0 | 1698.6 | 1.0 | 333.4 | 108.6 | 3.1 |
| w1239 | b1268 | 2079.2 | 1408.0 | 1.5 | 3135.3 | 1028.5 | 3.0 |
| purB | | 18600.8 | 19192.0 | 1.0 | 5778.2 | 1902.4 | 3.0 |
| pth | | 3170.2 | 2879.8 | 1.1 | 961.3 | 316.5 | 3.0 |
| w0650 | b0660 | 22565.4 | 15873.4 | 1.4 | 6943.2 | 2288.0 | 3.0 |
| cheW | | 1753.3 | 1660.5 | 1.1 | 16269.0 | 5397.0 | 3.0 |
| w1399 | b1428 | 3396.4 | 3241.9 | 1.0 | 1677.5 | 560.3 | 3.0 |
| w0961 | b0987 | 879.4 | 968.1 | 0.9 | 432.4 | 144.6 | 3.0 |
| w0936 | b0961 | 1274.0 | 1621.9 | 0.8 | 613.8 | 205.8 | 3.0 |
| w0502 | b0511 | 5155.5 | 5061.0 | 1.0 | 2862.5 | 964.1 | 3.0 |
| w0822 | b0846 | 1673.8 | 2457.6 | 0.7 | 600.4 | 202.4 | 3.0 |
| entC | | 152.5 | 97.0 | 1.6 | 611.3 | 206.3 | 3.0 |
| sdhC | | 844.1 | 1314.1 | 0.6 | 1633.1 | 553.6 | 2.9 |
| w0509 | b0518 | 3075.7 | 3295.1 | 0.9 | 1828.1 | 620.4 | 2.9 |
| xasA | | 1931.3 | 2558.8 | 0.8 | 1157.5 | 394.7 | 2.9 |
| hyaE | | 676.4 | 1025.4 | 0.7 | 755.3 | 258.0 | 2.9 |
| w0539 | b0549 | 747.5 | 889.9 | 0.8 | 439.3 | 151.8 | 2.9 |
| w1115 | b1142 | 1661.8 | 2188.1 | 0.8 | 192.4 | 66.7 | 2.9 |
| hycH | | 288.2 | 502.4 | 0.6 | 665.1 | 232.8 | 2.9 |
| glnB | | 1596.2 | 2017.4 | 0.8 | 7231.5 | 2542.3 | 2.8 |
| w1302 | b1331 | 99632.3 | 107376.2 | 0.9 | 41005.5 | 14416.5 | 2.8 |
| cysA | | 2279.2 | 2408.4 | 0.9 | 1175.7 | 414.3 | 2.8 |
| codB | | 4134.2 | 2988.3 | 1.4 | 16969.3 | 6059.8 | 2.8 |
| rbsD | | 765.7 | 795.2 | 1.0 | 759.5 | 271.3 | 2.8 |
| w3180 | b3240 | 1863.2 | 1194.4 | 1.6 | 582.5 | 208.5 | 2.8 |
| gefL | | 560.6 | 561.3 | 1.0 | 702.5 | 254.1 | 2.8 |
| w0958 | b0984 | 2457.8 | 4067.5 | 0.6 | 1021.8 | 369.7 | 2.8 |
| aroC | | 11775.3 | 9917.9 | 1.2 | 10669.1 | 3864.7 | 2.8 |
| motA | | 2939.6 | 2956.1 | 1.0 | 11679.2 | 4245.3 | 2.8 |
| w3025 | b3086 | 1433.6 | 1291.0 | 1.1 | 1758.4 | 650.5 | 2.7 |
| hemK | | 1309.8 | 2201.0 | 0.6 | 710.0 | 263.6 | 2.7 |

TABLE 8-continued

Gene expressions in DM800 and DM803 when exposed to MMC

| Gene name | b # | DM800-MMC | DM800-control | DM800 ratio (MMC/control) | DM803-MMC | DM803-control | DM803 ratio (MMC/control) |
|---|---|---|---|---|---|---|---|
| glnK | | 408.6 | 208.4 | 2.0 | 571.9 | 212.8 | 2.7 |
| molR | | 2331.5 | 2500.4 | 0.9 | 1737.4 | 647.3 | 2.7 |
| w1130 | b1157 | 1347.6 | 1890.5 | 0.7 | 475.1 | 179.1 | 2.7 |
| w0128 | b0128 | 1773.0 | 1996.8 | 0.9 | 7243.6 | 2738.9 | 2.6 |
| potH | | 500.1 | 1228.0 | 0.4 | 641.9 | 243.8 | 2.6 |
| w0649 | b0659 | 8552.5 | 6250.8 | 1.4 | 2846.7 | 1095.1 | 2.6 |
| cspB | | 1529.3 | 1353.4 | 1.1 | 4972.3 | 1916.6 | 2.6 |
| w1030 | b1057 | 1588.1 | 2509.8 | 0.6 | 267.4 | 103.5 | 2.6 |
| purU | | 7223.2 | 5962.4 | 1.2 | 5262.9 | 2036.9 | 2.6 |
| pspD | | 4123.9 | 3232.2 | 1.3 | 3232.5 | 1251.9 | 2.6 |
| w1367 | b1396 | 1421.9 | 1262.8 | 1.1 | 402.2 | 155.9 | 2.6 |
| vacJ | | 3901.7 | 3263.7 | 1.2 | 3362.3 | 1305.4 | 2.6 |
| rimL | | 1674.8 | 2976.5 | 0.6 | 322.5 | 125.2 | 2.6 |
| w2436 | b2483 | 1505.8 | 2310.6 | 0.7 | 1501.8 | 584.0 | 2.6 |
| w1969 | b2010 | 3303.8 | 2815.0 | 1.2 | 3061.5 | 1190.7 | 2.6 |
| w1499 | b1528 | 2954.5 | 3022.6 | 1.0 | 1198.3 | 471.0 | 2.5 |
| w0608 | b0618 | 2142.0 | 2560.7 | 0.8 | 1265.6 | 499.3 | 2.5 |
| acrB | | 300.1 | 343.2 | 0.9 | 702.9 | 277.8 | 2.5 |
| fadL | | 11366.6 | 11834.8 | 1.0 | 6211.9 | 2462.1 | 2.5 |
| deoR | | 544.1 | 807.2 | 0.7 | 1026.9 | 408.3 | 2.5 |
| ccmF | | 4594.5 | 4971.3 | 0.9 | 3393.8 | 1352.8 | 2.5 |
| w0473 | b0482 | 1714.2 | 2540.3 | 0.7 | 2861.6 | 1141.4 | 2.5 |
| w1017 | b1044 | 1431.3 | 2703.5 | 0.5 | 1035.0 | 413.5 | 2.5 |
| sdiA | | 624.8 | 836.4 | 0.7 | 280.1 | 112.0 | 2.5 |
| w0845 | b0869 | 3115.9 | 3364.6 | 0.9 | 2606.5 | 1044.4 | 2.5 |
| w0702 | b0719 | 1662.1 | 2274.0 | 0.7 | 163.0 | 65.5 | 2.5 |
| nohA | | 6246.0 | 6739.5 | 0.9 | 3562.3 | 1439.6 | 2.5 |
| w0652 | b0662 | 3324.9 | 3936.8 | 0.8 | 2463.7 | 999.4 | 2.5 |
| w0538 | b0548 | 667.7 | 876.1 | 0.8 | 242.3 | 98.9 | 2.4 |
| w2124 | b2164 | 2328.3 | 2341.3 | 1.0 | 795.8 | 324.9 | 2.4 |
| w1336 | b1365 | 976.6 | 1330.0 | 0.7 | 832.5 | 340.1 | 2.4 |
| w0507 | b0516 | 2900.6 | 3116.9 | 0.9 | 1473.0 | 602.3 | 2.4 |
| ccmB | | 1241.9 | 1597.6 | 0.8 | 518.1 | 211.9 | 2.4 |
| marA | | 3033.3 | 3218.3 | 0.9 | 1832.6 | 751.7 | 2.4 |
| dcp | | 17199.9 | 15990.1 | 1.1 | 9211.8 | 3786.9 | 2.4 |
| dacB | | 385.1 | 673.3 | 0.6 | 399.3 | 164.3 | 2.4 |
| w0794 | b0818 | 6395.1 | 5722.4 | 1.1 | 4159.6 | 1718.0 | 2.4 |
| w0692 | b0709 | 7727.5 | 8615.3 | 0.9 | 1950.3 | 814.0 | 2.4 |
| trpL | | 646.3 | 734.9 | 0.9 | 93.1 | 39.0 | 2.4 |
| w1284 | b1313 | 3976.7 | 4821.7 | 0.8 | 282.3 | 118.5 | 2.4 |
| uraA | | 10187.2 | 8537.2 | 1.2 | 9902.4 | 4158.1 | 2.4 |
| w0980 | b1006 | 2643.2 | 2348.5 | 1.1 | 1308.5 | 552.5 | 2.4 |
| w3017 | b3078 | 9857.5 | 6296.2 | 1.6 | 6341.6 | 2689.7 | 2.4 |
| w1353 | b1382 | 928.5 | 824.8 | 1.1 | 370.0 | 157.8 | 2.3 |
| sdaA | | 13413.9 | 11886.2 | 1.1 | 4508.6 | 1928.7 | 2.3 |
| w0635 | b0645 | 1636.0 | 2598.8 | 0.6 | 957.8 | 409.8 | 2.3 |
| rpsV | | 1839.1 | 2871.6 | 0.6 | 393.4 | 168.6 | 2.3 |
| nuoM | | 43613.3 | 39960.8 | 1.1 | 10711.5 | 4591.6 | 2.3 |
| w1255 | b1284 | 3075.9 | 5314.3 | 0.6 | 1188.4 | 509.6 | 2.3 |
| fdnG | | 9178.0 | 9437.7 | 1.0 | 4206.3 | 1807.4 | 2.3 |
| mepA | | 3493.6 | 3401.6 | 1.0 | 1838.9 | 790.6 | 2.3 |
| w2751 | b2807 | 1852.2 | 1235.3 | 1.5 | 863.6 | 372.1 | 2.3 |
| w2593 | b2646 | 735.3 | 900.8 | 0.8 | 1259.4 | 546.5 | 2.3 |
| w0249 | b0257 | 1814.6 | 2321.4 | 0.8 | 918.5 | 399.2 | 2.3 |
| w0636 | b0646 | 4069.4 | 4708.4 | 0.9 | 4894.1 | 2129.4 | 2.3 |
| w0605 | b0615 | 3429.0 | 4612.5 | 0.7 | 1239.6 | 539.4 | 2.3 |
| w1405 | b1434 | 2637.5 | 2190.6 | 1.2 | 908.0 | 396.3 | 2.3 |
| w2056 | b2097 | 836.8 | 1201.3 | 0.7 | 894.6 | 392.8 | 2.3 |
| w1175 | b1202 | 5780.1 | 5190.3 | 1.1 | 3007.7 | 1325.5 | 2.3 |
| priC | | 341.8 | 156.1 | 2.2 | 1151.2 | 509.8 | 2.3 |
| cdsA | | 3469.5 | 2775.1 | 1.3 | 983.1 | 435.9 | 2.3 |
| w2536 | b2583 | 1891.7 | 2031.4 | 0.9 | 2102.6 | 932.6 | 2.3 |
| xylE | | 1373.3 | 1927.2 | 0.7 | 7998.9 | 3551.8 | 2.3 |
| w0135 | b0135 | 855.6 | 837.8 | 1.0 | 621.9 | 276.4 | 2.2 |
| dsdA | | 3589.2 | 3871.9 | 0.9 | 5594.6 | 2497.9 | 2.2 |
| w0611 | b0621 | 3552.7 | 4502.2 | 0.8 | 4335.0 | 1939.6 | 2.2 |
| napC | | 1956.7 | 2181.8 | 0.9 | 1111.9 | 500.4 | 2.2 |
| w1372 | b1401 | 12135.8 | 22057.4 | 0.6 | 555.5 | 250.5 | 2.2 |
| w0801 | b0825 | 2801.7 | 5636.8 | 0.5 | 920.2 | 417.5 | 2.2 |
| w2776 | b2835 | 3905.8 | 3284.2 | 1.2 | 2517.3 | 1143.3 | 2.2 |
| phpB | | 1409.6 | 1160.8 | 1.2 | 1214.4 | 553.1 | 2.2 |
| frvA | | 1064.7 | 1379.4 | 0.8 | 1191.0 | 544.1 | 2.2 |
| atoS | | 3671.2 | 4696.2 | 0.8 | 1737.9 | 793.9 | 2.2 |
| nadC | | 17324.6 | 18335.7 | 0.9 | 10757.4 | 4919.0 | 2.2 |

TABLE 8-continued

Gene expressions in DM800 and DM803 when exposed to MMC

| Gene name | b # | DM800-MMC | DM800-control | DM800 ratio (MMC/control) | DM803-MMC | DM803-control | DM803 ratio (MMC/control) |
|---|---|---|---|---|---|---|---|
| w1333 | b1362 | 1261.3 | 1693.1 | 0.7 | 121.3 | 55.6 | 2.2 |
| ptsI | | 34232.4 | 31354.3 | 1.1 | 18044.1 | 8284.2 | 2.2 |
| w2854 | b2915 | 870.3 | 1215.4 | 0.7 | 662.7 | 306.0 | 2.2 |
| pbpG | | 6944.6 | 6379.8 | 1.1 | 4932.9 | 2283.2 | 2.2 |
| w3083 | b3142 | 719.8 | 985.0 | 0.7 | 247.8 | 114.8 | 2.2 |
| w1144 | b1171 | 1358.2 | 1358.7 | 1.0 | 381.8 | 177.2 | 2.2 |
| ldcC | | 1862.3 | 1945.6 | 1.0 | 1001.1 | 465.0 | 2.2 |
| pspA | | 3173.9 | 2654.2 | 1.2 | 2159.0 | 1002.9 | 2.2 |
| w2619 | b2673 | 1006.0 | 1237.6 | 0.8 | 644.6 | 300.0 | 2.1 |
| w0157 | b0157 | 1346.3 | 1157.1 | 1.2 | 1018.0 | 474.0 | 2.1 |
| w2942 | b3003 | 1915.5 | 2314.6 | 0.8 | 13358.9 | 6228.9 | 2.1 |
| w2130 | b2170 | 5239.7 | 4874.9 | 1.1 | 3027.9 | 1425.0 | 2.1 |
| artJ | | 551.8 | 666.4 | 0.8 | 602.1 | 283.4 | 2.1 |
| w0784 | b0808 | 3315.6 | 3019.7 | 1.1 | 2233.9 | 1052.1 | 2.1 |
| w1992 | b2033 | 14633.5 | 12234.7 | 1.2 | 3432.2 | 1618.3 | 2.1 |
| w1086 | b1113 | 3355.4 | 3376.0 | 1.0 | 1210.4 | 571.5 | 2.1 |
| w4089 | b4184 | 527.0 | 904.7 | 0.6 | 921.5 | 437.1 | 2.1 |
| bioD | | 1185.3 | 1716.8 | 0.7 | 8262.4 | 3929.6 | 2.1 |
| w1738 | b1770 | 943.5 | 1171.6 | 0.8 | 745.3 | 355.1 | 2.1 |
| hisH | | 3550.4 | 5116.9 | 0.7 | 467.4 | 223.7 | 2.1 |
| w1404 | b1433 | 3838.7 | 2998.2 | 1.3 | 3076.7 | 1473.4 | 2.1 |
| hrsA | | 2276.9 | 2267.0 | 1.0 | 1635.6 | 784.4 | 2.1 |
| entE | | 1452.0 | 1208.2 | 1.2 | 1455.2 | 698.8 | 2.1 |
| w1244 | b1273 | 4472.8 | 7128.7 | 0.6 | 1505.4 | 723.7 | 2.1 |
| agaD | | 222.7 | 459.0 | 0.5 | 966.6 | 465.2 | 2.1 |
| w0136 | b0136 | 503.6 | 708.2 | 0.7 | 467.4 | 225.0 | 2.1 |
| gip | | 2057.9 | 2249.6 | 0.9 | 911.3 | 438.8 | 2.1 |
| w0935 | b0960 | 9810.7 | 9012.0 | 1.1 | 5596.6 | 2698.4 | 2.1 |
| w2098 | b2138 | 2860.2 | 1994.6 | 1.4 | 852.8 | 411.9 | 2.1 |
| dcuA | | 40430.1 | 43730.0 | 0.9 | 43935.5 | 21225.0 | 2.1 |
| w2787 | b2846 | 934.2 | 1289.9 | 0.7 | 461.0 | 222.7 | 2.1 |
| tap | | 4650.7 | 3999.2 | 1.2 | 27236.5 | 13172.8 | 2.1 |
| menF | | 5124.8 | 4998.4 | 1.0 | 1942.6 | 941.5 | 2.1 |
| w1016 | b1043 | 1399.6 | 3109.1 | 0.5 | 419.6 | 203.5 | 2.1 |
| w0638 | b0648 | 1838.6 | 2597.3 | 0.7 | 717.4 | 348.2 | 2.1 |
| caiF | | 428.4 | 546.9 | 0.8 | 485.8 | 235.9 | 2.1 |
| hypC | | 790.3 | 1039.8 | 0.8 | 1320.2 | 642.5 | 2.1 |
| w0459 | b0468 | 2299.1 | 1903.3 | 1.2 | 4101.2 | 1997.0 | 2.1 |
| w2476 | b2523 | 5684.6 | 5096.2 | 1.1 | 3252.2 | 1584.5 | 2.1 |
| w3023 | b3084 | 2445.4 | 2099.4 | 1.2 | 2283.8 | 1116.1 | 2.0 |
| w0609 | b0619 | 3301.9 | 3869.5 | 0.9 | 3035.2 | 1484.7 | 2.0 |
| bglB | | 1785.8 | 1853.5 | 1.0 | 3096.8 | 1515.1 | 2.0 |
| xseA | | 13206.6 | 6494.6 | 2.0 | 17733.8 | 8677.0 | 2.0 |
| cls | | 10644.6 | 9607.6 | 1.1 | 3932.1 | 1928.5 | 2.0 |
| w3401 | b3466 | 889.6 | 1114.2 | 0.8 | 633.3 | 310.7 | 2.0 |
| cynT | | 613.7 | 533.8 | 1.1 | 756.0 | 372.2 | 2.0 |
| w2994 | b3054 | 10114.3 | 7666.9 | 1.3 | 6222.5 | 3064.4 | 2.0 |
| w0814 | b0838 | 3255.0 | 4310.8 | 0.8 | 1521.7 | 751.0 | 2.0 |
| gltB | | 410.7 | 661.8 | 0.6 | 1198.4 | 592.2 | 2.0 |
| w1993 | b2034 | 10553.5 | 9621.4 | 1.1 | 2342.5 | 1158.0 | 2.0 |
| w1937 | b1973 | 693.7 | 780.6 | 0.9 | 812.1 | 401.6 | 2.0 |
| mreC | | 2248.8 | 2181.3 | 1.0 | 5387.3 | 2666.7 | 2.0 |
| w3094 | b3153 | 894.0 | 1318.6 | 0.7 | 549.0 | 272.4 | 2.0 |
| w0342 | b0350 | 4321.9 | 7657.0 | 0.6 | 2305.5 | 1144.3 | 2.0 |
| w0795 | b0819 | 5595.7 | 4122.2 | 1.4 | 4127.2 | 2049.1 | 2.0 |
| w2702 | b2760 | 6420.7 | 7051.8 | 0.9 | 4832.2 | 2405.3 | 2.0 |
| w0919 | b0944 | 1491.9 | 1676.6 | 0.9 | 539.4 | 268.8 | 2.0 |
| w4011 | b4103 | 1183.2 | 1937.3 | 0.6 | 1116.2 | 556.8 | 2.0 |
| apaH | | 1181.6 | 616.9 | 1.9 | 2062.9 | 1031.2 | 2.0 |
| w1140 | b1167 | 993.4 | 1779.5 | 0.6 | 37.8 | 75.6 | 0.5 |
| w3038 | b3096 | 914.3 | 643.0 | 1.4 | 393.6 | 787.9 | 0.5 |
| w0834 | b0858 | 1262.4 | 1631.2 | 0.8 | 83.6 | 167.8 | 0.5 |
| w1238 | b1267 | 2724.1 | 2000.4 | 1.4 | 189.3 | 381.0 | 0.5 |
| w0682 | b0699 | 1482.3 | 2557.1 | 0.6 | 76.2 | 154.2 | 0.5 |
| w3021 | b3082 | 953.3 | 551.5 | 1.7 | 367.0 | 742.7 | 0.5 |
| w2120 | b2160 | 3360.7 | 3036.7 | 1.1 | 411.9 | 834.3 | 0.5 |
| w2169 | b2210 | 17678.9 | 16595.6 | 1.1 | 1325.6 | 2697.8 | 0.5 |
| tonB | | 12234.9 | 9196.9 | 1.3 | 1263.6 | 2600.0 | 0.5 |
| w3071 | b3130 | 2847.9 | 3106.1 | 0.9 | 522.9 | 1076.3 | 0.5 |
| hybG | | 197.8 | 231.5 | 0.9 | 277.1 | 570.6 | 0.5 |
| w3057 | b3115 | 8841.4 | 9026.7 | 1.0 | 1268.7 | 2628.1 | 0.5 |
| w3140 | b3200 | 9118.3 | 7619.6 | 1.2 | 2245.5 | 4659.8 | 0.5 |
| w1001 | b1027 | 2875.6 | 4647.4 | 0.6 | 263.1 | 551.1 | 0.5 |
| ccmE | | 2672.6 | 3219.4 | 0.8 | 417.4 | 874.6 | 0.5 |

TABLE 8-continued

Gene expressions in DM800 and DM803 when exposed to MMC

| Gene name | b # | DM800-MMC | DM800-control | DM800 ratio (MMC/control) | DM803-MMC | DM803-control | DM803 ratio (MMC/control) |
|---|---|---|---|---|---|---|---|
| w3123 | b3184 | 5627.8 | 4212.9 | 1.3 | 775.2 | 1627.3 | 0.5 |
| w1227 | b1256 | 2123.5 | 2318.3 | 0.9 | 431.6 | 909.1 | 0.5 |
| fadD |  | 5851.1 | 7371.8 | 0.8 | 602.2 | 1272.2 | 0.5 |
| w1863 | b1895 | 853.4 | 1054.2 | 0.8 | 72.7 | 153.7 | 0.5 |
| w2973 | b3033 | 3719.6 | 3936.6 | 0.9 | 612.9 | 1295.5 | 0.5 |
| w1081 | b1108 | 8020.2 | 9265.7 | 0.9 | 2167.2 | 4582.7 | 0.5 |
| w2750 | b2806 | 3964.6 | 2858.7 | 1.4 | 757.1 | 1602.1 | 0.5 |
| w1893 | b1928 | 5043.4 | 4943.2 | 1.0 | 729.8 | 1551.4 | 0.5 |
| w0495 | b0504 | 3013.9 | 2653.4 | 1.1 | 370.2 | 801.8 | 0.5 |
| w3092 | b3151 | 1889.9 | 1880.4 | 1.0 | 737.3 | 1603.5 | 0.5 |
| w1181 | b1208 | 7798.7 | 5758.2 | 1.4 | 869.2 | 1895.1 | 0.5 |
| narV |  | 2637.0 | 3155.3 | 0.8 | 184.4 | 404.4 | 0.5 |
| truA |  | 11793.0 | 9691.1 | 1.2 | 2917.6 | 6458.7 | 0.5 |
| w1669 | b1701 | 9241.3 | 8606.6 | 1.1 | 2036.0 | 4536.0 | 0.4 |
| w2096 | b2136 | 5573.1 | 5194.1 | 1.1 | 738.2 | 1652.5 | 0.4 |
| w0560 | b0570 | 5151.7 | 6014.9 | 0.9 | 864.4 | 1935.4 | 0.4 |
| w0384 | b0392 | 1206.8 | 1717.0 | 0.7 | 114.3 | 259.2 | 0.4 |
| w3111 | b3170 | 8628.0 | 6645.7 | 1.3 | 2692.4 | 6162.1 | 0.4 |
| trpA |  | 6982.3 | 5116.3 | 1.4 | 288.9 | 663.8 | 0.4 |
| w0729 | b0753 | 1992.8 | 2456.6 | 0.8 | 300.9 | 692.5 | 0.4 |
| w0686 | b0703 | 11364.2 | 10525.1 | 1.1 | 506.9 | 1168.5 | 0.4 |
| glpB |  | 3375.9 | 2533.8 | 1.3 | 3108.0 | 7165.1 | 0.4 |
| w3069 | b3128 | 15445.7 | 42484.5 | 0.4 | 499.8 | 1153.3 | 0.4 |
| evgA |  | 3622.0 | 3054.8 | 1.2 | 605.2 | 1403.5 | 0.4 |
| hisA |  | 12808.2 | 13416.1 | 1.0 | 1336.8 | 3117.3 | 0.4 |
| w2146 | b2186 | 10558.5 | 9654.4 | 1.1 | 1037.4 | 2426.5 | 0.4 |
| w2535 | b2582 | 2865.9 | 4526.7 | 0.6 | 393.5 | 921.4 | 0.4 |
| pntB |  | 20402.7 | 20359.0 | 1.0 | 1205.5 | 2840.2 | 0.4 |
| w2195 | b2236 | 1406.5 | 728.5 | 1.9 | 234.1 | 555.8 | 0.4 |
| w1543 | b1572 | 1282.8 | 1569.8 | 0.8 | 120.9 | 287.6 | 0.4 |
| w0850 | b0874 | 3017.5 | 2927.9 | 1.0 | 738.9 | 1765.9 | 0.4 |
| btuE |  | 2923.2 | 2641.6 | 1.1 | 263.9 | 631.0 | 0.4 |
| w1395 | b1424 | 1949.0 | 1623.8 | 1.2 | 410.0 | 980.9 | 0.4 |
| w1356 | b1385 | 2167.3 | 1587.5 | 1.4 | 96.8 | 234.3 | 0.4 |
| w1213 | b1242 | 503.3 | 619.9 | 0.8 | 151.7 | 369.1 | 0.4 |
| w2361 | b2408 | 763.3 | 752.9 | 1.0 | 120.0 | 292.1 | 0.4 |
| w3104 | b3163 | 18167.7 | 11453.8 | 1.6 | 13491.8 | 32888.9 | 0.4 |
| w0748 | b0772 | 11979.9 | 9899.5 | 1.2 | 1966.2 | 4794.2 | 0.4 |
| w1192 | b1219 | 3462.0 | 3677.7 | 0.9 | 438.1 | 1068.7 | 0.4 |
| w3228 | b3293 | 2810.8 | 1965.5 | 1.4 | 313.1 | 764.1 | 0.4 |
| w2849 | b2909 | 10514.5 | 10130.8 | 1.0 | 2114.0 | 5172.6 | 0.4 |
| w1393 | b1422 | 7786.4 | 7668.8 | 1.0 | 1190.6 | 2921.0 | 0.4 |
| speG |  | 14600.8 | 12145.6 | 1.2 | 2225.6 | 5463.2 | 0.4 |
| w3041 | b3099 | 5252.8 | 5281.6 | 1.0 | 471.9 | 1163.2 | 0.4 |
| w3066 | b3125 | 27223.3 | 36983.8 | 0.7 | 1092.1 | 2695.7 | 0.4 |
| w2765 | b2824 | 851.9 | 964.4 | 0.9 | 148.9 | 368.0 | 0.4 |
| w1825 | b1857 | 5399.7 | 4629.8 | 1.2 | 637.0 | 1579.2 | 0.4 |
| w1281 | b1310 | 3066.4 | 5129.5 | 0.6 | 143.7 | 356.9 | 0.4 |
| w1117 | b1144 | 1417.4 | 1639.5 | 0.9 | 108.6 | 270.0 | 0.4 |
| w0549 | b0559 | 956.4 | 5470.4 | 0.2 | 115.5 | 287.2 | 0.4 |
| treA |  | 11547.4 | 11404.7 | 1.0 | 1095.3 | 2737.4 | 0.4 |
| w0778 | b0802 | 1350.5 | 1308.3 | 1.0 | 131.7 | 329.4 | 0.4 |
| w3129 | b3190 | 2307.5 | 1992.7 | 1.2 | 340.2 | 852.2 | 0.4 |
| w3218 | b3283 | 3878.7 | 2425.8 | 1.6 | 1252.5 | 3153.4 | 0.4 |
| w3053 | b3111 | 6234.8 | 6408.0 | 1.0 | 607.4 | 1542.6 | 0.4 |
| w0475 | b0484 | 15214.1 | 16208.9 | 0.9 | 709.7 | 1802.9 | 0.4 |
| w2117 | b2157 | 3070.1 | 2873.2 | 1.1 | 533.7 | 1364.3 | 0.4 |
| w1432 | b1461 | 1846.2 | 2349.9 | 0.8 | 90.3 | 231.7 | 0.4 |
| osmE |  | 2901.6 | 6072.9 | 0.5 | 350.0 | 900.3 | 0.4 |
| w1624 | b1654 | 6959.3 | 7199.0 | 1.0 | 1247.1 | 3214.9 | 0.4 |
| w0821 | b0845 | 8372.0 | 8637.9 | 1.0 | 1748.5 | 4513.0 | 0.4 |
| w0365 | b0373 | 2918.6 | 3790.8 | 0.8 | 280.0 | 723.3 | 0.4 |
| katE |  | 4260.9 | 3635.5 | 1.2 | 516.6 | 1343.5 | 0.4 |
| w0506 | b0515 | 2698.3 | 2939.2 | 0.9 | 582.6 | 1515.2 | 0.4 |
| w2354 | b2398 | 2997.8 | 3805.3 | 0.8 | 381.5 | 996.5 | 0.4 |
| sseA |  | 11236.9 | 13524.4 | 0.8 | 1461.2 | 3819.1 | 0.4 |
| w3091 | b3150 | 4653.7 | 4947.8 | 0.9 | 926.2 | 2450.6 | 0.4 |
| dadX |  | 14179.7 | 15104.4 | 0.9 | 1014.8 | 2688.2 | 0.4 |
| w1280 | b1309 | 7116.1 | 7431.6 | 1.0 | 485.6 | 1300.2 | 0.4 |
| w0909 | b0934 | 5777.4 | 6344.0 | 0.9 | 191.5 | 512.9 | 0.4 |
| w1253 | b1282 | 4767.1 | 6492.3 | 0.7 | 342.5 | 917.5 | 0.4 |
| w2977 | b3037 | 10325.0 | 9553.3 | 1.1 | 2711.8 | 7333.0 | 0.4 |
| w1876 | b1908 | 7904.1 | 7700.0 | 1.0 | 1834.1 | 4974.1 | 0.4 |
| w0674 | b0691 | 1466.3 | 2840.2 | 0.5 | 129.0 | 350.8 | 0.4 |

TABLE 8-continued

Gene expressions in DM800 and DM803 when exposed to MMC

| Gene name | b # | DM800-MMC | DM800-control | DM800 ratio (MMC/control) | DM803-MMC | DM803-control | DM803 ratio (MMC/control) |
|---|---|---|---|---|---|---|---|
| w0496 | b0505 | 860.2 | 954.3 | 0.9 | 107.7 | 293.4 | 0.4 |
| w3085 | b3144 | 8990.5 | 7250.8 | 1.2 | 2060.6 | 5627.0 | 0.4 |
| w1815 | b1847 | 16206.3 | 4874.5 | 3.3 | 236.0 | 660.6 | 0.4 |
| w1506 | b1535 | 1746.6 | 2351.1 | 0.7 | 504.8 | 1413.1 | 0.4 |
| w1020 | b1047 | 2890.7 | 3663.4 | 0.8 | 157.9 | 442.8 | 0.4 |
| dsbB | | 5243.3 | 4561.9 | 1.1 | 649.9 | 1848.6 | 0.4 |
| w1090 | b1117 | 3645.1 | 3701.4 | 1.0 | 359.8 | 1025.0 | 0.4 |
| w1880 | b1915 | 1778.5 | 1658.4 | 1.1 | 148.1 | 422.8 | 0.4 |
| w1138 | b1165 | 1592.9 | 1932.4 | 0.8 | 88.0 | 251.7 | 0.3 |
| w0345 | b0353 | 23531.8 | 26792.5 | 0.9 | 2375.5 | 6866.5 | 0.3 |
| ndk | | 13360.7 | 13564.1 | 1.0 | 1108.3 | 3204.9 | 0.3 |
| w1154 | b1181 | 3992.7 | 2962.9 | 1.3 | 336.5 | 995.2 | 0.3 |
| w1146 | b1173 | 1361.2 | 1800.5 | 0.8 | 35.4 | 105.1 | 0.3 |
| pepT | | 4280.0 | 6805.4 | 0.6 | 394.8 | 1170.9 | 0.3 |
| w0747 | b0771 | 1020.8 | 1582.4 | 0.6 | 206.3 | 613.2 | 0.3 |
| w3052 | b3110 | 4449.2 | 5096.1 | 0.9 | 768.8 | 2307.4 | 0.3 |
| w1465 | b1494 | 1154.2 | 1682.8 | 0.7 | 37.4 | 112.5 | 0.3 |
| w1173 | b1200 | 3963.5 | 3786.2 | 1.0 | 875.3 | 2636.8 | 0.3 |
| w1237 | b1266 | 3678.6 | 3075.5 | 1.2 | 330.0 | 1008.8 | 0.3 |
| w2480 | b2527 | 5210.0 | 3260.6 | 1.6 | 296.4 | 907.5 | 0.3 |
| cspF | | 769.7 | 724.6 | 1.1 | 1043.9 | 3221.9 | 0.3 |
| w1344 | b1373 | 12449.4 | 12132.6 | 1.0 | 631.0 | 1956.4 | 0.3 |
| w0356 | b0364 | 893.8 | 2593.5 | 0.3 | 10.4 | 32.6 | 0.3 |
| w0445 | b0453 | 3085.5 | 3417.8 | 0.9 | 208.0 | 664.3 | 0.3 |
| w1671 | b1703 | 10135.4 | 10732.8 | 0.9 | 617.4 | 1975.5 | 0.3 |
| w0483 | b0492 | 32526.5 | 25269.0 | 1.3 | 997.8 | 3218.2 | 0.3 |
| w1101 | b1128 | 8372.2 | 7496.5 | 1.1 | 1030.2 | 3328.9 | 0.3 |
| w1121 | b1148 | 13523.9 | 13946.7 | 1.0 | 994.8 | 3277.0 | 0.3 |
| fumA | | 63238.6 | 79002.7 | 0.8 | 1142.5 | 3808.2 | 0.3 |
| otsA | | 3996.5 | 3237.0 | 1.2 | 472.5 | 1597.7 | 0.3 |
| w3049 | b3107 | 1146.6 | 2524.7 | 0.5 | 53.4 | 180.9 | 0.3 |
| w1736 | b1768 | 5360.4 | 5223.0 | 1.0 | 270.9 | 918.4 | 0.3 |
| w1111 | b1138 | 2285.3 | 3266.6 | 0.7 | 172.2 | 586.3 | 0.3 |
| w1078 | b1105 | 7249.1 | 7241.5 | 1.0 | 336.8 | 1168.0 | 0.3 |
| nadE | | 7651.4 | 8555.6 | 0.9 | 750.5 | 2616.3 | 0.3 |
| w2863 | b2924 | 4415.5 | 3933.5 | 1.1 | 763.3 | 2661.9 | 0.3 |
| amiA | | 5181.5 | 4164.8 | 1.2 | 1454.0 | 5128.4 | 0.3 |
| gipC | | 2150.9 | 1770.1 | 1.2 | 2910.6 | 10306.1 | 0.3 |
| marR | | 1626.3 | 1757.0 | 0.9 | 147.1 | 523.2 | 0.3 |
| w2132 | b2172 | 4870.0 | 5975.5 | 0.8 | 339.6 | 1208.0 | 0.3 |
| w1814 | b1846 | 4710.1 | 4725.8 | 1.0 | 601.5 | 2148.6 | 0.3 |
| w2781 | b2840 | 2411.6 | 2180.0 | 1.1 | 323.1 | 1162.5 | 0.3 |
| w0806 | b0830 | 5660.3 | 7149.0 | 0.8 | 374.2 | 1356.2 | 0.3 |
| sbmC | | 15497.2 | 13575.9 | 1.1 | 2005.1 | 7281.2 | 0.3 |
| w2739 | b2795 | 8350.0 | 12065.7 | 0.7 | 1466.6 | 5391.5 | 0.3 |
| w1358 | b1387 | 5568.3 | 6108.2 | 0.9 | 279.4 | 1034.1 | 0.3 |
| w0842 | b0866 | 1432.7 | 2445.9 | 0.6 | 54.2 | 201.1 | 0.3 |
| w1282 | b1311 | 6776.5 | 7862.7 | 0.9 | 292.4 | 1090.9 | 0.3 |
| glk | | 6398.4 | 6720.8 | 1.0 | 675.1 | 2528.6 | 0.3 |
| w2286 | b2327 | 2122.7 | 1766.9 | 1.2 | 546.0 | 2070.8 | 0.3 |
| w1286 | b1315 | 2562.4 | 3691.1 | 0.7 | 103.1 | 391.1 | 0.3 |
| w1355 | b1384 | 3482.9 | 3590.2 | 1.0 | 90.5 | 350.2 | 0.3 |
| w1270 | b1299 | 5513.5 | 6834.7 | 0.8 | 355.7 | 1394.8 | 0.3 |
| w2099 | b2139 | 1029.7 | 906.0 | 1.1 | 106.5 | 418.0 | 0.3 |
| w1407 | b1436 | 749.6 | 682.5 | 1.1 | 14.0 | 54.9 | 0.3 |
| w3155 | b3215 | 913.5 | 1043.0 | 0.9 | 91.6 | 362.6 | 0.3 |
| w2511 | b2558 | 6964.6 | 7412.8 | 0.9 | 864.3 | 3453.5 | 0.3 |
| pntA | | 18845.0 | 19495.1 | 1.0 | 697.9 | 2832.4 | 0.2 |
| w3054 | b3112 | 1774.6 | 2168.9 | 0.8 | 56.8 | 235.3 | 0.2 |
| w0633 | b0643 | 6699.0 | 11110.2 | 0.6 | 152.1 | 631.4 | 0.2 |
| w0826 | b0850 | 2356.4 | 2497.1 | 0.9 | 125.2 | 527.4 | 0.2 |
| w1328 | b1357 | 1405.4 | 1746.9 | 0.8 | 7.6 | 32.1 | 0.2 |
| w0344 | b0352 | 5703.2 | 9448.7 | 0.6 | 317.6 | 1350.6 | 0.2 |
| narW | | 4827.2 | 5275.1 | 0.9 | 451.1 | 1919.6 | 0.2 |
| w1119 | b1146 | 5263.5 | 6210.8 | 0.8 | 130.3 | 564.5 | 0.2 |
| w0629 | b0639 | 4754.0 | 4261.2 | 1.1 | 1120.5 | 4889.2 | 0.2 |
| w2879 | b2940 | 3946.5 | 1727.3 | 2.3 | 281.8 | 1248.5 | 0.2 |
| w2137 | b2177 | 3760.4 | 3335.6 | 1.1 | 353.4 | 1573.1 | 0.2 |
| w0983 | b1009 | 1169.8 | 1186.2 | 1.0 | 66.5 | 296.6 | 0.2 |
| w3050 | b3108 | 7051.6 | 7672.6 | 0.9 | 390.7 | 1745.2 | 0.2 |
| w1042 | b1069 | 5901.1 | 5801.9 | 1.0 | 1017.7 | 4599.0 | 0.2 |
| w1298 | b1327 | 2105.4 | 2517.0 | 0.8 | 57.6 | 260.7 | 0.2 |
| w3047 | b3105 | 8464.9 | 9065.1 | 0.9 | 570.5 | 2624.0 | 0.2 |
| w0668 | b0685 | 4431.4 | 3088.6 | 1.4 | 318.4 | 1471.6 | 0.2 |

TABLE 8-continued

Gene expressions in DM800 and DM803 when exposed to MMC

| Gene name | b # | DM800-MMC | DM800-control | DM800 ratio (MMC/control) | DM803-MMC | DM803-control | DM803 ratio (MMC/control) |
|---|---|---|---|---|---|---|---|
| w0855 | b0879 | 4397.7 | 3462.3 | 1.3 | 2098.5 | 9718.9 | 0.2 |
| w0669 | b0686 | 2371.1 | 2887.9 | 0.8 | 185.7 | 873.3 | 0.2 |
| w1006 | b1033 | 7514.8 | 8532.4 | 0.9 | 449.3 | 2183.1 | 0.2 |
| hisD |  | 8934.6 | 9271.5 | 1.0 | 490.5 | 2443.1 | 0.2 |
| w0372 | b0380 | 2303.5 | 2793.8 | 0.8 | 96.2 | 481.6 | 0.2 |
| w1225 | b1254 | 1455.4 | 1378.9 | 1.1 | 241.2 | 1218.1 | 0.2 |
| w1137 | b1164 | 1801.0 | 1518.1 | 1.2 | 53.4 | 280.3 | 0.2 |
| w3039 | b3097 | 10297.8 | 10899.1 | 0.9 | 470.9 | 2476.5 | 0.2 |
| w1662 | b1694 | 6288.5 | 6529.8 | 1.0 | 488.8 | 2613.0 | 0.2 |
| w1129 | b1156 | 912.1 | 1118.2 | 0.8 | 44.4 | 242.2 | 0.2 |
| w0490 | b0499 | 57928.7 | 59454.4 | 1.0 | 7786.3 | 43190.2 | 0.2 |
| w0359 | b0367 | 5960.8 | 7575.1 | 0.8 | 508.8 | 2903.2 | 0.2 |
| w1004 | b1030 | 1265.7 | 2528.7 | 0.5 | 27.8 | 163.0 | 0.2 |
| ccmC |  | 1392.8 | 1425.9 | 1.0 | 59.4 | 352.2 | 0.2 |
| w0350 | b0358 | 2511.7 | 3611.1 | 0.7 | 62.7 | 380.2 | 0.2 |
| trpC |  | 10007.8 | 23940.6 | 0.4 | 421.9 | 2562.2 | 0.2 |
| w1299 | b1328 | 2565.5 | 1837.8 | 1.4 | 67.1 | 430.4 | 0.2 |
| w0478 | b0487 | 2303.2 | 2595.4 | 0.9 | 88.7 | 587.3 | 0.2 |
| w3098 | b3157 | 5948.5 | 6214.2 | 1.0 | 1142.5 | 7663.5 | 0.1 |
| hipB |  | 1299.7 | 2047.8 | 0.6 | 25.8 | 185.6 | 0.1 |
| w9688 | b0705 | 2081.9 | 1363.9 | 1.5 | 122.4 | 883.1 | 0.1 |
| w1816 | b1848 | 18614.3 | 3231.0 | 5.8 | 124.7 | 900.3 | 0.1 |
| menC |  | 5525.9 | 8590.7 | 0.6 | 244.3 | 1823.6 | 0.1 |
| narU |  | 6244.4 | 6678.0 | 0.9 | 559.1 | 4236.9 | 0.1 |
| cbi |  | 1725.9 | 1351.0 | 1.3 | 119.7 | 941.6 | 0.1 |
| w3055 | b3113 | 1865.9 | 2074.1 | 0.9 | 35.3 | 278.5 | 0.1 |
| w2869 | b2930 | 15958.1 | 16895.0 | 0.9 | 246.6 | 1970.2 | 0.1 |
| w0487 | b0496 | 1988.4 | 2379.9 | 0.8 | 95.5 | 777.4 | 0.1 |
| w2875 | b2936 | 6843.6 | 7758.0 | 0.9 | 235.8 | 1928.8 | 0.1 |
| w3160 | b3220 | 1100.3 | 963.4 | 1.1 | 91.4 | 806.3 | 0.1 |
| phoQ |  | 8670.4 | 10289.4 | 0.8 | 163.6 | 1484.0 | 0.1 |
| ldhA |  | 9971.9 | 10016.8 | 1.0 | 78.0 | 788.4 | 0.1 |
| w2101 | b2141 | 1452.9 | 1851.1 | 0.8 | 52.3 | 529.2 | 0.1 |
| w1402 | b1431 | 4730.2 | 4071.1 | 1.2 | 69.9 | 717.8 | 0.1 |
| uidB |  | 6144.1 | 6476.0 | 0.9 | 395.6 | 4081.9 | 0.1 |
| w0480 | b0489 | 8009.4 | 7942.3 | 1.0 | 302.4 | 3174.6 | 0.1 |
| w0626 | b0636 | 3193.6 | 4188.0 | 0.8 | 141.5 | 1580.2 | 0.1 |
| w1542 | b1571 | 1051.8 | 1175.0 | 0.9 | 22.1 | 275.2 | 0.1 |
| w1118 | b1145 | 3879.7 | 3857.0 | 1.0 | 87.8 | 1247.7 | 0.1 |
| w2026 | b2067 | 1456.5 | 3270.0 | 0.4 | 22.0 | 337.9 | 0.1 |
| w1325 | b1354 | 1084.3 | 1857.7 | 0.6 | 13.8 | 241.2 | 0.1 |
| w3062 | b3120 | 841.5 | 1073.1 | 0.8 | 10.3 | 193.4 | 0.1 |
| w0943 | b0968 | 1175.1 | 1146.1 | 1.0 | 21.9 | 442.3 | 0.0 |
| w3044 | b3102 | 3025.5 | 3670.0 | 0.8 | 34.4 | 698.5 | 0.0 |
| w1546 | b1576 | 1343.3 | 1668.5 | 0.8 | 5.0 | 113.9 | 0.0 |
| w0940 | b0965 | 2874.6 | 2907.6 | 1.0 | 34.8 | 925.2 | 0.0 |
| w2071 | b2112 | 1583.8 | 2171.7 | 0.7 | 13.7 | 428.0 | 0.0 |
| w0664 | b0681 | 5986.0 | 8122.3 | 0.7 | 35.0 | 1167.7 | 0.0 |
| w2012 | b2053 | 3678.7 | 4198.0 | 0.9 | 62.8 | 2505.6 | 0.0 |
| w0476 | b0485 | 9577.5 | 11490.0 | 0.8 | 89.6 | 4163.9 | 0.0 |
| w0479 | b0488 | 2163.7 | 1845.1 | 1.2 | 10.7 | 1159.8 | 0.0 |
| w0975 | b1001 | 1642.8 | 1249.9 | 1.3 | 3.5 | 489.8 | 0.0 |
| w1318 | b1347 | 1107.0 | 2655.3 | 0.4 | 1.4 | 308.5 | 0.0 |
| acpD |  | 1990.2 | 4539.4 | 0.4 | 0.0 | 287.0 | 0.0 |
| asr |  | 819.7 | 1306.6 | 0.6 | 0.0 | 199.7 | 0.0 |
| celA |  | 864.5 | 3806.8 | 0.2 | 0.0 | 512.6 | 0.0 |
| cirA |  | 8601.6 | 7219.3 | 1.2 | 0.0 | 1161.0 | 0.0 |
| cpsG |  | 1070.1 | 2212.1 | 0.5 | 0.0 | 8.9 | 0.0 |
| dedA |  | 1510.1 | 2016.6 | 0.7 | 0.0 | 208.3 | 0.0 |
| emrk |  | 2298.7 | 2752.0 | 0.8 | 0.0 | 444.5 | 0.0 |
| emrY |  | 1567.1 | 1436.2 | 1.1 | 0.0 | 407.5 | 0.0 |
| evgS |  | 455.7 | 574.5 | 0.8 | 0.0 | 439.3 | 0.0 |
| fumC |  | 540.2 | 591.2 | 0.9 | 0.0 | 175.8 | 0.0 |
| gadB |  | 1951.2 | 2743.6 | 0.7 | 0.0 | 81.7 | 0.0 |
| galS |  | 6159.6 | 7496.6 | 0.8 | 0.0 | 1028.9 | 0.0 |
| hrpA |  | 546.1 | 2814.8 | 0.2 | 0.0 | 147.3 | 0.0 |
| ogrK |  | 1246.5 | 1941.6 | 0.6 | 0.0 | 118.2 | 0.0 |
| pheM |  | 221.1 | 390.9 | 0.6 | 0.0 | 73.8 | 0.0 |
| potA |  | 2332.9 | 3825.0 | 0.6 | 0.0 | 375.0 | 0.0 |
| pspB |  | 610.6 | 1027.9 | 0.6 | 0.0 | 86.1 | 0.0 |
| relB |  | 1002.3 | 2072.5 | 0.5 | 0.0 | 92.3 | 0.0 |
| sieB |  | 523.8 | 928.1 | 0.6 | 0.0 | 21.1 | 0.0 |
| tynA |  | 2320.6 | 3208.4 | 0.7 | 0.0 | 447.3 | 0.0 |
| uidA |  | 753.8 | 1174.9 | 0.6 | 0.0 | 149.9 | 0.0 |

TABLE 8-continued

Gene expressions in DM800 and DM803 when exposed to MMC

| Gene name | b # | DM800-MMC | DM800-control | DM800 ratio (MMC/control) | DM803-MMC | DM803-control | DM803 ratio (MMC/control) |
|---|---|---|---|---|---|---|---|
| w0351 | b0359 | 1435.0 | 2731.1 | 0.5 | 0.0 | 72.1 | 0.0 |
| w0371 | b0379 | 1275.3 | 2035.9 | 0.6 | 0.0 | 243.3 | 0.0 |
| w0477 | b0486 | 2340.1 | 2797.3 | 0.8 | 0.0 | 1901.6 | 0.0 |
| w0481 | b0490 | 1952.8 | 2004.4 | 1.0 | 0.0 | 836.5 | 0.0 |
| w0482 | b0491 | 2892.8 | 2263.9 | 1.3 | 0.0 | 783.6 | 0.0 |
| w0501 | b0510 | 648.1 | 1159.1 | 0.6 | 0.0 | 55.3 | 0.0 |
| w0529 | b0539 | 764.4 | 968.4 | 0.8 | 0.0 | 548.7 | 0.0 |
| w0532 | b0542 | 753.5 | 1045.5 | 0.7 | 0.0 | 264.9 | 0.0 |
| w0533 | b0543 | 1016.7 | 1055.4 | 1.0 | 0.0 | 403.8 | 0.0 |
| w0552 | b0562 | 1225.7 | 3084.4 | 0.4 | 0.0 | 588.7 | 0.0 |
| w0553 | b0563 | 734.8 | 2584.4 | 0.3 | 0.0 | 277.1 | 0.0 |
| w0561 | b0571 | 11989.7 | 5479.6 | 2.2 | 0.0 | 636.5 | 0.0 |
| w0621 | b0631 | 1293.5 | 2605.4 | 0.5 | 0.0 | 170.6 | 0.0 |
| w0627 | b0637 | 1984.5 | 3647.0 | 0.5 | 0.0 | 299.3 | 0.0 |
| w0656 | b0671 | 2622.4 | 2405.6 | 1.1 | 0.0 | 624.8 | 0.0 |
| w0665 | b0682 | 786.7 | 1744.6 | 0.5 | 0.0 | 592.3 | 0.0 |
| w0672 | b0689 | 1354.0 | 1108.1 | 1.2 | 0.0 | 556.1 | 0.0 |
| w0807 | b0831 | 2452.0 | 3462.8 | 0.7 | 0.0 | 433.2 | 0.0 |
| w0808 | b0832 | 3057.1 | 3778.8 | 0.8 | 0.0 | 920.3 | 0.0 |
| w0809 | b0833 | 3158.7 | 3447.2 | 0.9 | 0.0 | 396.2 | 0.0 |
| w0819 | b0843 | 1481.2 | 2642.2 | 0.6 | 0.0 | 238.3 | 0.0 |
| w0910 | b0935 | 3537.6 | 4051.8 | 0.9 | 0.0 | 435.5 | 0.0 |
| w0911 | b0936 | 1362.2 | 1452.9 | 0.9 | 0.0 | 346.2 | 0.0 |
| w0912 | b0937 | 1344.2 | 1345.4 | 1.0 | 0.0 | 326.2 | 0.0 |
| w0913 | b0938 | 373.1 | 543.7 | 0.7 | 0.0 | 250.8 | 0.0 |
| w0914 | b0939 | 578.4 | 552.7 | 1.0 | 0.0 | 328.0 | 0.0 |
| w0915 | b0940 | 2161.6 | 1966.5 | 1.1 | 0.0 | 507.3 | 0.0 |
| w0916 | b0941 | 2523.2 | 2419.8 | 1.0 | 0.0 | 220.3 | 0.0 |
| w0917 | b0942 | 1050.8 | 1890.1 | 0.6 | 0.0 | 239.7 | 0.0 |
| w0939 | b0964 | 1052.3 | 1075.0 | 1.0 | 0.0 | 1051.3 | 0.0 |
| w0944 | b0969 | 2833.2 | 3213.2 | 0.9 | 0.0 | 480.3 | 0.0 |
| w0955 | b0981 | 3807.1 | 3809.9 | 1.0 | 0.0 | 529.4 | 0.0 |
| w0956 | b0982 | 986.7 | 520.9 | 1.9 | 0.0 | 161.0 | 0.0 |
| w0973 | b0999 | 2665.2 | 2466.9 | 1.1 | 0.0 | 705.6 | 0.0 |
| w0977 | b1003 | 3057.7 | 2353.2 | 1.3 | 0.0 | 428.1 | 0.0 |
| w0990 | b1016 | 698.0 | 1088.2 | 0.6 | 0.0 | 120.4 | 0.0 |
| w0993 | b1019 | 4411.3 | 4083.2 | 1.1 | 0.0 | 533.9 | 0.0 |
| w0995 | b1021 | 818.6 | 965.0 | 0.8 | 0.0 | 372.4 | 0.0 |
| w0997 | b1023 | 972.4 | 1064.8 | 0.9 | 0.0 | 17.8 | 0.0 |
| w1005 | b1031 | 970.4 | 2465.9 | 0.4 | 0.0 | 106.0 | 0.0 |
| w1008 | b1035 | 2819.0 | 3842.8 | 0.7 | 0.0 | 909.5 | 0.0 |
| w1023 | b1050 | 3725.1 | 3062.3 | 1.2 | 0.0 | 635.7 | 0.0 |
| w1070 | b1097 | 1352.2 | 1839.3 | 0.7 | 0.0 | 341.0 | 0.0 |
| w1120 | b1147 | 1528.0 | 2289.1 | 0.7 | 0.0 | 217.5 | 0.0 |
| w1122 | b1149 | 2784.5 | 2661.5 | 1.0 | 0.0 | 268.2 | 0.0 |
| w1123 | b1150 | 1299.2 | 1407.6 | 0.9 | 0.0 | 194.3 | 0.0 |
| w1124 | b1151 | 1190.2 | 962.1 | 1.2 | 0.0 | 240.8 | 0.0 |
| w1125 | b1152 | 2478.7 | 2830.5 | 0.9 | 0.0 | 378.3 | 0.0 |
| w1169 | b1196 | 736.1 | 1002.3 | 0.7 | 0.0 | 78.9 | 0.0 |
| w1222 | b1251 | 2361.8 | 2659.4 | 0.9 | 0.0 | 330.7 | 0.0 |
| w1224 | b1253 | 1462.6 | 1237.4 | 1.2 | 0.0 | 345.0 | 0.0 |
| w1260 | b1289 | 963.5 | 2507.3 | 0.4 | 0.0 | 353.6 | 0.0 |
| w1267 | b1296 | 9885.6 | 9682.9 | 1.0 | 0.0 | 628.8 | 0.0 |
| w1268 | b1297 | 6231.0 | 6335.9 | 1.0 | 0.0 | 1180.7 | 0.0 |
| w1269 | b1298 | 2180.4 | 2708.2 | 0.8 | 0.0 | 604.9 | 0.0 |
| w1291 | b1320 | 3070.2 | 3630.9 | 0.8 | 0.0 | 102.0 | 0.0 |
| w1293 | b1322 | 10797.3 | 10432.1 | 1.0 | 0.0 | 1328.7 | 0.0 |
| w1317 | b1346 | 1201.4 | 1869.7 | 0.6 | 0.0 | 2.7 | 0.0 |
| w1327 | b1356 | 7293.7 | 5900.3 | 1.2 | 0.0 | 99.2 | 0.0 |
| w1332 | b1361 | 979.7 | 1634.9 | 0.6 | 0.0 | 53.7 | 0.0 |
| w1335 | b1364 | 1031.9 | 1570.7 | 0.7 | 0.0 | 64.7 | 0.0 |
| w1339 | b1368 | 2401.5 | 2866.5 | 0.8 | 0.0 | 232.5 | 0.0 |
| w1340 | b1369 | 552.9 | 767.7 | 0.7 | 0.0 | 289.8 | 0.0 |
| w1343 | b1372 | 9415.8 | 9734.0 | 1.0 | 0.0 | 1484.3 | 0.0 |
| w1345 | b1374 | 1026.3 | 487.6 | 2.1 | 0.0 | 522.9 | 0.0 |
| w1346 | b1375 | 805.3 | 426.3 | 1.9 | 0.0 | 674.8 | 0.0 |
| w1360 | b1389 | 950.2 | 1644.0 | 0.6 | 0.0 | 254.5 | 0.0 |
| w1368 | b1397 | 1477.0 | 1619.0 | 0.9 | 0.0 | 175.4 | 0.0 |
| w1390 | b1419 | 1168.9 | 657.9 | 1.8 | 0.0 | 116.3 | 0.0 |
| w1391 | b1420 | 1225.3 | 1356.0 | 0.9 | 0.0 | 289.5 | 0.0 |
| w1403 | b1432 | 812.3 | 800.5 | 1.0 | 0.0 | 169.4 | 0.0 |
| w1660 | b1692 | 1390.9 | 1898.4 | 0.7 | 0.0 | 182.7 | 0.0 |
| w1673 | b1705 | 920.4 | 743.7 | 1.2 | 0.0 | 233.8 | 0.0 |
| w1701 | b1733 | 5606.3 | 5366.3 | 1.0 | 0.0 | 1445.5 | 0.0 |

TABLE 8-continued

Gene expressions in DM800 and DM803 when exposed to MMC

| Gene name | b # | DM800-MMC | DM800-control | DM800 ratio (MMC/control) | DM803-MMC | DM803-control | DM803 ratio (MMC/control) |
|---|---|---|---|---|---|---|---|
| w1733 | b1765 | 8186.5 | 8316.3 | 1.0 | 0.0 | 1117.1 | 0.0 |
| w1737 | b1769 | 3089.3 | 3553.2 | 0.9 | 0.0 | 418.7 | 0.0 |
| w2009 | b2050 | 8039.2 | 9293.5 | 0.9 | 0.0 | 868.0 | 0.0 |
| w2010 | b2051 | 2505.5 | 4017.0 | 0.6 | 0.0 | 617.7 | 0.0 |
| w2011 | b2052 | 3552.4 | 5133.3 | 0.7 | 0.0 | 1374.5 | 0.0 |
| w2078 | b2119 | 1991.3 | 2900.8 | 0.7 | 0.0 | 261.7 | 0.0 |
| w2133 | b2173 | 848.4 | 657.5 | 1.3 | 0.0 | 474.2 | 0.0 |
| w2138 | b2178 | 5382.5 | 4913.7 | 1.1 | 0.0 | 1245.3 | 0.0 |
| w2139 | b2179 | 6107.9 | 5671.8 | 1.1 | 0.0 | 1804.5 | 0.0 |
| w2140 | b2180 | 7963.0 | 4829.8 | 1.6 | 0.0 | 815.7 | 0.0 |
| w2141 | b2181 | 2156.1 | 691.5 | 3.1 | 0.0 | 934.4 | 0.0 |
| w2528 | b2575 | 5332.1 | 6275.8 | 0.8 | 0.0 | 876.9 | 0.0 |
| w2530 | b2577 | 2228.3 | 2337.0 | 1.0 | 0.0 | 849.9 | 0.0 |
| w2531 | b2578 | 2185.4 | 2216.2 | 1.0 | 0.0 | 736.1 | 0.0 |
| w2862 | b2923 | 2498.1 | 1707.4 | 1.5 | 0.0 | 747.4 | 0.0 |
| w2867 | b2928 | 3001.1 | 1618.2 | 1.9 | 0.0 | 1005.1 | 0.0 |
| w2868 | b2929 | 2890.3 | 2306.0 | 1.3 | 0.0 | 552.7 | 0.0 |
| w2878 | b2939 | 1151.8 | 439.8 | 2.6 | 0.0 | 373.7 | 0.0 |
| w2880 | b2941 | 1480.2 | 1128.1 | 1.3 | 0.0 | 179.2 | 0.0 |
| w3043 | b3101 | 1869.2 | 2394.6 | 0.8 | 0.0 | 353.3 | 0.0 |
| w3046 | b3104 | 1186.0 | 1498.4 | 0.8 | 0.0 | 504.3 | 0.0 |
| w3063 | b3121 | 961.7 | 1080.5 | 0.9 | 0.0 | 148.6 | 0.0 |
| w3084 | b3143 | 977.8 | 1260.3 | 0.8 | 0.0 | 74.4 | 0.0 |
| w3096 | b3155 | 1052.3 | 847.0 | 1.2 | 0.0 | 714.4 | 0.0 |
| w3130 | b3191 | 5254.6 | 4119.2 | 1.3 | 0.0 | 989.0 | 0.0 |
| w3133 | b3194 | 579.9 | 528.6 | 1.1 | 0.0 | 257.1 | 0.0 |
| w3265 | b3330 | 748.4 | 885.6 | 0.8 | 0.0 | 78.5 | 0.0 |
| xapR |  | 4531.8 | 4954.8 | 0.9 | 0.0 | 1106.9 | 0.0 |
|  | b3399 | 5216.0 | 2817.8 | 1.9 |  |  |  |

TABLE 9

Most highly expressed genes in Synechocystis sp. PCC6803 in minimal growth media (BG11 + 5 mM glucose).

| Systematic Name | Gene | Function | Transcript copy in total mRNA (Average copy = 1) |
|---|---|---|---|
| slr2051 | cpcG | phycobilisome rod-core linker polypeptide CpcG | 64.91 |
| sll1580 | cpcC | phycocyanin associated linker protein | 22.71 |
| slr0447 | amiC | negative alipliatic amidase regulator | 19.45 |
| sll1070 | tktA | transketolase | 19.24 |
| s110018 | cbbA | fructose-1,6-bisphosphate aldolase | 14.27 |
| slr0011 | rbcX | ND* | 12.00 |
| ssl0563 | psaC | photosystem I subunit VII | 11.31 |
| slr1655 | psaL | photosystem I subunit XI | 10.91 |
| sll0819 | psaF | photosystem I subunit III | 10.56 |
| sll1867 | psbA3 | photosystem II DI protein | 10.43 |
| sll1324 | atpF | ATP synthase subunit b | 10.37 |
| sll1746 | rpl12 | 50S ribosomal protein L12 | 10.13 |
| sll1099 | tufA | protein synthesis elongation factor Tu | 9.48 |
| slr0009 | rbcL | ribulose bisphosphate carboxylase large subunit | 8.39 |
| slr0012 | rbcS | ribulose bisphosphate carboxylase small subunit | 8.14 |
| sll1326 | atpA | ATP synthase a subunit | 7.72 |
| slr1908 |  | ND* | 7.62 |
| sll1578 | cpcA | phycocyanin a subunit | 7.60 |
| slr2067 | apcA | allophycocyanin a chain | 7.51 |
| slr2052 |  | ND* | 7.41 |
| sll1184 | ho | heme oxygenase | 7.27 |
| ssl3437 | rps17 | 30S ribosomal protein S17 | 7.26 |
| sll1786 |  | hypothetical protein (ND*) | 7.16 |
| ssl0020 | petF | ferredoxin | 7.07 |
| sll1812 | rps5 | 30S ribosomal protein S5 | 7.04 |

*ND = not determined

TABLE 10

Most highly induced genes in Synechocystis sp. PCC6803 in BG11 media containing 5 mm glucose, with 20 min of UV-B treatment at 20 $\mu ES^{-1}m^{-2}$ intensity.

| Systematic Name | Gene | Function | Data/Control | STD |
|---|---|---|---|---|
| ssr2595 | hliB | High light- inducible protein | 22.7 | 4.7 |
| slr1544 |  | ND* | 15.5 | 7.6 |
| sll0528 |  | ND* | 12.1 | 3.9 |
| sll1514 | hsp17 | small heatshock protein | 9.9 | 3.9 |
| slr1687 | nblB | phycobilisome degradation protein NblB | 8.2 | 1.9 |
| sll1483 |  | transforming growth factor induced protein | 7.8 | 2.2 |
| sll2012 | rpoD | RNA polymerase sigma factor | 6.3 | 2.0 |
| ssl1633 |  | CAB/ELIP/HLIP superfamily | 6.0 | 1.0 |
| ssl2542 | hliA | high light-inducible protein | 5.6 | 1.6 |
| sll0846 |  | ND* | 4.7 | 0.9 |
| slr1674 |  | ND* | 4.7 | 1.8 |

TABLE 10-continued

Most highly induced genes in Synechocystis sp. PCC6803 in BG11 media containing 5 mm glucose, with 20 min of UV-B treatment at 20 $\mu ES^{-1}m^{-2}$ intensity.

| Systematic Name | Gene | Function | Data/Control | STD |
|---|---|---|---|---|
| slr1604 | ftsH | Chloroplast associated protease FtsH | 4.6 | 1.9 |
| slr0320 |  | ND* | 4.5 | 2.2 |
| sll0306 | rpoD | RNA polymerase sigma factor | 4.4 | 1.0 |
| slr0228 | ftsR | cell division protein FtsH | 4.3 | 1.7 |
| slr1641 | clpB | ClpB protein | 4.3 | 1.1 |
| ssr2016 |  | ND* | 4.2 | 2.2 |
| sll1867 | psbA3 | photosystem II DI protein | 4.1 | 0.3 |

*ND = not determined

What is claimed is:

1. A method for identifying gene expression changes within a bacterial species comprising:
   (a) providing a comprehensive micro-array synthesized from DNA comprised in a bacterial species;
   (b) generating a first set of labeled probes from bacterial RNA, the RNA isolated from the bacterial species of step (a);
   (c) hybridizing the first set of labeled probes of step (b) to the comprehensive micro-array of step (a), wherein hybridization results in a detectable signal generated from the labeled probe;
   (d) measuring the signal generated by the hybridization of the first set of labeled probe to the comprehensive micro-array of step (c);
   (e) subjecting the bacterial species of step (a) to a gene expression altering condition whereby the gene expression profile of the bacterial species is altered to produce a modified bacterial species;
   (f) generating a second set of labeled probes from bacterial RNA, the RNA isolated from the modified bacterial species of step (e);
   (g) hybridizing the second set of labeled probes of step (f) to the comprehensive micro-array of step (a), wherein hybridization results in a detectable signal generated from the labeled probe;
   (h) measuring the signal generated by the hybridization of the second set of labeled probes to the comprehensive micro-array of step (g); and
   (i) comparing signal generated from the first hybridization to the signal generated from the second hybridization to identify gene expression changes within a bacterial species.

2. A method for identifying gene expression changes within a bacterial species comprising:
   (a) providing a comprehensive micro-array synthesized from DNA comprised in a bacterial species;
   (b) generating a first set of fluorescent cDNA from bacterial RNA, the RNA isolated from the bacterial species of step (a);
   (c) hybridizing the first set of fluorescent cDNA of step (b) to the comprehensive micro-array of step (a), wherein hybridization results in a detectable signal generated from the fluorescent cDNA;
   (d) measuring the signal generated by the hybridization of the first set of fluorescent cDNA to the comprehensive micro-array of step (c);
   (e) subjecting the bacterial species of step (a) to a gene expression altering condition whereby the gene expression profile of the bacterial species is altered to produce a modified bacterial species;
   (f) generating a second set of fluorescent cDNA from bacterial RNA, the RNA isolated from the modified bacterial species of step (e);
   (g) hybridizing the second set of fluorescent cDNA of step (f) to the comprehensive micro-array of step (a), wherein hybridization results in a detectable signal generated from the fluorescent cDNA;
   (h) measuring the signal generated by the hybridization of the second set of fluorescent cDNA to the comprehensive micro-array of step (g); and (i) comparing signal generated from the first hybridization to the signal generated from the second hybridization to identify gene expression changes within a bacterial species.

3. A method according to either claim 1 or 2 wherein the bacterial species is selected from the group consisting of enteric bacteria, Bacillus, Acinetobacter, Streptomyces, Methylobacter, Pseudomonas, Rhodobacter and Synechocystis.

4. A method according to either claim 1 or 2 wherein the signal generating label is selected from the group consisting of fluorescent moieties, chemiluminescent moieties, particles, enzymes, radioactive tags.

5. A method according to claim 4 wherein the signal generating label is a fluorescent moiety and is selected from the group consisting of cy3 and cy5.

6. A method according to either claim 1 or 2 wherein the comprehensive micro-array contains at least 75% of all open reading frames in the bacterial species.

7. A method according to claim 6 wherein the comprehensive micro-array contains from about 2000 to about 6000 open reading frames.

8. A method according to either claim 1 or 2 wherein the gene expression altering condition is selected from the group consisting of a condition altering the genotype of the bacterial species, a condition altering the growth of the bacterial species, exposure to mutagens, antibiotics, UV light, gamma-rays, x-rays, phage, macrophages, organic chemicals, inorganic chemicals, environmental pollutants, heavy metals, changes in temperature, changes in pH, conditions producing oxidative damage, DNA damage, anaerobiosis, depletion or addition of nutrients, addition of a growth inhibitor, and desiccation.

9. A method for quantitating the amount of protein specifying RNA contained within a genome comprising:
(a) providing a comprehensive micro-array comprising a multiplicity of open reading frames synthesized from genomic DNA comprised in a prokaryotic or eukaryotic organism;
(b) generating a set of fluorescent cDNA from total or poly-adenylated RNA isolated from the prokaryotic or eukaryotic organism of step (a);
(c) generating a set of fluorescent DNA from genomic DNA isolated from the prokaryotic or eukaryotic organism of step (a);
(d) hybridizing the fluorescent cDNA of step (b) to the comprehensive micro-array of step (a), wherein hybridization results in a first fluorescent signal generated from the fluorescent cDNA for each open reading frame;
(e) hybridizing the fluorescent DNA of step (c) to the comprehensive micro-array of step (a), wherein hybridization results in a second fluorescent signal generated from the fluorescent DNA for each open reading frame; and
(f) dividing, for each open reading frame, the first fluorescent signal into the second fluorescent signal to provide a quantitated measure of the amount of protein specifying RNA for each open reading frame.

10. A method for quantitating the amount of protein specifying RNA contained within a genome comprising:
(a) providing a comprehensive micro-array comprising a multiplicity of genes synthesized from genomic DNA comprised in a prokaryotic or eukaryotic organism;
(b) generating a set of fluorescent cDNA from total or poly-adenylated RNA isolated from the prokaryotic or eukaryotic organism of step (a);
(c) generating a set of fluorescent DNA from genomic DNA isolated from the prokaryotic or eukaryotic organism of step (a);
(d) hybridizing the fluorescent cDNA of step (b) to the comprehensive micro-array of step (a), wherein hybridization results in a first fluorescent signal generated from the fluorescent cDNA for each gene;
(e) hybridizing the fluorescent DNA of step (c) to the comprehensive micro-array of step (a), wherein hybridization results in a second fluorescent signal generated from the fluorescent DNA for each gene; and
(f) dividing, for each open reading frame, the first fluorescent signal into the second fluorescent signal to provide a quantitated measure of the amount of protein specifying RNA for each gene.

11. A method for identifying gene expression changes within a bacterial species according to either claim 1 or 2 providing for quantitating the amount of protein specifying RNA contained within a genome according to a method comprising:
(a) providing a comprehensive micro-array comprising a multiplicity of open reading frames synthesized from genomic DNA comprised in a prokaryotic or eukaryotic organism;
(b) generating a set of fluorescent cDNA from total or poly-adenylated RNA isolated from the prokaryotic or eukaryotic organism of step (a);
(c) generating a set of fluorescent DNA from genomic DNA isolated from the prokaryotic or eukaryotic organism of step (a);
(d) hybridizing the fluorescent cDNA of step (b) to the comprehensive micro-array of step (a), wherein hybridization results in a first fluorescent signal generated from the fluorescent cDNA for each open reading frame;
(e) hybridizing the fluorescent DNA of step (c) to the comprehensive micro-array of step (a), wherein hybridization results in a second fluorescent signal generated from the fluorescent DNA for each open reading frame; and
(f) dividing, for each open reading frame, the first fluorescent signal into the second fluorescent signal to provide a quantitated measure of the amount of protein specifying RNA for each open reading frame.

12. A method for identifying gene expression changes within a bacterial species according to either claim 1 or 2 providing for quantitating the amount of protein specifying RNA contained within a genome according to a method comprising:
(a) providing a comprehensive micro-array comprising a multiplicity of genes synthesized from genomic DNA comprised in a prokaryotic or eukaryotic organism;
(b) generating a set of fluorescent cDNA from total or poly-adenylated RNA isolated from the prokaryotic or eukaryotic organism of step (a);
(c) generating a set of fluorescent DNA from genomic DNA isolated from the prokaryotic or eukaryotic organism of step (a);
(d) hybridizing the fluorescent cDNA of step (b) to the comprehensive micro-array of step (a), wherein hybridization results in a first fluorescent signal generated from the fluorescent cDNA for each gene;
(e) hybridizing the fluorescent DNA of step (c) to the comprehensive micro-array of step (a), wherein hybridization results in a second fluorescent signal generated from the fluorescent DNA for each gene; and (f) dividing, for each open reading frame, the first fluorescent signal into the second fluorescent signal to provide a quantitated measure of the amount of protein specifying RNA for each gene.

13. A method for identifying gene expression changes within a genome according to claim 8 providing for quantitating the amount of protein specifying RNA contained within a genome according to a method comprising:

(a) providing a comprehensive micro-array comprising a multiplicity of open reading frames synthesized from genomic DNA comprised in a prokaryotic or eukaryotic organism;

(b) generating a set of fluorescent cDNA from total or poly-adenylated RNA isolated from the prokaryotic or eukaryotic organism of step (a);

(c) generating a set of fluorescent DNA from genomic DNA isolated from the prokaryotic or eukaryotic organism of step (a);

(d) hybridizing the fluorescent cDNA of step (b) to the comprehensive micro-array of step (a), wherein hybridization results in a first fluorescent signal generated from the fluorescent cDNA for each open reading frame;

(e) hybridizing the fluorescent DNA of step (c) to the comprehensive micro-array of step (a), wherein hybridization results in a second fluorescent signal generated from the fluorescent DNA for each open reading frame; and (f) dividing, for each open reading frame, the first fluorescent signal into the second fluorescent signal to provide a quantitated measure of the amount of protein specifying RNA for each open reading frame.

14. A method for identifying gene expression changes within a genome according to claim 8 providing for quantitating the amount of protein specifying RNA contained within a genome according to a method comprising:

(a) providing a comprehensive micro-array comprising a multiplicity of genes synthesized from genomic DNA comprised in a prokaryotic or eukaryotic organism;

(b) generating a set of fluorescent cDNA from total or poly-adenylated RNA isolated from the prokaryotic or eukaryotic organism of step (a);

(c) generating a set of fluorescent DNA from genomic DNA isolated from the prokaryotic or eukaryotic organism of step (a);

(d) hybridizing the fluorescent cDNA of step (b) to the comprehensive micro-array of step (a), wherein hybridization results in a first fluorescent signal generated from the fluorescent cDNA for each gene;

(e) hybridizing the fluorescent DNA of step (c) to the comprehensive micro-array of step (a), wherein hybridization results in a second fluorescent signal generated from the fluorescent DNA for each gene; and (f) dividing, for each open reading frame, the first fluorescent signal into the second fluorescent signal to provide a quantitated measure of the amount of protein specifying RNA for each gene.

\* \* \* \* \*

SEQUENCE LISTING

<160> NUMBER OF SEQ ID NOS: 2

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence:PRIMER

<400> SEQUENCE: 1
tggcacgcag gacagaa                                                17

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:PRIMER

<400> SEQUENCE: 2
taacaaatca gcataactca t                                           21